(12) United States Patent
Larsen

(10) Patent No.: US 11,365,204 B2
(45) Date of Patent: Jun. 21, 2022

(54) SUBSTITUTED DIHYDROTHIENOPYRIMIDINES AND THEIR USE AS PHOSPHODIESTERASE INHIBITORS

(71) Applicant: UNION therapeutics A/S, Hellerup (DK)

(72) Inventor: Jens Larsen, Ballerup (DK)

(73) Assignee: Union therapeutics A/S, Hellerup (DK)

( * ) Notice: Subject to any disclaimer, the term of this patent is extended or adjusted under 35 U.S.C. 154(b) by 0 days.

(21) Appl. No.: 16/648,263

(22) PCT Filed: Sep. 20, 2018

(86) PCT No.: PCT/EP2018/075438
§ 371 (c)(1),
(2) Date: Mar. 18, 2020

(87) PCT Pub. No.: WO2019/057806
PCT Pub. Date: Mar. 28, 2019

(65) Prior Publication Data
US 2020/0239493 A1  Jul. 30, 2020

(30) Foreign Application Priority Data
Sep. 20, 2017  (EP) .................................. 17020430

(51) Int. Cl.
C07D 495/04 (2006.01)
A61K 31/519 (2006.01)

(52) U.S. Cl.
CPC .......... *C07D 495/04* (2013.01); *A61K 31/519* (2013.01)

(58) Field of Classification Search
CPC ........................... C07D 495/04; A61K 31/519
See application file for complete search history.

(56) References Cited

U.S. PATENT DOCUMENTS

| 7,511,045 | B2 | 3/2009 | Hoenke et al. |
| 2007/0259846 | A1 | 11/2007 | Hoenke et al. |

FOREIGN PATENT DOCUMENTS

| WO | WO 2006/111549 | 10/2006 |
| WO | WO 2007/118793 | 10/2007 |
| WO | WO 2009/050236 | 4/2009 |
| WO | WO 2009/050242 | 4/2009 |
| WO | WO 2009/050248 | 4/2009 |
| WO | WO 2009/053268 | 4/2009 |
| WO | WO 2013/026797 | 2/2013 |
| WO | WO 2014/124860 | 8/2014 |

OTHER PUBLICATIONS

Garcia-Osta et al., Phosphodiesterases as Therapeutic Targets for Alzheimer's Disease, ACS Chem. Neurosci., 3(11): 832-44 (2012).*
Huang et al., The Next Generation of PDE4 Inhibitors, Curr Opin Chem Bid., 5(4): 432-8 (2001).*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Boswell Smith, V, Spina, D. "Selective phosphodiesterase 4 inhibitors in the treatment of allergy and inflammation" *Curr. Opinion Investig. Drugs*, 6(11), 2005, pp. 1136-1141.
Holden, C et al, "Monocyte Localization of Elevated cAMP Phosphodiesterase Activity in Atopic Dermatitis" *Journal of Investigative Dermatology*, 87(3), 1986, pp. 372-376.
Houslay, M.D. et al., "Phosphodiesterase-4 as a therapeutic target" *Drug Discovery Today*, 10 (22), 2005, pp. 1503-1519.
Kroegel, C. Foerster, M., "Phosphodiesterase-4 inhibitors as a novel approach for the treatment of respiratory disease: cilomilast"*M. Expert Opinion Investig. Drugs*, 16(1), 2007, pp. 109-124.
Lipworth B., "Phosphodiesterase-4 inhibitors for asthma and chronic obstructive pulmonary disease" *Lancet*, 365, 2005, pp. 167-175.
International Search Report for International Application No. PCT/EP2018/075348 (2 pages) (dated 2018).
Written Opinion of the International Search Authority for International Application No. PCT/EP2018/75348. (5 pages) (dated 2018).
Ferrer et al., "Clinical anti-inflammatory efficacy of arofylline, a new selective phosphodiesterase-4, in dogs with a atropic dermatitis", Veterinary Record, 145: 191-194 (1999).
Wittmann et al., "Phosphodiesterase 4 Inhibition in the Treatment of Psoriasis, Psoriatic Arthritis and Other Chronic Inflammatory Diseases", Dermatol. Ther. (Heidelb), 3: 1-15 (2013).
Bershad, "Atopic Dermatatis (Eczema)", Ann. Intern. Med., 155(9), Nov. 1, 2011 [Abstract only].

* cited by examiner

*Primary Examiner* — Deepak R Rao
(74) *Attorney, Agent, or Firm* — DLA Piper LLP (US)

(57) ABSTRACT

The present invention relates to novel substituted dihydrothienopyrimidines with phosphodiesterase inhibitory activity, as well as to their use as therapeutic agents in the treatment of inflammatory diseases and conditions.

17 Claims, No Drawings

SUBSTITUTED DIHYDROTHIENOPYRIMIDINES AND THEIR USE AS PHOSPHODIESTERASE INHIBITORS

This application is a national stage filing under 35 U.S.C. § 371 of International Application No. PCT/EP2018/075438, filed on Sep. 20, 2018, which claims priority of European Patent Application No. 17020430.9, filed on Sep. 20, 2017. The contents of these applications are each incorporated herein by reference.

FIELD OF THE INVENTION

The present invention relates to novel substituted dihydrothienopyrimidines with phosphodiesterase inhibitory activity, and to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) PDE4, PDE7 and PDE8 are selective for cAMP. PDE4 is the most important modulator of cAMP expressed in immune and inflammatory cells such as neutrophils, macrophages and T-lymphocytes. As cAMP is a key second messenger in the modulation of inflammatory responses, PDE4 has been found to regulate inflammatory responses of inflammatory cells by modulating proinflammatory cytokines such as TNF-α, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, psoriasis, inflammatory bowel disease such as Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175).

Numerous PDE4 inhibitors have been studied for their therapeutic effect on inflammatory diseases, primarily asthma and COPD.

WO 2006/111549, US 20070259846, WO 2009/050236, WO 2009/050242, and WO 2009/053268, (all Boehringer Ingelheim International) each disclose dihydrothieno-pyrimidines which are substituted with piperazine for the treatment of respiratory or inflammatory diseases. The compounds are stated to inhibit the PDE4B enzyme.

WO 2007/118793, WO 2009/050248, and WO 2013/026797 (all Boehringer Ingelheim International) each disclose dihydrothieno-pyrimidines which are substituted with piperidine for the treatment of respiratory or inflammatory diseases. The compounds are stated to inhibit the PDE4B enzyme.

There is a continuous need for developing novel PDE4 inhibitors which have a more favourable therapeutic window, i.e. fewer adverse effects, while retaining their therapeutic effect.

SUMMARY OF THE INVENTION

It is an object of the present invention to provide novel dihydrothieno-pyrimidines substituted with azetidine. In one aspect the present invention relates to PDE4 inhibitors that could have a stability profile in biological tissue that implies that a low systemic exposure of the compounds to be observed upon e.g. topical administration, indicating that the compounds of the present invention could have high clearance in human liver microsomes, that they could hydrolyse in human whole blood and could display stability towards enzymatic hydrolyses in human keratinocytes.

In one aspect the invention provides a compound of general formula (I)

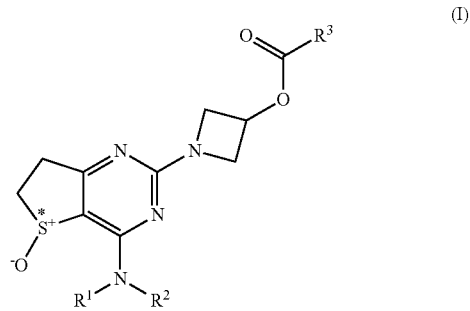

wherein
$R^1$ is hydrogen or $(C_1-C_4)$alkyl; and
wherein $R^2$ is selected from the group consisting of tetrahydropyranyl, oxaspiro-heptanyl, pyrrolidinyl and piperidinyl; wherein said pyrrolidinyl and piperidinyl are optionally substituted with one or more substituents independently selected from $R^4$; and
wherein $R^4$ is selected from the group consisting of —C(O)$(C_1-C_4)$alkyl, $(C_1-C_4)$alkyl, —S(O)$_2R_x$, —S(O)$_2NR_aR_b$, —C(O)O$(C_1-C_6)$alkyl, —C(O)NR$_a$R$_b$ and —$(C_1-C_4)$alkyl-C(O)NR$_a$R$_b$; and
wherein R$_a$ and R$_b$ are independently selected from the group consisting of hydrogen, $(C_1-C_4)$alkyl and halo$(C_1-C_4)$alkyl, or
R$_a$ and R$_b$ may together with the nitrogen atom to which they are attached form a (4-6)membered heterocycloalkyl, wherein said heterocycloalkyl is optionally substituted with one or more $(C_1-C_4)$alkyl; and
wherein $R^3$ is selected from the group consisting of $(C_1-C_6)$alkyl, $(C_3-C_6)$cycloalkyl, $(C_1-C_4)$alkyl$(C_3-C_6)$cycloalkyl, halo$(C_1-C_6)$alkyl, $(C_1-C_6)$alkoxy, $(C_1-C_6)$alkyl$(C_1-C_6)$alkoxy, halo$(C_1-C_4)$alkyloxy, (4-6)membered heterocycloalkyl, $(C_1-C_4)$alkyl(4-6)membered heterocycloalkyl, (5-6)membered heteroaryl, $(C_1-C_4)$alkyl(5-6)membered heteroaryl, aryl and $(C_1-C_4)$alkylaryl; wherein said alkyl, cycloalkyl, heterocycloalkyl, heteroaryl and aryl are optionally substituted with one or more substituents independently selected from $R^5$; and wherein $R^5$ is selected from the group consisting of halogen, cyano, hydroxyl, $(C_1-C_4)$-alkyl, halo$(C_1-C_4)$alkyl, halo$(C_1-C_4)$alkyloxy, $OR_x$, $SR_x$, $—S(O)_2R_x$, $—S(O)_2NR_aR_b$, $—C(O)R_x$, $—C(O)(OR_x)$, and $—C(O)NR_aR_b$; and wherein $R_x$ consist of $(C_1-C_4)$alkyl, $(C_3-C_6)$cycloalkyl, heterocycloalkyl; and wherein S* represent a chiral sulphur atom; and pharmaceutically acceptable salts, enantiomers, mixtures of enantiomers, diastereomers, mixtures of diastereomers, hydrates and solvates thereof.

In another aspect, the invention provides pharmaceutical compositions comprising a compound of the invention as defined above together with a pharmaceutically acceptable vehicle or excipient or pharmaceutically acceptable carrier(s), optionally together with one or more other therapeutically active compound(s).

In another aspect, the invention provides the use of a compound of the invention, for the manufacture of pharmaceutical compositions for the prophylaxis, treatment, prevention or amelioration of a disease, disorder or condition responsive to PDE4 inhibitory activity.

In yet another aspect the invention provides a method for treatment, prevention or alleviation of diseases, disorders or conditions responsive to PDE4 inhibitory activity, and which method comprises the step of administering to a living animal body a therapeutically effective amount of the compound of the invention.

Other objects of the invention will be apparent to the person skilled in the art from the following detailed description and examples.

DETAILED DESCRIPTION OF THE INVENTION

Definitions of the Invention

As used throughout the present specification and appended claims, the following terms have the indicated meaning:

The term "alkyl" is intended to indicate a radical obtained when one hydrogen atom is removed from a branched or linear hydrocarbon. Said alkyl comprises 1-6, such as 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The terms "alkyloxy" and "alkoxy" are intended to indicate a radical of the formula —OR', wherein R' is alkyl as indicated herein, wherein the alkyl group is appended to the parent molecular moiety through an oxygen atom, e.g. methoxy (—OCH$_3$), ethoxy (—OCH$_2$CH$_3$), n-propoxy, iso-propoxy, butoxy, tert-butoxy, and the like.

The term alkoxyalkyl is intended to indicate an alkyl group as defined above substituted with one or more alkoxy groups as defined above, e.g. methoxymethyl, ethoxymethyl, 2-methoxyethyl, 2-ethoxyethyl, 3-methoxyprop-1-yl, and the like The term "haloalkyl" is intended to indicate an alkyl group as defined herein substituted with one or more halogen atoms as defined herein, e.g. fluoro or chloro, such as fluoromethyl, difluoromethyl or trifluoromethyl.

The terms "haloalkyloxy" and "haloalkoxy" are intended to indicate a haloalkyl group as defined herein which is appended to the parent molecular moiety through an oxygen atom, such as difluoromethoxy or trifluoromethoxy.

The term "halogen" is intended to indicate a substituent from the 7$^{th}$ main group of the periodic table, such as fluoro, chloro and bromo.

The term "cyano" is intended to indicate a —CN group attached to the parent molecular moiety through the carbon atom.

The term "cycloalkyl" is intended to indicate a saturated cycloalkane hydrocarbon radical, comprising 3-7 carbon atoms, 3-6 carbon atoms, 3-5 carbon atoms, 3-4 carbon atoms, e.g. cyclopropyl, cyclobutyl, cyclopentyl and cyclohexyl.

The term "aryl" is intended to indicate a radical of aromatic carbocyclic rings comprising 6-13 carbon atoms, 6-9 carbon atoms, such as 6 carbon atoms, including fused carbocyclic rings with at least one aromatic ring. If the aryl group is a fused carbocyclic ring, the point of attachment of the aryl group to the parent molecular moiety may be through an aromatic or through an alifatic carbon atom within the aryl group. Representative examples of aryl include, but are not limited to phenyl, naphthyl, indenyl, indanyl, dihydronaphtyl, tetrahydronaphtyl and fluorenyl.

The term "heteroaryl" is intended to indicate radicals of monocyclic heteroaromatic rings comprising 5- or 6-membered ring which contains from 1-5 carbon atoms and from 1-4 heteroatoms selected from oxygen, sulphur and nitrogen. The heteroaryl radical may be connected to the parent molecular moiety through a carbon atom or a nitrogen atom contained anywhere within the heteroaryl group. Representative examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "heterocycloalkyl" is intended to indicate a cycloalkane radical as described herein, wherein one or more carbon atoms are replaced by heteroatoms, comprising 1-6 carbon atoms, e.g. 2-5 or 2-4 carbon atoms, further comprising 1-3 heteroatoms, preferably 1 to 2 heteroatoms, selected from O, N, or S, S(=O) or S(=O)$_2$. The heterocycloalkyl radical may be connected to the parent molecular moiety through a carbon atom or a nitrogen atom contained anywhere within the heterocycloalkyl group. Representative examples of heterocycloalkyl groups include, but are not limited to azepanyl, azetidinyl, aziridinyl, dioxolanyl, dioxolyl, imidazolidinyl, morpholinyl, oxetanyl, piperazinyl, piperidinyl, pyrrolidinyl, tetrahydrofuranyl, tetrahydropyranyl, tetrahydrothiophenyl, tetrahydrothiopyranyl.

The term "(4-6) membered heterocycloalkyl" is intended to indicate a heterocyloalkyl as defined herein, comprising 4-6 ring-atoms, and comprising 1-5 carbon atoms, e.g. 2-5 or 2-4 carbon atoms, further comprising 1-3 heteroatoms, preferably 1 to 2 heteroatoms, selected from O, N, S, S(=O) or S(=O)$_2$. Representative examples of (4-6) membered heterocycloalkyl groups include azetidinyl, dioxanyl, dioxolanyl, imidazolidinyl, morpholinyl, thiomorpholinyl, thiomorpholinyl-1-oxide, thiomorpholinyl-1,1-dioxide, oxetanyl, piperazinyl, piperidinyl, pyrrolidinyl, tetrahydrofuranyl, tetrahydropyranyl, tetrahydrothiopyranyl, tetrahydrothiophenyl, thietanyl, dioxothianyl.

The term "(5-6) membered heteroaryl" is intended to indicate radicals of monocyclic heteroaromatic rings comprising 5- or 6-membered ring which contains from 1-5 carbon atoms e.g. 2-5 or 2-4 carbon atoms, and from 1-4 heteroatoms, preferably 1 to 3 heteroatoms, e.g. 1-2 heteroatoms selected from oxygen, sulphur and nitrogen. The heteroaryl radical may be connected to the parent molecular moiety through a carbon atom or a nitrogen atom contained anywhere within the heteroaryl group. Representative examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-6 carbon atoms, and preferably comprises 1-5, e.g. 1-4, e.g. 1-3, e.g. 1-2 carbon atoms. The term includes alkyl, cycloalkyl and aryl, as indicated herein.

In some instances, the number of carbon atoms in a hydrocarbon radical (e.g. alkyl, cycloalkyl and aryl) is indicated by the prefix "$(C_a-C_b)$", wherein a is the minimum number and b is the maximum number of carbons in the hydrocarbon radical. Thus, for example $(C_1-C_4)$alkyl is intended to indicate an alkyl radical comprising from 1 to 4 carbon atoms, and $(C_3-C_6)$cycloalkyl is intended to indicate a cycloalkyl radical comprising from 3 to 6 carbon ring atoms.

The term "hydroxyalkyl" is intended to indicate an alkyl group as defined above substituted with one or more hydroxy, e.g. hydroxymethyl, hydroxyethyl, hydroxypropyl.

The term "hydroxyl" is intended to indicate an —OH group.

The term "oxo" is intended to indicate an oxygen atom which is connected to the parent molecular moiety via a double bond (=O).

The group C(O) is intended to represent a carbonyl group (C=O).

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzene-sulfonic, ethane-1,2-disulfonic, 2-hydroxy ethanesulfonic acid, toluene-sulfonic, sulfamic or fumaric acid. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

The terms "disease", "condition" and "disorder" as used herein are used inter-changeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

EMBODIMENTS OF THE INVENTION

In one aspect the invention provides a compound of general formula (I)

(I)

wherein
$R^1$ is hydrogen or $(C_1-C_4)$alkyl; and
wherein $R^2$ is selected from the group consisting of tetrahydropyranyl, oxaspiro-heptanyl, pyrrolidinyl and piperidinyl; wherein said pyrrolidinyl and piperidinyl are optionally substituted with one or more substituents independently selected from $R^4$; and
wherein $R^4$ is selected from the group consisting of —C(O)$(C_1-C_4)$alkyl, $(C_1-C_4)$alkyl, —S(O)$_2R_x$, —S(O)$_2NR_aR_b$, —C(O)O($C_1-C_6$)alkyl, —C(O)NR$_a$R$_b$ and —($C_1-C_4$)alkyl-C(O)NR$_a$R$_b$; and
wherein R$_a$ and R$_b$ are independently selected from the group consisting of hydrogen, $(C_1-C_4)$alkyl and halo$(C_1-C_4)$alkyl, or
R$_a$ and R$_b$ may together with the nitrogen atom to which they are attached form a (4-6)membered heterocycloalkyl, wherein said heterocycloalkyl is optionally substituted with one or more $(C_1-C_4)$alkyl; and
wherein $R^3$ is selected from the group consisting of $(C_1-C_6)$alkyl, $(C_3-C_6)$cycloalkyl, $(C_1-C_4)$alkyl$(C_3-C_6)$cycloalkyl, halo$(C_1-C_6)$alkyl, $(C_1-C_6)$alkoxy, $(C_1-C_6)$alkyl$(C_1-C_6)$alkoxy, halo$(C_1-C_4)$alkyloxy, (4-6)membered heterocycloalkyl, $(C_1-C_4)$alkyl(4-6)membered heterocycloalkyl, (5-6)membered heteroaryl, $(C_1-C_4)$alkyl(5-6)membered heteroaryl, aryl and $(C_1-C_4)$alkylaryl; wherein said alkyl, cycloalkyl, heterocycloalkyl, heteroaryl and aryl are optionally substituted with one or more substituents independently selected from $R^5$; and
wherein $R^5$ is selected from the group consisting of halogen, cyano, hydroxyl, $(C_1-C_4)$-alkyl, halo$(C_1-C_4)$alkyl, halo$(C_1-C_4)$alkyloxy, OR$_x$, SR$_x$, —S(O)$_2R_x$, —S(O)$_2NR_aR_b$, —C(O)R$_x$, —C(O)(OR$_x$), and —C(O)NR$_a$R$_b$; and
wherein R$_x$ consist of $(C_1-C_4)$alkyl, $(C_3-C_6)$cycloalkyl, heterocycloalkyl; and
wherein S* represents a chiral sulphur atom; and
pharmaceutically acceptable salts, enantiomers, mixtures of enantiomers, diastereomers, mixtures of diastereomers, hydrates and solvates thereof.

In another embodiment of the present invention in formula (I)
$R^1$ is hydrogen or $(C_1-C_4)$alkyl; and
$R^2$ is selected from the group consisting of tetrahydropyranyl, oxaspiroheptanyl, pyrrolidinyl and piperidinyl; wherein said pyrrolidinyl and piperidinyl are optionally substituted with one or more substituents independently selected from $R^4$; and
$R^4$ is selected from the group consisting of —C(O)(C$_1$-C$_4$)alkyl, (C$_1$-C$_4$)alkyl, —C(O)O(C$_1$-C$_6$)alkyl, —C(O)NR$_a$R$_b$ and —(C$_1$-C$_4$)alkyl-C(O)NR$_a$R$_b$; and
R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl; and
$R^3$ is selected from the group consisting of (C$_1$-C$_6$)alkyl, (C$_3$-C$_6$)cycloalkyl, (C$_1$-C$_4$)-alkyl(C$_3$-C$_6$)cycloalkyl, halo(C$_1$-C$_6$)alkyl, (C$_1$-C$_6$)alkoxy, (C$_1$-C$_6$)alkoxy(C$_1$-C$_6$)alkyl, halo(C$_1$-C$_4$)alkyloxy, (4-6)membered heterocycloalkyl, (C$_1$-C$_4$)alkyl(4-6)membered heterocycloalkyl, (5-6)membered heteroaryl, (C$_1$-C$_4$)alkyl(5-6)membered heteroaryl, aryl and (C$_1$-C$_4$)alkylaryl; wherein said heterocycloalkyl, heteroaryl and aryl are optionally substituted with one or more substituents independently selected from $R^5$; and
$R^5$ is selected from the group consisting of halogen, cyano, hydroxyl, (C$_1$-C$_4$)alkyl, halo(C$_1$-C$_4$)alkyl, halo(C$_1$-C$_4$)alkyloxy, OR$_x$, SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and
R$_x$ is (C$_1$-C$_4$)alkyl; and
S* represents a chiral sulphur atom; and
pharmaceutically acceptable salts, enantiomers, mixtures of enantiomers, diastereomers, mixtures of diastereomers, hydrates and solvates thereof.

In another embodiment of the present invention in formula (I), R' is hydrogen or (C$_1$-C$_4$)alkyl; and $R^2$ is selected from the group consisting of tetrahydropyranyl, oxaspiroheptanyl, pyrrolidinyl and piperidinyl; wherein said pyrrolidinyl and piperidinyl are optionally substituted —C(O)(C$_1$-C$_4$)alkyl; and $R^3$ is selected from the group consisting of (C$_1$-C$_6$)alkyl, (C$_3$-C$_6$)cycloalkyl, (C$_1$-C$_4$)alkyl(C$_3$-C$_6$)cycloalkyl, halo(C$_1$-C$_6$)alkyl, (C$_1$-C$_6$)alkoxy, (C$_1$-C$_6$)alkyl(C$_1$-C$_6$)alkoxy, halo(C$_1$-C$_4$)alkyloxy, (4-6)membered hetero-cycloalkyl, (C$_1$-C$_4$)alkyl(4-6)membered heterocycloalkyl, (5-6)membered heteroaryl, (C$_1$-C$_4$)alkyl(5-6)membered heteroaryl, aryl and (C$_1$-C$_4$)alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, hydroxyl, (C$_1$-C$_4$)alkyl, halo(C$_1$-C$_4$)alkyl, halo(C$_1$-C$_4$)alkyloxy, OR$_x$, SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)-membered heterocycloalkyl, wherein said heterocycloalkyl is optionally substituted with one or more (C$_1$-C$_4$)alkyl.

In another embodiment of the present invention in formula (I), $R^1$ is hydrogen or (C$_1$-C$_4$)alkyl; and $R^2$ is selected from the group consisting of tetrahydropyranyl, oxaspiroheptanyl, pyrrolidinyl and piperidinyl; wherein said pyrrolidinyl and piperidinyl are optionally substituted with $R^4$; and $R^4$ is selected from the group consisting of —C(O)(C$_1$-C$_4$)alkyl, and —C(O)O(C$_1$-C$_6$)alkyl; and $R^3$ is selected from the group consisting of (C$_1$-C$_6$)alkyl, (C$_3$-C$_6$)cycloalkyl, (C$_1$-C$_4$)alkyl(C$_3$-C$_6$)cycloalkyl, halo(C$_1$-C$_6$)alkyl, (C$_1$-C$_6$)alkoxy, (C$_1$-C$_6$)alkyl(C$_1$-C$_6$)alkoxy, halo(C$_1$-C$_4$)alkyloxy, (4-6)membered heterocycloalkyl, (C$_1$-C$_4$)alkyl(4-6)membered heterocycloalkyl, (5-6)membered heteroaryl, (C$_1$-C$_4$)alkyl(5-6)membered heteroaryl, aryl and (C$_1$-C$_4$)alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, cyano, hydroxyl, (C$_1$-C$_4$)alkyl, halo(C$_1$-C$_4$)alkyl, halo(C$_1$-C$_4$)alkyloxy, OR$_x$, SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), $R^1$ is hydrogen or (C$_1$-C$_4$)alkyl; and $R^2$ is selected from the group consisting of tetrahydropyranyl, oxaspiroheptanyl, pyrrolidinyl and piperidinyl, wherein said pyrrolidinyl and piperidinyl are optionally substituted with $R^4$; and $R^4$ is selected from the group consisting of —C(O)(C$_1$-C$_4$)alkyl, and —C(O)O(C$_1$-C$_4$)alkyl; and $R^3$ is selected from the group consisting of (C$_3$-C$_6$)cycloalkyl, (4-6)membered heterocycloalkyl, and (5-6)membered heteroaryl, all of which are optionally substituted with one or more substituents independently selected from $R^5$; and $R^5$ is selected from the group consisting of halogen, cyano, hydroxyl, (C$_1$-C$_4$)alkyl, halo(C$_1$-C$_4$)alkyl and halo(C$_1$-C$_4$)alkyloxy, OR$_x$, SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), $R^1$ is hydrogen or (C$_1$-C$_4$)alkyl; and $R^2$ is selected from the group consisting of tetrahydropyranyl, oxaspiroheptanyl, pyrrolidinyl and piperidinyl, wherein said pyrrolidinyl and piperidinyl are optionally substituted with —C(O)(C$_1$-C$_4$)alkyl; and $R^3$ is selected from the group consisting of (C$_3$-C$_6$)cycloalkyl, (4-6)membered heterocycloalkyl, and (5-6)membered heteroaryl.

In another embodiment of the present invention in formula (I), $R^1$ is hydrogen or (C$_1$-C$_4$)alkyl; and $R^2$ is oxaspiroheptanyl; and $R^3$ is selected from the group consisting of (C$_1$-C$_6$)alkyl, (C$_3$-C$_6$)cycloalkyl, (C$_1$-C$_4$)alkyl(C$_3$-C$_6$)cycloalkyl, halo(C$_1$-C$_6$)alkyl, (C$_1$-C$_6$)alkoxy, (C$_1$-C$_6$)alkyl(C$_1$-C$_6$)alkoxy, halo(C$_1$-C$_4$)alkyloxy, (4-6)membered hetero-cycloalkyl, (C$_1$-C$_4$)alkyl(4-6)membered heterocycloalkyl, (5-6)membered heteroaryl, (C$_1$-C$_4$)alkyl(5-6)membered heteroaryl, aryl and (C$_1$-C$_4$)alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, cyano, hydroxyl, (C$_1$-C$_4$)alkyl, halo(C$_1$-C$_4$)alkyl and halo(C$_1$-C$_4$)-alkyloxy, OR$_x$, SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), R$^1$ is hydrogen or (C$_1$-C$_4$)alkyl; and R$^2$ is oxaspiroheptanyl; and R$^3$ is selected from the group consisting of (C$_3$-C$_6$)cycloalkyl, (4-6)membered heterocycloalkyl, and (5-6)membered heteroaryl, all of which are optionally substituted with one or more substituents independently selected from R$^5$; and R$^5$ is selected from the group consisting of halogen, cyano, hydroxyl, (C$_1$-C$_4$)alkyl, halo(C$_1$-C$_4$)alkyl and halo(C$_1$-C$_4$)alkyloxy, OR$_x$, —SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), R$^1$ is hydrogen or (C$_1$-C$_4$)alkyl; and R$^2$ is oxaspiroheptanyl; and R$^3$ is selected from the group consisting of (C$_3$-C$_6$)cycloalkyl, (4-6)membered heterocycloalkyl, and (5-6)membered heteroaryl.

In another embodiment of the present invention in formula (I), R$^1$ is hydrogen; and R$^2$ is oxaspiroheptanyl; and R$^3$ is selected from the group consisting of (4-6)membered heterocycloalkyl, and (5-6)membered heteroaryl.

In another embodiment of the present invention in formula (I), R$^1$ is hydrogen or (C$_1$-C$_4$)alkyl; and R$^2$ is pyrrolidinyl, which is optionally substituted with R$^4$; R$^4$ is selected from the group consisting of —C(O)(C$_1$-C$_4$)alkyl, (C$_1$-C$_4$)alkyl, —C(O)O(C$_1$-C$_6$)alkyl, —C(O)NR$_a$R$_b$ and —(C$_1$-C$_4$)alkyl-C(O)NR$_a$R$_b$; R$^3$ is selected from the group consisting of (C$_1$-C$_6$)alkyl, (C$_3$-C$_6$)cycloalkyl, (C$_1$-C$_4$)alkyl(C$_3$-C$_6$)cycloalkyl, halo(C$_1$-C$_6$)alkyl, (C$_1$-C$_6$)alkoxy, (C$_1$-C$_6$)alkyl(C$_1$-C$_6$)alkoxy, halo(C$_1$-C$_4$)alkyloxy, (4-6)membered heterocycloalkyl, (C$_1$-C$_4$)alkyl(4-6)membered heterocycloalkyl, (5-6)membered heteroaryl, (C$_1$-C$_4$)alkyl(5-6)membered heteroaryl, aryl and (C$_1$-C$_4$)alkylaryl; wherein said alkyl, cycloalkyl, heterocycloalkyl, heteroaryl and aryl are optionally substituted with one or more substituents independently selected from R$^5$; and R$^5$ is selected from the group consisting of halogen, cyano, hydroxyl, (C$_1$-C$_4$)alkyl, halo(C$_1$-C$_4$)alkyl and halo(C$_1$-C$_4$)alkyloxy, OR$_x$, SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), R$^1$ is hydrogen or (C$_1$-C$_4$)alkyl; and R$^2$ is pyrrolidinyl, which is optionally substituted with R$^4$; and R$^4$ is selected from the group consisting of —C(O)(C$_1$-C$_4$)alkyl, and —C(O)O(C$_1$-C$_4$)alkyl; and R$^3$ is selected from the group consisting of (C$_3$-C$_6$)cycloalkyl, (4-6)membered heterocycloalkyl, and (5-6)membered heteroaryl, all of which are optionally substituted with one or more substituents independently selected from R$^5$; and R$^5$ is selected from the group consisting of halogen, cyano, hydroxyl, (C$_1$-C$_4$)alkyl, halo(C$_1$-C$_4$)alkyl and halo(C$_1$-C$_4$)alkyloxy, OR$_x$, —SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), R$^1$ is hydrogen or (C$_1$-C$_4$)alkyl; and R$^2$ is pyrrolidinyl which is optionally substituted with —C(O)(C$_1$-C$_4$)alkyl; and R$^3$ is selected from the group consisting of (C$_3$-C$_6$)cycloalkyl, (4-6)membered heterocycloalkyl, and (5-6)membered heteroaryl.

In another embodiment of the present invention in formula (I), R$^1$ is hydrogen; and R$^2$ is pyrrolidinyl substituted with —C(O)(C$_1$-C$_4$)alkyl; and R$^3$ is selected from the group consisting of (4-6)membered heterocycloalkyl, and (5-6)membered heteroaryl.

In another embodiment of the present invention in formula (I), R$^1$ is hydrogen or (C$_1$-C$_4$)alkyl; and R$^2$ is piperidinyl, which is optionally substituted with R$^4$; R$^4$ is selected from the group consisting of —C(O)(C$_1$-C$_4$)alkyl, (C$_1$-C$_4$)alkyl, —C(O)O(C$_1$-C$_6$)alkyl, —C(O)NR$_a$R$_b$ and —(C$_1$-C$_4$)alkyl-C(O)NR$_a$R$_b$; R$^3$ is selected from the group consisting of (C$_1$-C$_6$)alkyl, (C$_3$-C$_6$)cycloalkyl, (C$_1$-C$_4$)alkyl(C$_3$-C$_6$)cycloalkyl, halo(C$_1$-C$_6$)alkyl, (C$_1$-C$_6$)alkoxy, (C$_1$-C$_6$)alkyl(C$_1$-C$_6$)alkoxy, halo(C$_1$-C$_4$)alkyloxy, (4-6)membered heterocycloalkyl, (C$_1$-C$_4$)alkyl(4-6)membered heterocycloalkyl, (5-6)membered heteroaryl, (C$_1$-C$_4$)alkyl(5-6)membered heteroaryl, aryl and (C$_1$-C$_4$)alkylaryl; wherein said alkyl, cycloalkyl, heterocycloalkyl, heteroaryl and aryl are optionally substituted with one or more substituents independently selected from R$^5$; and R$^5$ is selected from the group consisting of halogen, cyano, hydroxyl, (C$_1$-C$_4$)alkyl, halo(C$_1$-C$_4$)alkyl and halo(C$_1$-C$_4$)alkyloxy, OR$_x$, SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), R$^1$ is hydrogen or (C$_1$-C$_4$)alkyl; and R$^2$ is piperidinyl, which is optionally substituted with R$^4$; and R$^4$ is selected from the group consisting of —C(O)(C$_1$-C$_4$)alkyl, and —C(O)O(C$_1$-C$_4$)alkyl; and R$^3$ is selected from the group consisting of (C$_3$-C$_6$)cycloalkyl, (4-6)membered heterocycloalkyl, and (5-6)membered heteroaryl, all of which are optionally substituted with one or more substituents independently selected from R$^5$; and R$^5$ is selected from the group consisting of halogen, cyano, hydroxyl, (C$_1$-C$_4$)alkyl, halo(C$_1$-C$_4$)alkyl and halo(C$_1$-C$_4$)alkyloxy, OR$_x$, —SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and R$_x$ consist of (C$_1$-C$_4$)alkyl, (C$_3$-C$_6$)cycloalkyl; and R$_a$ and R$_b$ are independently selected from the group consisting of hydrogen, (C$_1$-C$_4$)alkyl and halo(C$_1$-C$_4$)alkyl, or R$_a$ and R$_b$ may together with the nitrogen atom to which they are attached form a (4-6)membered heterocycloalkyl, wherein said heterocycloalkyl is optionally substituted with one or more (C$_1$-C$_4$)alkyl.

In another embodiment of the present invention in formula (I), $R^1$ is hydrogen or $(C_1-C_4)$alkyl; and $R^2$ is piperidinyl which is optionally substituted with —C(O)$(C_1-C_4)$alkyl; and $R^3$ is selected from the group consisting of $(C_3-C_6)$cycloalkyl, (4-6)membered heterocycloalkyl, and (5-6)membered heteroaryl.

In another embodiment of the present invention in formula (I), $R^1$ is hydrogen; and $R^2$ is piperidinyl substituted with —C(O)$(C_1-C_4)$alkyl; and $R^3$ is selected from the group consisting of (4-6)membered heterocycloalkyl, and (5-6)membered heteroaryl.

In another embodiment the invention provides a compound of general formula (II)

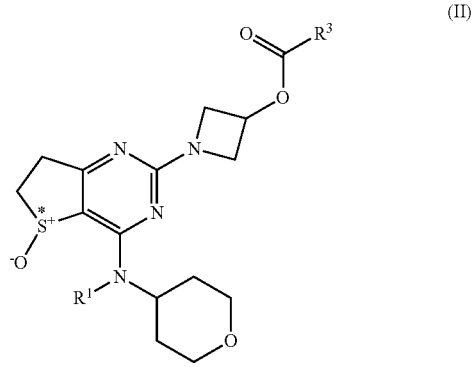

(II)

wherein
$R^1$ is hydrogen or $(C_1-C_4)$alkyl; and
wherein $R^3$ is selected from the group consisting of $(C_1-C_6)$alkyl, $(C_3-C_6)$cycloalkyl, $(C_1-C_4)$alkyl$(C_3-C_6)$cycloalkyl, halo$(C_1-C_6)$alkyl, $(C_1-C_6)$alkoxy, $(C_1-C_6)$alkyl$(C_1-C_6)$alkoxy, halo$(C_1-C_4)$alkyloxy, (4-6)membered heterocycloalkyl, $(C_1-C_4)$alkyl(4-6)membered heterocycloalkyl, (5-6)membered heteroaryl, $(C_1-C_4)$alkyl(5-6)membered heteroaryl, aryl and $(C_1-C_4)$alkylaryl; wherein said alkyl, cycloalkyl, heterocycloalkyl, heteroaryl and aryl are optionally substituted with one or more substituents independently selected from $R^5$; and
wherein $R^5$ is selected from the group consisting of halogen, cyano, hydroxyl, $(C_1-C_4)$-alkyl, halo$(C_1-C_4)$alkyl, halo$(C_1-C_4)$alkyloxy, $OR_x$, $SR_x$, —S(O)$_2R_x$, —S(O)$_2NR_aR_b$, —C(O)—$(C_1-C_6)$alkyl, —C(O)(OR$_x$), and —C(O)NR$_a$R$_b$; and
wherein $R_a$ and $R_b$ are independently selected from the group consisting of hydrogen, $(C_1-C_4)$alkyl and halo$(C_1-C_4)$alkyl, or
$R_a$ and $R_b$ may together with the nitrogen atom to which they are attached form a (4-6)membered heterocycloalkyl, wherein said heterocycloalkyl is optionally substituted with one or more $(C_1-C_4)$alkyl; and
wherein $R_x$ consist of $(C_1-C_4)$alkyl, $(C_3-C_6)$cycloalkyl; and
wherein S* represents a chiral sulphur atom; and
pharmaceutically acceptable salts, enantiomers, mixtures of enantiomers, diastereomers, mixtures of diastereomers, hydrates and solvates thereof.

In another embodiment of the present invention in formula (II), $R^1$ is hydrogen or $(C_1-C_4)$alkyl; and $R^3$ is selected from the group consisting of $(C_3-C_6)$cycloalkyl, (4-6)-membered heterocycloalkyl, (5-6)membered heteroaryl and aryl, all of which are optionally substituted with one or more substituents independently selected from $R^5$; and $R^5$ is selected from the group consisting of halogen, cyano, hydroxyl, $(C_1-C_4)$alkyl, halo$(C_1-C_4)$alkyl and halo$(C_1-C_4)$alkyloxy, $OR_x$, —$SR_x$, —$S(O)_2R_x$, —$S(O)_2NR_aR_b$, —C(O)$(C_1-C_6)$alkyl, —C(O)(OR$_x$), and —C(O)NR$_a$R$_b$; and R$_x$ consist of $(C_1-C_4)$alkyl, $(C_3-C_6)$cycloalkyl; and R$_a$ and R$_b$ are independently selected from the group consisting of hydrogen, $(C_1-C_4)$alkyl and halo$(C_1-C_4)$alkyl, or R$_a$ and R$_b$ may together with the nitrogen atom to which they are attached form a (4-6)membered heterocycloalkyl, wherein said heterocycloalkyl is optionally substituted with one or more $(C_1-C_4)$alkyl.

In another embodiment of the present invention in formula (II), $R^1$ is hydrogen or methyl; and $R^3$ is selected from the group consisting of $(C_3-C_6)$cycloalkyl, (4-6)-membered heterocycloalkyl and (5-6)membered heteroaryl.

In another embodiment of the present invention in formula (II), $R^1$ is hydrogen or methyl; and $R^3$ is (5-6)membered heteroaryl.

In another embodiment of the present invention in formula (II), $R^1$ is hydrogen; and $R^3$ is selected from the group consisting of cyclopentyl, tetrahydropyranyl, isothiazolyl and thiazolyl.

In another embodiment of the present invention in formula (II), $R^1$ is hydrogen; and $R^3$ is selected from the group consisting of isothiazolyl and thiazolyl.

In another embodiment of the present invention in formula (II), $R^1$ is methyl; and $R^3$ is selected from the group consisting of tetrahydropyranyl, isothiazolyl and thiazolyl.

In another embodiment of the present invention in formula (II), $R^1$ is methyl; and $R^3$ is selected from the group consisting of isothiazolyl and thiazolyl.

In another embodiment of the present invention, S* represents a chiral sulphur atom being in the R-configuration.

In another embodiment of the present invention, S* represents a chiral sulphur atom being in the S-configuration.

In another embodiment the invention provides a compound of general formula (IIa)

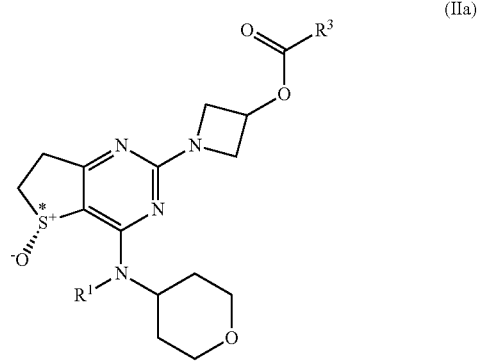

(IIa)

wherein $R^1$ is hydrogen or $(C_1-C_4)$alkyl; and
wherein $R^3$ is selected from the group consisting of $(C_1-C_6)$alkyl, $(C_3-C_6)$cycloalkyl, $(C_1-C_4)$alkyl$(C_3-C_6)$cycloalkyl, halo$(C_1-C_6)$alkyl, $(C_1-C_6)$alkoxy, $(C_1-C_6)$alkyl$(C_1-C_6)$alkoxy, halo$(C_1-C_4)$alkyloxy, (4-6)membered heterocycloalkyl, $(C_1-C_4)$alkyl(4-6)membered heterocycloalkyl, (5-6)membered heteroaryl, $(C_1-C_4)$alkyl(5-6)membered heteroaryl, aryl and $(C_1-C_4)$alkylaryl; wherein said alkyl, cycloalkyl, heterocycloalkyl, heteroaryl and aryl are optionally substituted with one or more substituents independently selected from $R^5$; and wherein $R^5$ is selected from the group consisting of halogen, cyano, hydroxyl, $(C_1-C_4)$-alkyl, halo$(C_1-C_4)$alkyl, halo$(C_1-C_4)$alkyloxy, $OR_x$, $SR_x$, —$S(O)_2R_x$, —$S(O)_2NR_aR_b$, —C(O)—$(C_1-C_6)$alkyl, —C(O)(OR$_x$), and —C(O)NR$_a$R$_b$; and wherein $R_a$ and $R_b$ are independently selected from the group consisting of hydrogen, $(C_1-C_4)$alkyl and halo$(C_1-C_4)$alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl; and wherein $R_x$ consist of $(C_1-C_4)$alkyl, $(C_3-C_6)$cycloalkyl; and pharmaceutically acceptable salts, enantiomers, mixtures of enantiomers, hydrates and solvates thereof.

In another embodiment of the present invention in formula (IIa), $R^1$ is hydrogen or $(C_1-C_4)$alkyl; and $R^3$ is selected from the group consisting of $(C_3-C_6)$cycloalkyl, (4-6)-membered heterocycloalkyl, (5-6)membered heteroaryl and aryl, all of which are optionally substituted with one or more substituents independently selected from $R^5$; and $R^5$ is selected from the group consisting of halogen, cyano, hydroxyl, $(C_1-C_4)$alkyl, halo$(C_1-C_4)$alkyl and halo$(C_1-C_4)$alkyloxy, $OR_x$, —$SR_x$, —$S(O)_2R_x$, —$S(O)_2NR_aR_b$, —C(O)$(C_1-C_6)$alkyl, —C(O)(OR$_x$), and —C(O)NR$_a$R$_b$; and $R_x$ consist of $(C_1-C_4)$alkyl, $(C_3-C_6)$cycloalkyl; and $R_a$ and $R_b$ are independently selected from the group consisting of hydrogen, $(C_1-C_4)$alkyl and halo$(C_1-C_4)$alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl.

In another embodiment of the present invention in formula (IIa), $R^1$ is hydrogen or methyl; and $R^3$ is selected from the group consisting of $(C_3-C_6)$cycloalkyl, (4-6)-membered heterocycloalkyl and (5-6)membered heteroaryl.

In another embodiment of the present invention in formula (IIa), $R^1$ is hydrogen or methyl; and $R^3$ is (5-6) membered heteroaryl.

In another embodiment of the present invention in formula (IIa), $R^1$ is hydrogen; and $R^3$ is selected from the group consisting of cyclopentyl, tetrahydropyranyl, isothiazolyl and thiazolyl.

In another embodiment of the present invention in formula (IIa), $R^1$ is hydrogen; and $R^3$ is selected from the group consisting of isothiazolyl and thiazolyl.

In another embodiment of the present invention in formula (IIa), $R^1$ is hydrogen; and $R^3$ is selected from the group consisting of 4-isothiazolyl and 4-thiazolyl.

In another embodiment of the present invention in formula (IIa), $R^1$ is methyl; and $R^3$ is selected from the group consisting of tetrahydropyranyl, isothiazolyl and thiazolyl.

In another embodiment of the present invention in formula (IIa), $R^1$ is methyl; and $R^3$ is selected from the group consisting of isothiazolyl and thiazolyl.

In another embodiment of the present invention in formula (IIa), $R^1$ is methyl; and $R^3$ is selected from the group consisting of 4-isothiazolyl and 4-thiazolyl.

In another embodiment the invention provides a compound selected from the following:

[1-[(5R)-5-Oxido-4-(tetrahydropyran-4-ylamino)-6,7-dihydrothieno[3,2-d]pyrimidin-5-ium-2-yl]azetidin-3-yl] isothiazole-4-carboxylate (Compound 004a),

[1-[(5R)-5-Oxido-4-(tetrahydropyran-4-ylamino)-6,7-dihydrothieno[3,2-d]pyrimidin-5-ium-2-yl]azetidin-3-yl] thiazole-4-carboxylate (Compound 005a),

[1-[4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009),

[1-[(5R)-4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009a),

[1-[4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010),

[1-[(5R)-4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010a);

and a pharmaceutically acceptable salt, enantiomer, mixture of enantiomers, hydrate or solvate thereof.

In another embodiment the invention provides a compound selected from the following:

[1-[(5R)-5-oxido-4-(tetrahydropyran-4-ylamino)-6,7-dihydrothieno[3,2-d]pyrimidin-5-ium-2-yl]azetidin-3-yl] cyclopentanecarboxylate

[1-[(5R)-5-oxido-4-(tetrahydropyran-4-ylamino)-6,7-dihydrothieno[3,2-d]pyrimidin-5-ium-2-yl]azetidin-3-yl] tetrahydropyran-4-carboxylate,

[1-[4-[methyl(tetrahydropyran-4-yl)amino]-5-oxido-6,7-dihydrothieno[3,2-d]pyrimidin-5-ium-2-yl]azetidin-3-yl] 3-methoxypropanoate

[1-[4-[methyl(tetrahydropyran-4-yl)amino]-5-oxido-6,7-dihydrothieno[3,2-d]pyrimidin-5-ium-2-yl]azetidin-3-yl] 3-hydroxycyclobutanecarboxylate

[1-[4-[methyl(tetrahydropyran-4-yl)amino]-5-oxido-6,7-dihydrothieno[3,2-d]pyrimidin-5-ium-2-yl]azetidin-3-yl] 3-methylsulfanylpropanoate

[1-[4-[methyl(tetrahydropyran-4-yl)amino]-5-oxido-6,7-dihydrothieno[3,2-d]pyrimidin-5-ium-2-yl]azetidin-3-yl] benzoate

[1-[4-[methyl(tetrahydropyran-4-yl)amino]-5-oxido-6,7-dihydrothieno[3,2-d]pyrimidin-5-ium-2-yl]azetidin-3-yl] 1-methylpyrazole-3-carboxylate

[1-[4-[methyl(tetrahydropyran-4-yl)amino]-5-oxido-6,7-dihydrothieno[3,2-d]pyrimidin-5-ium-2-yl]azetidin-3-yl] 1-methylpyrazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 1-methylimidazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-methyloxazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-methyloxazole-5-carboxylate

[1-[4-[methyl(tetra-hydropyran-4-yl)amino]-5-oxido-6,7-dihydrothieno[3,2-d]pyrimidin-5-ium-2-yl]azetidin-3-yl] isothiazole-5-carboxylate

[1-[4-[methyl(tetrahydropyran-4-yl)amino]-5-oxido-6,7-dihydrothieno[3,2-d]pyrimidin-5-ium-2-yl]azetidin-3-yl] tetrahydropyran-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-methylbenzoate

[1-[4-[methyl(tetrahydropyran-4-yl)amino]-5-oxido-6,7-dihydrothieno[3,2-d]pyrimidin-5-ium-2-yl]azetidin-3-yl] 3-methylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-methylbenzoate

[1-[4-[methyl(tetrahydropyran-4-yl)amino]-5-oxido-6,7-dihydrothieno[3,2-d]pyrimidin-5-ium-2-yl]azetidin-3-yl] 2-methylpyrimidine-5-carboxylate

[1-[4-[methyl(tetrahydropyran-4-yl)amino]-5-oxido-6,7-dihydrothieno[3,2-d]pyrimidin-5-ium-2-yl]azetidin-3-yl] 4-fluorobenzoate

[1-[4-[methyl(tetrahydropyran-4-yl)amino]-5-oxido-6,7-dihydrothieno[3,2-d]pyrimidin-5-ium-2-yl]azetidin-3-yl] 2-fluorobenzoate

[1-[4-[methyl(tetrahydropyran-4-yl)amino]-5-oxido-6,7-dihydrothieno[3,2-d]pyrimidin-5-ium-2-yl]azetidin-3-yl] 1-ethylpyrazole-3-carboxylate

[1-[4-[methyl(tetrahydropyran-4-yl)amino]-5-oxido-6,7-dihydrothieno[3,2-d]pyrimidin-5-ium-2-yl]azetidin-3-yl] 1,5-dimethylpyrazole-3-carboxylate

[1-[4-[methyl(tetrahydropyran-4-yl)amino]-5-oxido-6,7-dihydrothieno[3,2-d]pyrimidin-5-ium-2-yl]azetidin-3-yl] 1-ethylpyrazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-ethyloxazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 3-methylisothiazole-5-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-methylthiazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-methylthiazole-5-carboxylate

[1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate

[1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate

[1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate

[1-[4-[methyl(tetrahydropyran-4-yl)amino]-5-oxido-6,7-dihydrothieno[3,2-d]pyrimidin-5-ium-2-yl]azetidin-3-yl] tetrahydrothiopyran-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 2,6-dimethylpyridine-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 4-methoxybenzoate

[1-[4-[methyl(tetrahydropyran-4-yl)amino]-5-oxido-6,7-dihydrothieno[3,2-d]pyrimidin-5-ium-2-yl]azetidin-3-yl] 3-methoxybenzoate

[1-[4-[methyl(tetrahydropyran-4-yl)amino]-5-oxido-6,7-dihydrothieno[3,2-d]pyrimidin-5-ium-2-yl]azetidin-3-yl] 3-methylsulfonylpropanoate

[1-[4-[methyl(tetrahydropyran-4-yl)amino]-5-oxido-6,7-dihydrothieno[3,2-d]pyrimidin-5-ium-2-yl]azetidin-3-yl] 5-ethyl-1-methyl-pyrazole-3-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-ethylthiazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 3-benzoate

[1-[4-[methyl(tetrahydropyran-4-yl)amino]-5-oxido-6,7-dihydrothieno[3,2-d]pyrimidin-5-ium-2-yl]azetidin-3-yl] 4-acetylbenzoate

[1-[4-[methyl(tetrahydropyran-4-yl)amino]-5-oxido-6,7-dihydrothieno[3,2-d]pyrimidin-5-ium-2-yl]azetidin-3-yl] 1-acetylpiperidine-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 1,1-dioxothiane-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 4-(methylcarbamoyl)benzoate O1-methyl O4-[1-[4-[methyl(tetrahydropyran-4-yl)amino]-5-oxido-6,7-dihydrothieno[3,2-d]pyrimidin-5-ium-2-yl]azetidin-3-yl] piperidine-1,4-dicarboxylate

[1-[4-[methyl(tetrahydropyran-4-yl)amino]-5-oxido-6,7-dihydrothieno[3,2-d]pyrimidin-5-ium-2-yl]azetidin-3-yl] 4-(dimethylcarbamoyl)benzoate

[1-[4-[methyl(tetrahydropyran-4-yl)amino]-5-oxido-6,7-dihydrothieno[3,2-d]pyrimidin-5-ium-2-yl]azetidin-3-yl] 4-methylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 1-(dimethylcarbamoyl)piperidine-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 3-ethylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-ethylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-(methylsulfamoyl)benzoate

[1-[4-[methyl(tetrahydropyran-4-yl)amino]-5-oxido-6,7-dihydrothieno[3,2-d]pyrimidin-5-ium-2-yl]azetidin-3-yl] 3-isopropylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-isopropylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-(morpholine-4-carbonyl)benzoate

[1-[4-[methyl(tetrahydropyran-4-yl)amino]-5-oxido-6,7-dihydrothieno[3,2-d]pyrimidin-5-ium-2-yl]azetidin-3-yl] 4-cyclopentylsulfonylbenzoate

[1-[(5R)-4-[methyl(tetrahydropyran-4-yl)amino]-5-oxido-6,7-dihydrothieno[3,2-d]pyrimidin-5-ium-2-yl]azetidin-3-yl] pyridine-3-carboxylate

[1-[(5R)-4-[methyl(tetrahydropyran-4-yl)amino]-5-oxido-6,7-dihydrothieno[3,2-d]pyrimidin-5-ium-2-yl]azetidin-3-yl] 4-methylbenzoate

[1-[4-(6-oxaspiro[3.3]heptan-2-ylamino)-5-oxido-6,7-dihydrothieno[3,2-d]pyrimidin-5-ium-2-yl]azetidin-3-yl] isothiazole-4-carboxylate

[1-[4-(6-oxaspiro[3.3]heptan-2-ylamino)-5-oxido-6,7-dihydrothieno[3,2-d]pyrimidin-5-ium-2-yl]azetidin-3-yl] thiazole-4-carboxylate

[1-[4-(6-oxaspiro[3.3]heptan-2-ylamino)-5-oxido-6,7-dihydrothieno[3,2-d]pyrimidin-5-ium-2-yl]azetidin-3-yl] tetrahydropyran-4-carboxylate

[1-[(5R)-4-(6-oxaspiro[3.3]heptan-2-ylamino)-5-oxido-6,7-dihydrothieno[3,2-d]pyrimidin-5-ium-2-yl]azetidin-3-yl] isothiazole-4-carboxylate

[1-[(5S)-4-(6-oxaspiro[3.3]heptan-2-ylamino)-5-oxido-6,7-dihydrothieno[3,2-d]pyrimidin-5-ium-2-yl]azetidin-3-yl] isothiazole-4-carboxylate

[1-[(5R)-4-(6-oxaspiro[3.3]heptan-2-ylamino)-5-oxido-6,7-dihydrothieno[3,2-d]pyrimidin-5-ium-2-yl]azetidin-3-yl] thiazole-4-carboxylate

[1-[(5S)-4-(6-oxaspiro[3.3]heptan-2-ylamino)-5-oxido-6,7-dihydrothieno[3,2-d]pyrimidin-5-ium-2-yl]azetidin-3-yl] thiazole-4-carboxylate

[1-[4-[[(3S)-1-acetylpyrrolidin-3-yl]amino]-5-oxido-6,7-dihydrothieno[3,2-d]pyrimidin-5-ium-2-yl]azetidin-3-yl] isothiazole-4-carboxylate

[1-[4-[[(3S)-1-acetylpyrrolidin-3-yl]amino]-5-oxido-6,7-dihydrothieno[3,2-d]pyrimidin-5-ium-2-yl]azetidin-3-yl] thiazole-4-carboxylate

[1-[4-[[(3S)-1-acetylpyrrolidin-3-yl]amino]-5-oxido-6,7-dihydrothieno[3,2-d]pyrimidin-5-ium-2-yl]azetidin-3-yl] tetrahydropyran-4-carboxylate

[1-[4-[[(3R)-1-acetylpyrrolidin-3-yl]amino]-5-oxido-6,7-dihydrothieno[3,2-d]pyrimidin-5-ium-2-yl]azetidin-3-yl] tetrahydropyran-4-carboxylate

[1-[4-[(1-acetyl-4-piperidyl)amino]-5-oxido-6,7-dihydrothieno[3,2-d]pyrimidin-5-ium-2-yl]azetidin-3-yl] thiazole-4-carboxylate

[1-[4-[(1-acetyl-4-piperidyl)amino]-5-oxido-6,7-dihydrothieno[3,2-d]pyrimidin-5-ium-2-yl]azetidin-3-yl] tetrahydropyran-4-carboxylate, and a pharmaceutically acceptable salt, enantiomer, mixture of enantiomers, hydrate or solvate thereof.

In another embodiment the invention provides an intermediate compound of general formula (III)

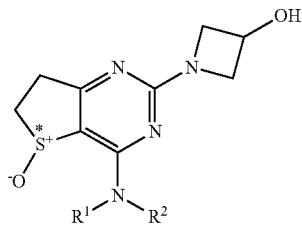

(III)

wherein R' is hydrogen or $(C_1-C_4)$alkyl; and
wherein $R^2$ is selected from the group consisting of tetrahydropyranyl, oxaspiro-heptanyl, pyrrolidinyl and piperidinyl; wherein said pyrrolidinyl and piperidinyl are optionally substituted with one or more substituents independently selected from $R^4$; and
wherein $R^4$ is selected from the group consisting of —C(O)$(C_1-C_4)$alkyl, $(C_1-C_4)$alkyl, —C(O)O$(C_1-C_6)$alkyl, —C(O)NR$_a$R$_b$ and —$(C_1-C_4)$alkyl-C(O)NR$_a$R$_b$; and
wherein R$_a$ and R$_b$ are independently selected from the group consisting of hydrogen, $(C_1-C_4)$alkyl and halo$(C_1-C_4)$alkyl, or
R$_a$ and R$_b$ may together with the nitrogen atom to which they are attached form a (4-6)membered heterocycloalkyl, wherein said heterocycloalkyl is optionally substituted with one or more $(C_1-C_4)$alkyl; and
S* represent a chiral sulphur atom; and
pharmaceutically acceptable salts, enantiomers, mixtures of enantiomers, hydrates and solvates thereof.

In another embodiment of the present invention in formula (III), $R^1$ is hydrogen or $(C_1-C_4)$alkyl; and $R^2$ is tetrahydropyranyl.

In another embodiment of the present invention in formula (III), $R^1$ is hydrogen or methyl; and $R^2$ is tetrahydropyranyl.

In another embodiment of the present invention in formula (III), $R^1$ is hydrogen; and $R^2$ is tetrahydropyranyl.

In another embodiment of the present invention in formula (III), $R^1$ is methyl; and $R^2$ is tetrahydropyranyl.

In another embodiment the invention provides an intermediate compound of general formula (III) selected from the following:

1-[(5R)-5-Oxido-4-(tetrahydropyran-4-ylamino)-6,7-dihydrothieno[3,2-d]pyrimidin-5-ium-2-yl]azetidin-3-ol (Compound 003a), 1-[4-[Methyl(tetrahydropyran-4-yl)amino]-5-oxido-6,7-dihydrothieno[3,2-d]pyrimidin-5-ium-2-yl]azetidin-3-ol (Compound 008), and 1-[(5R)-4-[Methyl(tetrahydropyran-4-yl)amino]-5-oxido-6,7-dihydrothieno[3,2-d]pyrimidin-5-ium-2-yl]azetidin-3-ol (Compound 008a).

The compounds of the invention could be obtained in crystalline form either directly by concentration from an organic solvent or by crystallisation or re-crystallisation from an organic solvent or mixture of said solvent and a co-solvent that could be organic or inorganic, such as water. The crystals could be isolated in essentially solvent-free form or as a solvate, such as a hydrate. The invention covers all crystalline modifications and forms and also mixtures thereof.

The compounds of the invention comprise asymmetrically substituted (chiral) atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, such as l-ephedrine, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. If a specific stereoisomer is desired, said compound will be synthesized by stereoselective or stereospecific methods of preparation. These methods will advantageously employ chiral pure starting materials.

Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the invention, optionally in combination with other active compounds, could be useful for the treatment of dermal diseases or conditions, in particular for the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Besides being useful for human treatment, the compounds of the present invention could also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of the invention, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

In the form of a dosage unit, the compound could be administered one or more times a day at appropriate intervals, always depending, however, on the condition of the patient, and in accordance with the prescription made by the medical practitioner. Conveniently, a dosage unit of a topical formulation contain between 0.001 mg and 1000 mg, preferably between 0.01 mg and 100 mg, such as 0.1-50 mg of a compound of the invention. Also, conveniently, a dosage unit of a topical formulation contain between 0.01 mg and 10 g mg, preferably between 0.1 mg and 1000 mg, such as 1-500 mg of a compound of formula (I).

A suitable dosage of the compound of the invention will depend, inter alia, on the age and condition of the patient, the severity of the disease to be treated and other factors well known to the practising physician. The compound could be administered either orally, parenterally or topically according to different dosing schedules, e.g. daily or with weekly intervals. In general a single dose will be in the range from 0.0001 to 10 mg/kg body weight, e.g. in the range from 0.001 to 5 mg/kg body weight. Also, in general a single dose will be in the range from 0.001 to 100 mg/kg body weight, e.g. in the range from 0.01 to 10 mg/kg body weight. The compound could be administered as a bolus (i.e. the entire daily dose is administered at once) or in divided doses two or more times a day.

In the context of topical treatment it could be more appropriate to refer to a "usage unit", which denotes unitary, i.e. a single dose which is capable of being administered to a patient, and which could be readily handled and packed, remaining as a physically and chemically stable unit dose comprising either the active material as such or a mixture of it with solid or liquid pharmaceutical diluents or carriers. A "usage unit" is capable of being administered topically to a patient in an application per square centimetre of the skin of from 0.1 mg to 50 mg and preferably from 0.2 mg to 5 mg of the final formulation in question.

It is also envisaged that in certain treatment regimes, administration with longer intervals, e.g. every other day, every week, or even with longer intervals could be beneficial.

If the treatment involves administration of another therapeutically active compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said compounds.

The administration of a compound of the present invention with one or more other active compounds could be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal or buccal administration. Topical administration of the claimed formulation is particularly suitable.

The formulations could conveniently be presented in dosage unit form and could be prepared by but not restricted to any of the methods well known in the art of pharmacy, e.g. as disclosed in Remington, The Science and Practice of Pharmacy, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration could be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils could be edible oils, such as but not restricted to e.g. cottonseed oil, sesame oil, coconut oil or peanut oil. Suitable dispersing or suspending agents for aqueous suspensions include synthetic or natural surfactants and viscosifyring agents such as but not restricted to tragacanth, alginate, acacia, dextran, sodium carboxymethylcellulose, gelatin, methylcellulose, hydroxypropylmethylcellulose, hydroxypropylcellulose, carbomers, polyvinylpyrrolidone, polysorbates, sorbitan fatty acid esters. The active ingredients could also be administered in the form of a bolus, electuary or paste.

A tablet could be made by compressing, moulding or freeze drying the active ingredient optionally with one or more accessory ingredients. Compressed tablets could be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethylcellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets could be made by moulding, in a suitable machine, a mixture of the powdered active ingredient and suitable carrier moistened with an inert liquid diluent. Freeze dried tablets could be formed in a freeze-dryer from a solution of the drug substance. A suitable filler can be included.

Formulations for rectal administration could be in the form of suppositories in which the compound of the present invention is admixed with low melting point, water soluble or insoluble solids such as cocoa butter, hydrogenated vegetable oils, polyethylene glycol or fatty acids esters of polyethylene glycols, while elixirs could be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation could contain cosolvent, solubilising agent and/or complexation agents. The formulation could be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of the invention could be presented as a sterile, solid preparation, e.g. a freeze-dried powder, which is readily dissolved in a sterile solvent immediately prior to use.

Transdermal formulations could be in the form of a plaster, patch, microneedles, liposomal or nanoparticulate delivery systems or other cutaneous formulations applied to the skin.

Formulations suitable for ophthalmic administration could be in the form of a sterile aqueous preparation of the active ingredients, which could be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, could also be used to present the active ingredient for ophthalmic administration.

Formulations suitable for topical, such as dermal, intradermal or ophthalmic administration include liquid or semi-solid preparations such as liniments, lotions, gels, applicants, sprays, foams, filmforming systems, microneedles, micro- or nano-emulsions, oil-in-water or water-in-oil emulsions such as creams, ointments or pastes; or solutions or suspensions such as drops. Compositions for ophthalmic treatment could additionally contain cyclodextrin.

For topical administration, the compound of the invention could typically be present in an amount of from 0.001 to 20% by weight of the composition, such as 0.01% to about 10%, but could also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of the invention could include one or more additional ingredients such as diluents, buffers, flavouring agents, colourant, surface active agents, thickeners, penetration enhancing agents, solubility enhancing agents preservatives, e.g. methyl hydroxybenzoate (including antioxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition could additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, O-adrenergic agents, COX-2 inhibitors, JAK inhibitors, other PDEs, salicylates, indomethacin, flufenamate, naproxen, timegadine, gold salts, penicillamine, serum cholesterol lowering agents, retinoids, zinc salts, salicylazosulfa-pyridine and calcineurin inhibitors.

Deuterated analogues. Any formula given herein is also intended to represent unlabeled forms as well as isotopically labeled forms of the compounds. For example, any hydrogen represented by "H" in any of the formulae herein is intended to represent all isotopic forms of hydrogen, e.g. $^1H$, $^2H$ or D, $^3H$. Enrichment with heavier isotopes, particularly deuterium (i.e. $^2H$ or D) could afford certain therapeutic advantages due to for example an increased metabolic skin stability or an increased, systemic, in vivo clearance. Changes that would result in reduced dosage requirements or an improvement in therapeutic index. It is understood that deuterium in this context is regarded as a substituent of a compound of the formula (I).

Isotopically-enriched compounds of formula (I) can generally be prepared by conventional techniques known to those skilled in the art or by processes analogous to those described in the accompanying Preparations and Examples using any appropriate isotopically enriched reagent in place of the non-enriched reagent previously employed.

Medical Use of the Invention

As the compounds of the invention could exhibit PDE4 inhibitory activity, the compounds could be useful as therapeutic agents for inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; acute or chronic cutaneous wound disorders; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

In one embodiment, the compounds of the present invention are considered useful for the treatment, prevention or alleviation of dermal diseases or conditions.

In another embodiment, the compounds of the present invention are considered useful for the treatment, prevention or alleviation of dermal diseases or conditions selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

In another embodiment, the compounds of the present invention are considered useful for the treatment or alleviation of atopic dermatitis.

In another embodiment, the compounds of the present invention are considered useful for the treatment or alleviation of psoriasis.

In another embodiment, the compounds of the present invention are considered useful for the treatment or alleviation of alopecia areata.

In another embodiment, the compounds of the present invention are considered useful for the treatment or alleviation of acne.

In another embodiment, the compounds of the present invention are considered useful for the treatment or alleviation of pruritis.

In another embodiment, the compounds of the present invention are considered useful for the treatment or alleviation of eczema.

Methods of Preparation

The compounds of the present invention can be prepared in a number of ways well known to those skilled in the art of synthesis. The compounds of the invention could for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

The compounds of the present invention or any intermediate could be purified if required using standard methods well known to a synthetic organist chemist, e.g. methods described in "Purification of Laboratory Chemicals", $6^{th}$, ed. 2009, W. Amarego and C. Chai, Butterworth-Heinemann.

Starting materials are either known or commercially available compounds or can be prepared by routine synthetic methods well known to a person skilled in the art.

$^1$H nuclear magnetic resonance (NMR) spectra were recorded at 300 or 600 MHz unless otherwise specified. Chemical shift values (δ, in ppm) are quoted relative to internal tetramethylsilane (δ=0.00) standards. The value of a multiplet, either defined doublet (d), triplet (t), quartet (q) or (m) at the approximate midpoint is given unless a range is quoted. (s) indicates a singlet. The organic solvents used were usually anhydrous. Chromatography was performed on Merck silica gel 60 (0.040-0-063 mm). The solvent ratios indicated refer to v:v unless otherwise noted. All NMR spectra are recorded in DMSO-$d_6$ unless another solvent is stated.

Analytical UPLC/MS

Analytical UPLC/MS is performed on a Waters Acquity UPLC-system and SQD-MS. Column: Waters Acquity HSS T3 1.8 µm, 2.1×50 mm; solvent system: A=10 mM Ammonium acetate in water+0.1% HCOOH and B=acetonitrile+0.1% HCOOH; flow rate=1.2 mL/min; method (1.4 min): Linear gradient method from 5% B to 95% B over 0.9 minutes then 95% B for 0.3 minutes. Column temperature is 60° C.

Preparative Acidic Purification HPLC/MS:

Preparative HPLC/MS was performed on a Waters AutoPurification system with a Waters SQD2 mass spectrometer. This includes three steps, pre-analysis, preparative purification and re-analysis on the purified compound.

Solvent: A=0.1% formic acid and solvent B=acetonitrile with 0.1% formic acid.

Analytical Pre-Analysis Using the Following Method:
Column: Waters SUNFIRE C-18, 100 mm×4.6 mm, 5 µm
Flow rate=1.2 mL/min. (method 10 min)
Method: Linear gradient method going from 10% B to 95% B in 6.5 minutes and staying at 95% B for another 1.5 minutes to obtain the retention time of the compounds provides the following four different preparative gradient methods:

Preparative Methods:
Column: Waters SUNFIRE C-18, 100 mm×19 mm, 5 µm
Flow rate=20 mL/min. (method 8 min)
0-3 min: 5% B for 2 minutes followed by a linear gradient method going from 5% B to 35% B in 3 minutes and going to 100% B and staying at 100% B for another 1.4 minutes.
3.01-5 min: 15% B for 1 minutes followed by a linear gradient method going from 15% B to 55% B in 4 minutes and going to 100% B and staying at 100% B for another 1.4 minutes.
5.01-7.5 min: 30% B for 1 minutes followed by a linear gradient method going from 30% B to 70% B in 4 minutes and going to 100% B and staying at 100% B for another 1.4 minutes.
7.51-10 min: 50% B for 1 minutes followed by a linear gradient method going from 50% B to 100% B in 4 minutes and staying at 100% B for another 1.5 minutes.

The fractions were collected based on ion traces of relevant ions and PDA signal (240-400 nm).

Re-Analysis Method for Fractions:
Column: Waters Xselect C18; 50×3.0 mm 5 µm
Flow rate=1.2 mL/min. (method 5 min)
Method: Linear gradient method going from 10% B to 95% B in 3 minutes and staying at 95% B for another 0.5 min.

Instruments:
Waters 2767 Sample Manager
Waters 2545 Binary Gradient Module
Waters SFO System Fluidics Organizer
Waters 515 HPLC Pump
Waters 2998 Photodiode Array Detector
Waters SQDetector 2

Preparative Basic Purification HPLC/MS:
Preparative HPLC/MS was performed on a Waters AutoPurification system with a Waters SQD2 mass spectrometer. This includes three steps, pre-analysis, preparative purification and re-analysis on the purified compound.
Solvent: A=50 mM Ammonium hydrogen carbonate and solvent B=acetonitrile Analytical Pre-Analysis Using the Following Method:
Column: Waters XBridge C-18, 100 mm×4.6 mm, 5 µm
Flow rate=1.2 mL/min. (method 10 min)
Method: Linear gradient method going from 10% B to 95% B in 6.5 minutes and staying at 95% B for another 1.5 minutes to obtain the retention time of the compounds provides the following four different preparative gradient methods:

Preparative Methods:
Column: Waters XBridge C-18, 100 mm×19 mm, 5 µm
Flow rate=20 mL/min. (method 8 min)
0-3 min: 5% B for 2 minutes followed by a linear gradient method going from 5% B to 35% B in 3 minutes and going to 100% B and staying at 100% B for another 1.4 minutes.
3.01-5 min: 15% B for 1 minutes followed by a linear gradient method going from 15% B to 55% B in 4 minutes and going to 100% B and staying at 100% B for another 1.4 minutes.
5.01-7.5 min: 30% B for 1 minutes followed by a linear gradient method going from 30% B to 70% B in 4 minutes and going to 100% B and staying at 100% B for another 1.4 minutes.

7.51-10 min: 50% B for 1 minutes followed by a linear gradient method going from 50% B to 100% B in 4 minutes and staying at 100% B for another 1.5 minutes.

The fractions were collected based on ion traces of relevant ions and PDA signal (240-400 nm).

Re-Analysis Method for Fractions:

Column: Waters Xselect C18; 50×3.0 mm 5 μm

Flow rate=1.2 mL/min. (method 5 min)

Method: Linear gradient method going from 10% B to 95% B in 3 minutes and staying at 95% B for another 0.5 min.

Instruments:

Waters 2767 Sample Manager

Waters 2545 Binary Gradient Module

Waters SFO System Fluidics Organizer

Waters 515 HPLC Pump

Waters 2998 Photodiode Array Detector

Waters SQDetector 2

LCMS Method "XE Metode 7 CM"

A quality check was performed on a Waters LCT Premier MS instrument and a Waters Aquity UPLC.

Column: Waters Aquity UPLC HSS T3 1.8 μm, 2.1×50 mm, at 40° C.

Solvents: A=10 mM ammonium acetate+0.1% HCOOH, B=MeCN+0.1% HCOOH.

Flow: 0.7 ml/min. Injection volume 2 μl. UV detection range 240-400 nm.

Gradient:

| Time | % A | % B |
| --- | --- | --- |
| 0.00 min | 99 | 1 |
| 0.50 min | 94 | 6 |
| 1.00 min | 94 | 6 |
| 2.60 min | 5 | 95 |
| 3.80 min | 5 | 95 |
| 3.81 min | 99 | 1 |
| 4.80 min | 99 | 1 |

The MW confirmation and purity was extracted and checked with OpenLynx.

The following abbreviations have been used throughout:

Cpd Compound
DCE 1,2-dichloroethane
DCM dichloromethane
DIPEA N,N-diisopropylethylamine
DMAP N,N-dimethylpyridin-4-amine
DMF N,N-dimethylformamide
DMSO dimethylsulfoxide
EDAC (3-dimethylamino-propyl)-ethyl-carbodiimide hydrochloride
EtOAc ethyl acetate
EtOH ethanol
Ex. Example
Me methyl
MeCN acetonitrile
MeOH methanol
HPLC high performance liquid chromatography
NMR nuclear magnetic resonance
ee enantiomeric excess (optical purity)
PG protecting group
Rt Retention time
SFC supercritical fluid chromatography
TBME tert-Butyl methyl ether
THF tetrahydrofuran
TEA triethylamine General Methods Compounds of the invention may be prepared according to the following non-limiting general methods and examples:

Scheme 1 Synthesis of a compound of general formula (I), wherein $R^1$, $R^2$, and $R^3$ are as previously defined

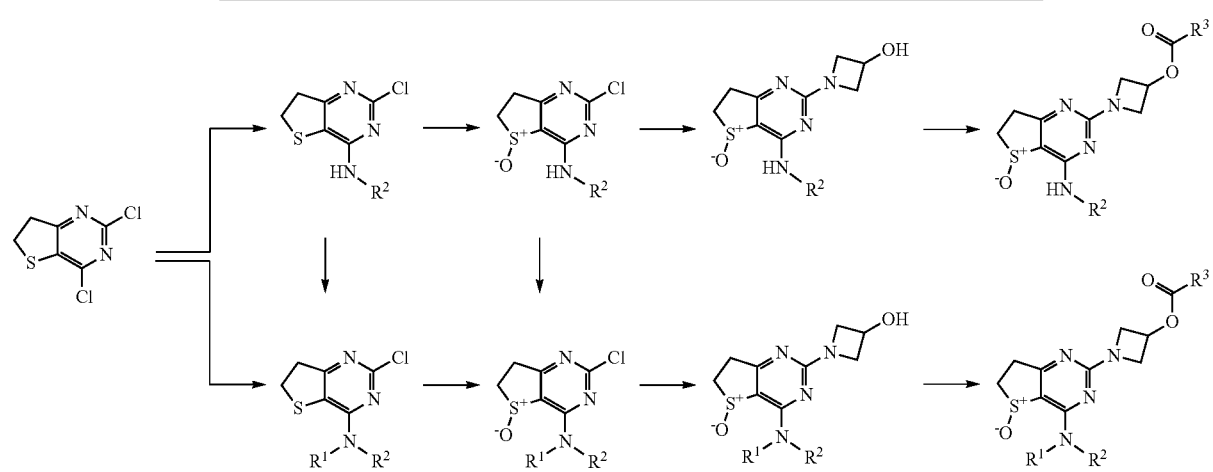

Scheme 2 Synthesis of a compound of general formula (II), wherein R¹ and R³ are as previously defined
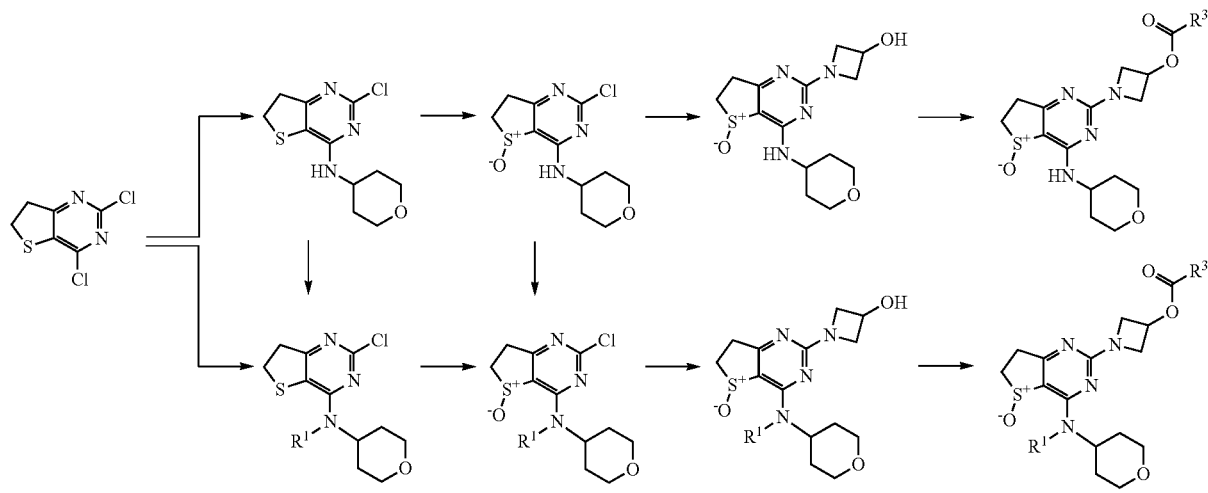
Scheme 3 Synthesis of a compound of general formula (IIa), wherein R¹ and R³ are as previously defined
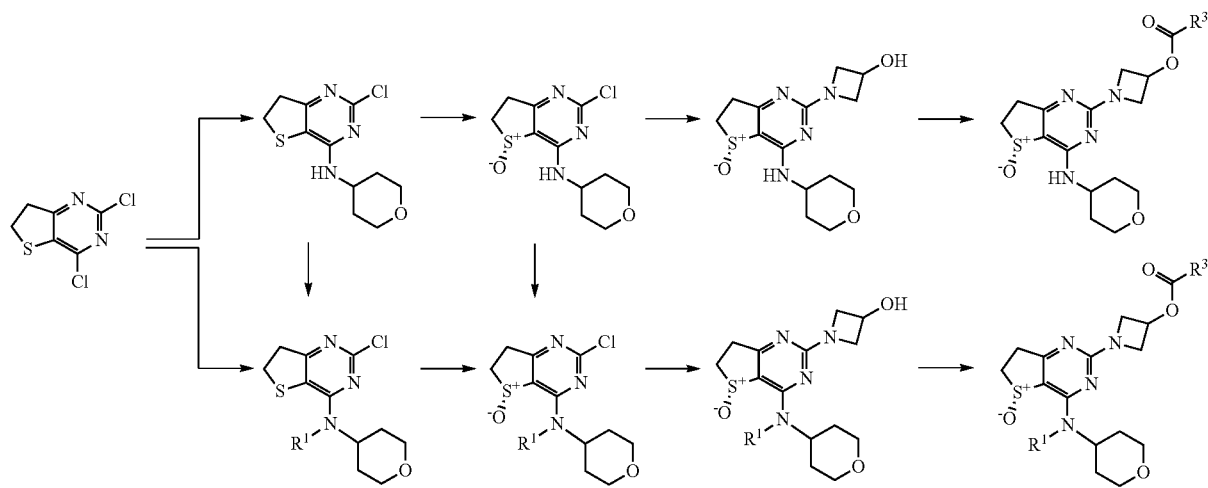
Scheme 4 Synthesis of a compound of general formula (II), wherein R¹ is hydrogen or methyl and R³ is as previously defined
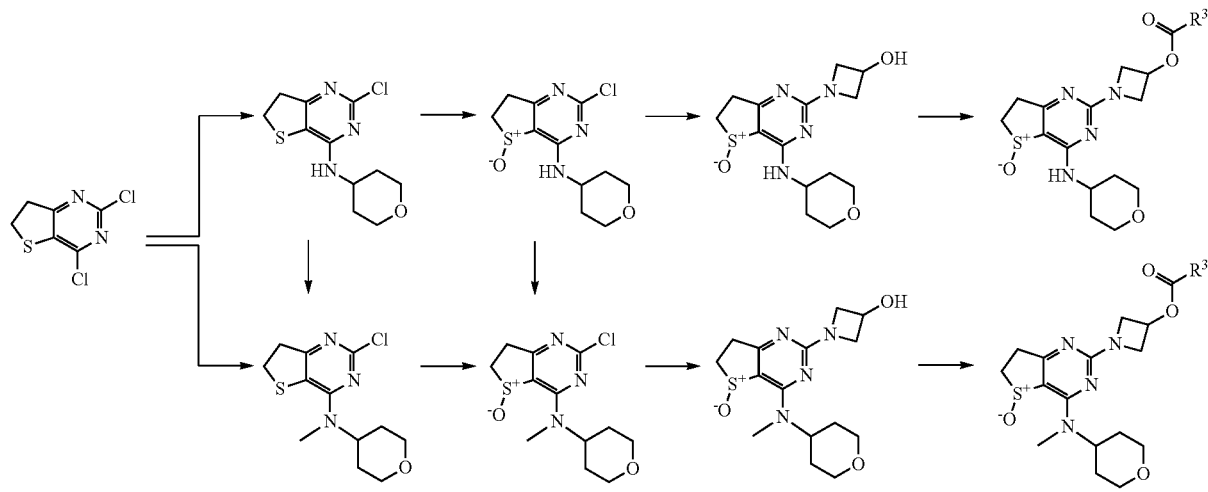

Scheme 5 Synthesis of a compound of general formula (IIa) wherein $R^1$ is hydrogen or methyl and $R^3$ is as previously defined

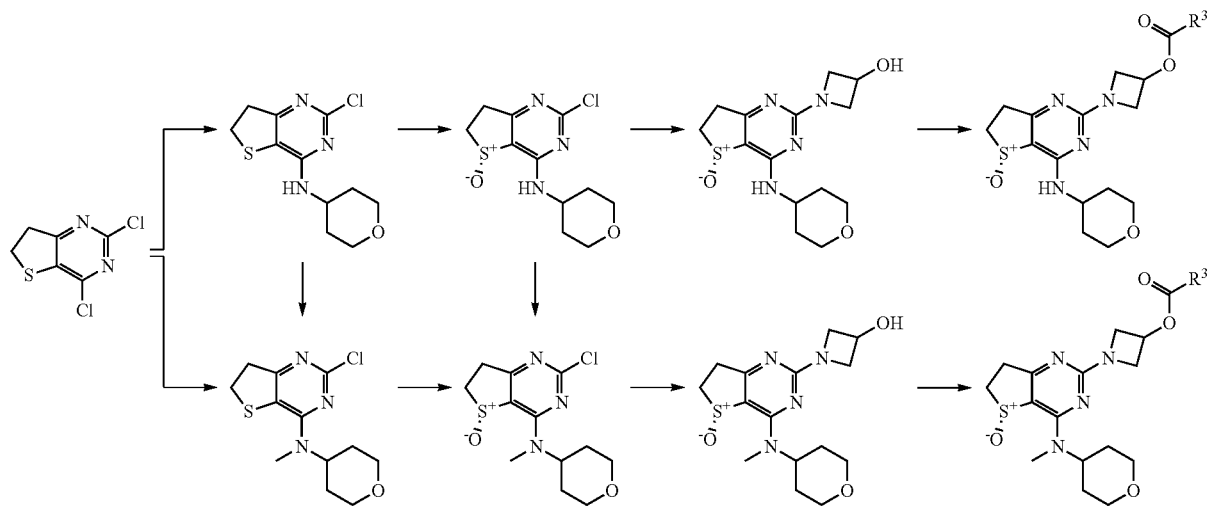

PREPARATIONS AND EXAMPLES

Preparation 1

2-Chloro-N-tetrahydropyran-4-yl-6,7-dihydrothieno[3,2-d]pyrimidin-4-amine (Compound 001)

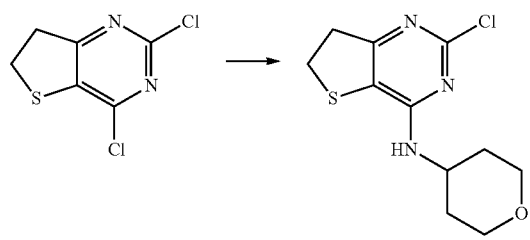

001

DIPEA (33.6 mL, 193 mmol) and tetrahydropyran-4-amine (11.7 g, 116 mmol) was added to a suspension of 2,4-dichloro-6,7-dihydrothieno[3,2-d]pyrimidine (20.0 g, 96.6 mmol) in DMF (50 mL). The mixture was stirred at 100° C. for 1 hour before it cooled to room temperature and poured into water (600 mL). The suspension was then stirred at room temperature for 10 minutes. The precipitate was filtered off, washed twice with water (2×100 mL) and tert-butyl methyl ether (2×20 mL). The solid material was dried under reduced pressure, before it was re-dissolved in a warm toluene:DCM (2:1) solution (300 mL). The mixture was concentrated to approximately 100 mL and left to stand for 1 hour at room temperature. The formed precipitate was filtered off, washed with toluene (20 mL) and dried under reduced pressure. The title compound was obtained as off-white solid material.

$^1$H NMR (DMSO-d6) δ: 7.14 (d, J=7.8 Hz, 1H), 4.21-3.99 (m, 1H), 3.95-3.77 (m, 2H), 3.46-3.33 (m, 4H), 3.14 (td, J=8.2, 1.1 Hz, 2H), 1.81-1.68 (m, 2H), 1.67-1.48 (m, 2H).

Preparation 2

2-Chloro-5-oxido-N-tetrahydropyran-4-yl-6,7-dihydrothieno[3,2-d]pyrimidin-5-ium-4-amine (Compound 002)

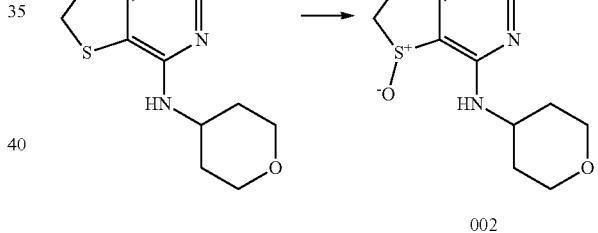

002

2-Chloro-N-tetrahydropyran-4-yl-6,7-dihydrothieno[3,2-d]pyrimidin-4-amine (3.36 g, 12.4 mmol) was dissolved in acetic acid (12.4 mL). Hydrogen peroxide (30% aqueous solution, 6.18 mL, 60.5 mmol) was added and the solution was stirred at room temperature for 1 hour before it was diluted with water (5 mL) and extracted four times with DCM (4×20 mL). The combined organic phases was dried over MgSO$_4$, filtered and evaporated to dryness under reduced pressure. The obtained solid material was suspended in diethyl ether (10 mL) and the mixture was stirred at room temperature for 10 minutes. The solid material was then filtered off, washed with diethyl ether (10 mL) and dried. The title compound was obtained as off-white solid material.

$^1$H NMR (DMSO-d6) δ: 8.59 (d, J=7.7 Hz, 1H), 4.35-4.11 (m, 1H), 3.97-3.79 (m, 2H), 3.59 (dt, J=17.5, 7.7 Hz, 1H), 3.48-3.22 (m, 3H), 3.21-2.94 (m, 2H), 1.84-1.54 (m, 4H).

Preparation 3

(5R)-2-Chloro-5-oxido-N-tetrahydropyran-4-yl-6,7-dihydrothieno[3,2-d]pyrimidin-5-ium-4-amine (Compound 002a)

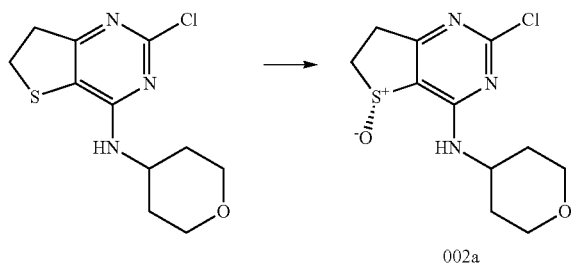

A tube containing a suspension of 2-chloro-N-tetrahydropyran-4-yl-6,7-dihydrothieno-[3,2-d]pyrimidin-4-amine (20.11 g, 74.00 mmol), (S) (−)-1,1'-binaphtol (2.12 g, 7.40 mmol), titanium tetraisopropoxide (1.1 mL, 3.7 mmol) and water (1.33 mL, 74.00 mmol) in DCM (111 mL) was flushed with argon and sealed. The mixture was stirred at room temperature for 1 hour and then cooled in a water bath before tert-butyl hydroperoxide (70% aqueous solution, 11.1 mL, 81.4 mmol) was added. After 30 minutes at room temperature the mixture was concentrated in vacuo, dissolved in hot (50° C.) MeOH (750 mL), filtered twice through a pad of celite, concentrated to approximately 200 mL. Precipitation was observed. EtOH (200 mL) was added. The mixture was concentrated in vacuo to approximately 200 mL and left for 1 hour. The formed crystals were filtered off, washed twice with EtOH (2×25 mL) and dried under reduced pressure. The title compound was obtained as pale yellowish solid.

$^1$H NMR (DMSO-d6) δ: 8.59 (d, J=7.7 Hz, 1H), 4.30-4.13 (m, 1H), 3.94-3.81 (m, 2H), 3.66-3.51 (m, 1H), 3.45-3.32 (m, 3H), 3.22-2.97 (m, 2H), 1.82-1.55 (m, 4H).

Chiral HPLC analysis: ee>98%.

The absolute configuration was assigned on the basis of X-ray structure analysis.

Preparation 4

(5S)-2-Chloro-5-oxido-N-tetrahydropyran-4-yl-6,7-dihydrothieno[3,2-d]pyrimidin-5-ium-4-amine (Compound 002b)

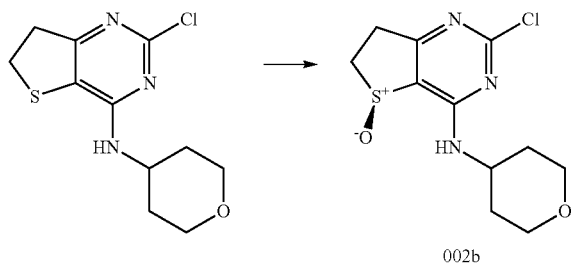

A tube containing a suspension of 2-chloro-N-tetrahydropyran-4-yl-6,7-dihydrothieno-[3,2-d]pyrimidin-4-amine (559 mg, 2.06 mmol), (R) (+)-1,1'-binaphtol (59.0 mg, 0.206 mmol), titanium tetraisopropoxide (0.030 mL, 0.103 mmol) and water (0.0371 mL, 2.06 mmol) in DCM (3.1 mL) was flushed with argon and sealed. The mixture was stirred at room temperature for 1 hour and then cooled in a water bath before tert-butyl hydroperoxide (70% aqueous solution, 0.310 mL, 2.26 mmol) was added. After 45 minutes at room temperature additional tert-butyl hydroperoxide (70% aqueous solution, 0.0434 mL, 0.452 mmol) was added and the mixture was stirred at room temperature for 1 hour before it was concentrated in vacuo, suspended in EtOH (5 mL), stirred at room temperature for 10 minutes. The solid was filtered off, washed twice with EtOH (2×1 mL) and dried under reduced pressure. The title compound was obtained as pale yellowish solid.

$^1$H NMR (DMSO-d6) δ: 8.59 (d, J=7.7 Hz, 1H), 4.22 (d, J=11.1 Hz, 1H), 3.95-3.81 (m, 2H), 3.59 (dt, J=17.5, 7.7 Hz, 1H), 3.45-3.25 (m, 3H), 3.21-2.98 (m, 2H), 1.80-1.56 (m, 4H).

Chiral HPLC analysis; ee>98%.

Preparation 5

1-[(5R)-5-Oxido-4-(tetrahydropyran-4-ylamino)-6,7-dihydrothieno[3,2-d]pyrimidin-5-ium-2-yl]azetidin-3-ol (Compound 003a)

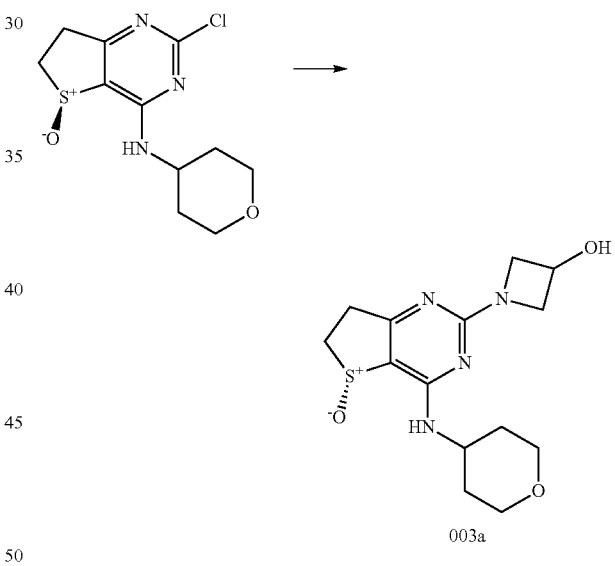

A mixture of (5R)-2-chloro-5-oxido-N-tetrahydropyran-4-yl-6,7-dihydrothieno[3,2-d]pyrimidin-5-ium-4-amine (1.00 g, 3.48 mmol), azetidin-3-ol hydrochloride (495 mg, 4.52 mmol) and DIPEA (1.21 mL, 6.95 mmol) in DMF (10 mL) was stirred at room temperature overnight. The formed precipitate was filtered off and washed with MeCN (6 mL). Freeze drying afforded the title compound as off-white solid material.

$^1$H NMR (DMSO-d6) δ: 7.55 (d, J=7.6 Hz, 1H), 5.71-5.59 (m, 1H), 4.57-4.45 (m, 1H), 4.25-4.11 (m, 3H), 3.93-3.83 (m, 2H), 3.79-3.71 (m, 2H), 3.43-3.33 (m, 2H), 3.30 (m, 1H), 3.19 (dt, J=13.6, 8.6 Hz, 1H), 2.93 (ddd, J=17.1, 8.3, 1.6 Hz, 1H), 2.87 (ddd, J=13.6, 7.4, 1.6 Hz, 1H), 1.82-1.71 (m, 2H), 1.67-1.54 (m, 2H).

HPLC-Retention time (XE Metode 7 CM): 1.49 minutes.
Detected "M+1"-mass: 325.13.

Example 1

[1-[(5R)-5-Oxido-4-(tetrahydropyran-4-ylamino)-6,7-dihydrothieno[3,2-d]pyrimidin-5-ium-2-yl]azetidin-3-yl] isothiazole-4-carboxylate (Compound 004a)

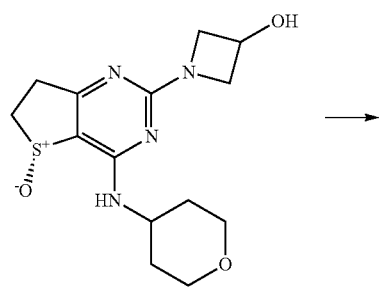

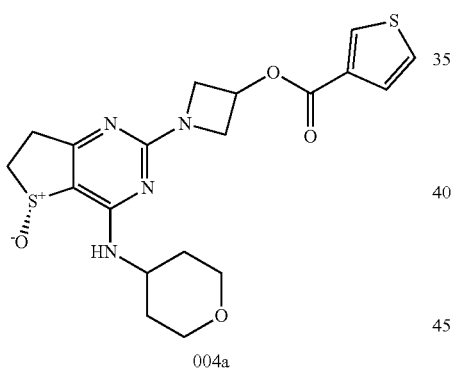

004a

A mixture of 1-[(5R)-5-oxido-4-(tetrahydropyran-4-ylamino)-6,7-dihydrothieno[3,2-d]pyrimidin-5-ium-2-yl]azetidin-3-ol (50 mg, 0.154 mmol), 4-isothiazolecarboxylic acid (29.9 mg, 0.231 mmol), DMAP (3.8 mg, 0.031 mmol) and EDAC (44.3 mg, 0.231 mmol) in DCM (2 mL) was shaken in a sealed vial at 50° C. for 1 hour. Prep-HPLC purification (acidic) afforded the title compound as off-white solid.

$^1$H NMR (Chloroform-d) δ: 9.36 (s, 1H), 8.94 (s, 1H), 6.37 (d, J=7.3 Hz, 1H), 5.52 (tt, J=6.6, 4.1 Hz, 1H), 4.58 (ddd, J=10.7, 6.6, 1.4 Hz, 2H), 4.39-4.17 (m, 3H), 4.08-3.94 (m, 2H), 3.66 (dt, J=17.2, 7.8 Hz, 1H), 3.54-3.45 (m, 2H), 3.40 (dt, J=13.5, 8.1 Hz, 1H), 3.18-3.05 (m, 2H), 1.99-1.89 (m, 2H), 1.71 (dtd, J=12.9, 11.5, 4.5 Hz, 1H), 1.62 (dtd, J=13.0, 11.5, 4.6 Hz, 1H)

HPLC-Retention time (XE Metode 7 CM): 1.81 minutes.

Detected "M+1"-mass: 436.10.

Example 2

[1-[(5R)-5-Oxido-4-(tetrahydropyran-4-ylamino)-6,7-dihydrothieno[3,2-d]pyrimidin-5-ium-2-yl]azetidin-3-yl] thiazole-4-carboxylate (Compound 005a)

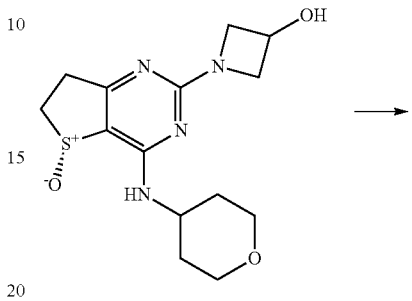

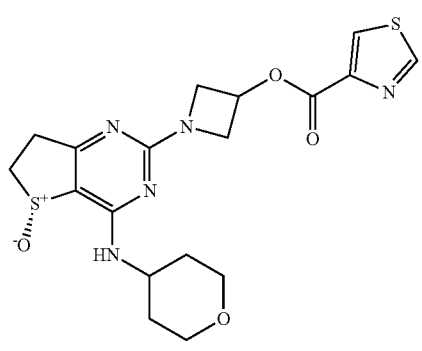

005a

A suspension of 1-[(5R)-5-oxido-4-(tetrahydropyran-4-ylamino)-6,7-dihydrothieno-[3,2-d]pyrimidin-5-ium-2-yl] azetidin-3-ol (467 mg, 1.44 mmol), 4-thiazolecarboxylic acid (242 mg, 1.87 mmol), DMAP (17.6 mg, 0.144 mmol) and EDAC (304 mg, 1.58 mmol) in DCM (10 mL) and DMF (5 mL) was stirred in a sealed vial at room temperature for 30 minutes and then for 5 minutes at 50° C. Prep-HPLC purification (acidic) afforded the title compound.

$^1$H NMR (DMSO-d6) δ: 9.21 (d, J=2.0 Hz, 1H), 8.73 (d, J=1.9 Hz, 1H), 7.66 (d, J=7.6 Hz, 1H), 5.47 (tt, J=6.6, 3.9 Hz, 1H), 4.53-4.40 (m, 2H), 4.25-4.14 (m, 1H), 4.14-4.04 (m, 2H), 3.92-3.83 (m, 2H), 3.47-3.35 (m, 3H), 3.22 (dt, J=13.6, 8.5 Hz, 1H), 2.97 (ddd, J=17.1, 8.3, 1.6 Hz, 1H), 2.93-2.86 (m, 1H), 1.82-1.73 (m, 2H), 1.69-1.55 (m, 2H).

HPLC-Retention time (XE Metode 7 CM): 1.71 minutes.

Detected "M+1"-mass: 436.11.

Preparation 6

2-Chloro-N-methyl-N-tetrahydropyran-4-yl-6,7-dihydrothieno[3,2-d]pyrimidin-4-amine (Compound 006)

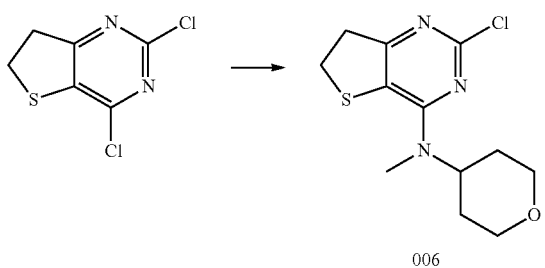 [SMILES: Clc1nc(Cl)c2c(n1)CCS2 ; CN(c1nc(Cl)nc2c1SCC2)C1CCOCC1]

To a suspension of 2,4-dichloro-6,7-dihydrothieno[3,2-d]pyrimidine (545 mg, 2.50 mmol) in ethanol (2.50 mL) was added DIPEA (0.640 mL, 3.75 mmol) and N-methyltetrahydropyran-4-amine (403 mg, 3.50 mmol). The pale yellow suspension was stirred at room temperature for 4 hours before it was heated to 50° C. for 1½ hour and then left to stir at room temperature overnight. The mixture was concentrated in vacuo. Aqueous sodium chloride solution (15 mL) was added and mixture was extracted twice with EtOAc (2×15 mL). The organic phases was washing with brine (15 mL), dried over sodium sulfate, filtered and evaporated to dryness under reduced pressure. Freeze drying afforded the title compound as pale yellow solid.

$^1$H NMR (Chloroform-d) δ: 4.59-4.43 (m, 1H), 4.10-3.99 (m, 2H), 3.57-3.43 (m, 2H), 3.30-3.16 (m, 4H), 3.07 (s, 3H), 2.02-1.81 (m, 2H), 1.72-1.62 (m, 2H).

Preparation 7

2-Chloro-N-methyl-5-oxido-N-tetrahydropyran-4-yl-6,7-dihydrothieno[3,2-d]pyrimidin-5-ium-4-amine (Compound 007)

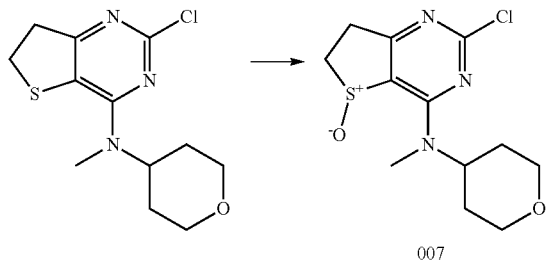

2-Chloro-N-methyl-N-tetrahydropyran-4-yl-6,7-dihydrothieno[3,2-d]pyrimidin-4-amine (200 mg, 0.700 mmol) was dissolved in acetic acid (1.0 mL). Hydrogen peroxide (50% aqueous solution, 0.0472 mL, 0.770 mmol) was added and the mixture was stirred at room temperature for 1 hour. NaI (0.5 mg, 0.003 mmol) was added in order to destroy excess hydrogen peroxide before the reaction mixture was evaporated to dryness. Prep-HPLC purification afforded the title compound.

$^1$H NMR (DMSO-d6) δ: 4.99-4.69 (m, 1H), 4.11-3.89 (m, 2H), 3.73-3.56 (m, 1H), 3.49-3.06 (m, 8H), 2.00-1.79 (m, 2H), 1.63 (t, J=15.0 Hz, 2H).

Preparation 8

(5R)-2-Chloro-N-methyl-5-oxido-N-tetrahydropyran-4-yl-6,7-dihydrothieno[3,2-d]pyrimidin-5-ium-4-amine (Compound 007a)

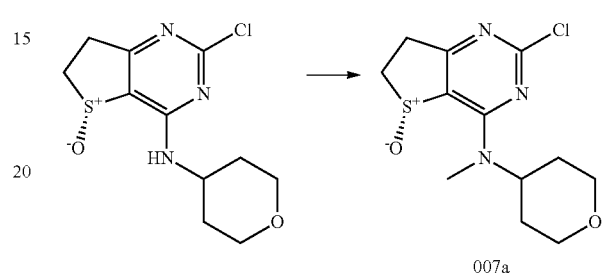

A suspension of (5R)-2-chloro-5-oxido-N-tetrahydropyran-4-yl-6,7-dihydrothieno[3,2-d]pyrimidin-5-ium-4-amine (26.5 g, 90.2 mmol) in MeCN (280 mL) was under an argon atmosphere cooled in an ice bath. Water (2.80 mL, 153 mmol), Cs$_2$CO$_3$ (50.0 g, 153 mmol) and methyl iodide (50.7 mL, 812 mmol) was added. The ice bath was removed and the mixture was stirred over night at room temperature. The crude was poured into a sat. aq. ammonium chloride solution (280 mL) and extracted with EtOAc (3×450 mL). The combined organic phases were washed with brine (280 mL) and dried over sodium sulfate. Column chromatography (ethyl acetate/heptane 1:3, R$_f$=0.25) afforded a solid to which an 1:1 mixture of EtOAc/diisopropyl ether (50 mL) was added. The suspension was stirred for 15 min. before filtration and washings with 1:1 mixtures of EtOAc/diisopropyl ether gave the title compound.

$^1$H NMR (CD$_3$OD) δ: 5.11-4.91 (m, 2H), 4.54 (s, 3H), 4.12-4.00 (m, 2H), 3.75 (ddd, J=18.0, 8.7, 7.6 Hz, 1H), 3.57 (td, J=11.9, 2.1 Hz, 2H), 3.51-3.36 (m, 1H), 3.28-3.21 (m, 1H), 2.11-1.91 (m, 2H), 1.72 (t, J=14.2 Hz, 2H).

Preparation 9

1-[4-[Methyl(tetrahydropyran-4-yl)amino]-5-oxido-6,7-dihydrothieno[3,2-d]pyrimidin-5-ium-2-yl]azetidin-3-ol (Compound 008)

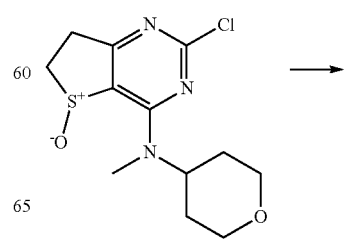

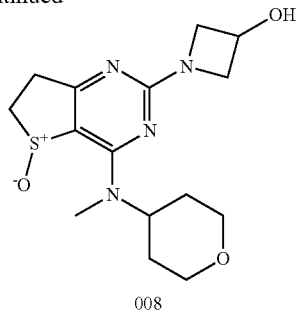

008

DIPEA (2.89 mL, 16.6 mmol) and azetidin-3-ol hydrochloride (399 mg, 3.65 mmol) was added to a solution of 2-chloro-N-methyl-5-oxido-N-tetrahydropyran-4-yl-6,7-dihydrothieno[3,2-d]pyrimidin-5-ium-4-amine (1.00 g, 3.31 mmol) in DMF (20 mL). The mixture was stirred at room temperature over night before it was concentrated in vacuo. Prep HPLC purification (basic) afforded the title compound.

$^1$H NMR (DMSO-d6) δ: 5.68 (d, J=6.4 Hz, 1H), 4.93-4.73 (m, 1H), 4.59-4.48 (m, 1H), 4.27-4.17 (m, 2H), 3.96 (dt, J=10.2, 4.5 Hz, 2H), 3.76 (dd, J=9.7, 4.5 Hz, 2H), 3.48-3.34 (m, 3H), 3.22-3.16 (m, 1H), 3.15 (s, 3H), 3.07-2.93 (m, 2H), 1.90-1.78 (m, 2H), 1.67-1.59 (m, 1H), 1.59-1.53 (m, 1H).

HPLC-Retention time (XE Metode 7 CM): 1.57 minutes.
Detected "M+1"-mass: 339.14.

Preparation 10

1-[(5R)-4-[Methyl(tetrahydropyran-4-yl)amino]-5-oxido-6,7-dihydrothieno[3,2-d]pyrimidin-5-ium-2-yl]azetidin-3-ol (Compound 008a)

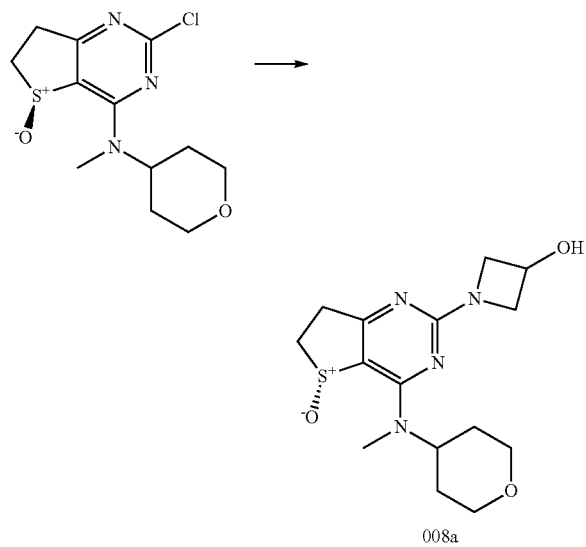

008a

A mixture of (5R)-2-chloro-N-methyl-5-oxido-N-tetrahydropyran-4-yl-6,7-dihydrothieno[3,2-d]pyrimidin-5-ium-4-amine (4.00 g, 13.3 mmol), azetidin-3-ol hydrochloride (1.89 g, 17.2 mmol) and Cs$_2$CO$_3$ (5.61 g, 17.2 mmol) in MeCN (50 mL) was stirred at room temperature for 4 hours. The mixture was filtered and subsequently concentrated in vacuo. The residue was taken up in DCM (50 mL). The precipitate was filtered off and the filtrate was concentrated in vacuo, giving the crude product. Column chromatography (MeOH/ethyl acetate 1:10, R$_f$=0.28) afforded the title compound.

$^1$H NMR (DMSO-d6) δ: 5.68 (s, 1H), 4.94-4.73 (m, 1H), 4.59-4.46 (m, 1H), 4.30-4.12 (m, 2H), 4.00-3.91 (m, 2H), 3.76 (dd, J=9.9, 4.5 Hz, 2H), 3.49-3.35 (m, 3H), 3.23-3.11 (m, 4H), 3.04-2.94 (m, 2H), 1.89-1.78 (m, 2H), 1.67-1.60 (m, 1H), 1.60-1.53 (m, 1H).

HPLC-Retention time (XE Metode 7 CM): 1.57 minutes.
Detected "M+1"-mass: 339.14.

Example 3

[1-[4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009)

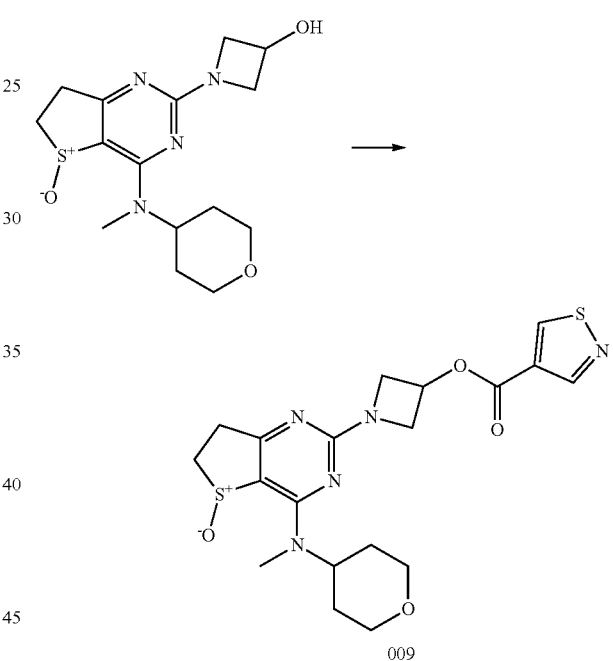

009

To a solution of 1-[4-[methyl(tetrahydropyran-4-yl)amino]-5-oxido-6,7-dihydrothieno[3,2-d]pyrimidin-5-ium-2-yl]azetidin-3-ol (5.0 mg, 15 μmol) in DCE (0.2 ML) was added solutions of 4-isothiazolecarboxylic acid (3.6 mg in 0.2 mL DCE, 28 μmol), DMAP (3.4 mg in 0.1 mL DCE, 28 μmol) and EDAC (5.3 mg in 0.2 mL DCE, 28 μmol). The mixture was shaken at 50° C. for 1 hour before it was concentrated in vacuo. Prep HPLC purification (acidic) afforded the title compound.

$^1$H NMR (DMSO-d6) δ: 9.81 (s, 1H), 9.00 (s, 1H), 5.53-5.44 (m, 1H), 4.93-4.79 (m, 1H), 4.48 (dd, J=10.4, 6.7 Hz, 2H), 4.16 (dd, J=10.7, 3.8 Hz, 2H), 4.01-3.93 (m, 2H), 3.53-3.45 (m, 1H), 3.43-3.37 (m, 2H), 3.25-3.20 (m, 1H), 3.19 (s, 3H), 3.10-2.97 (m, 2H), 1.92-1.79 (m, 2H), 1.69-1.54 (m, 2H).

HPLC-Retention time (XE Metode 7 CM): 1.88 minutes.
Detected "M+1"-mass: 450.12.

Example 4

[1-[(5R)-4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009a)

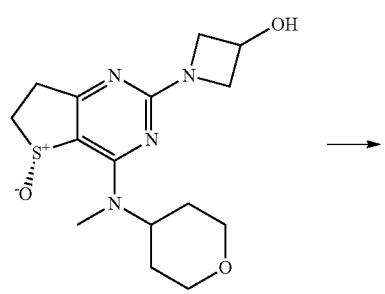

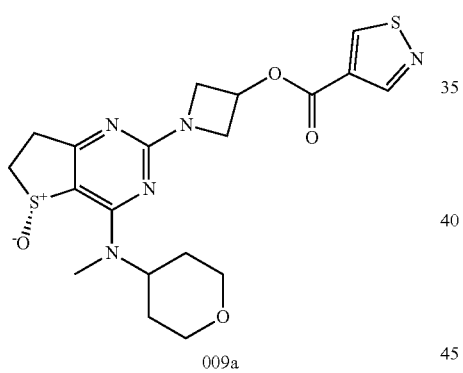

To a solution of 1-[(5R)-4-[methyl(tetrahydropyran-4-yl)amino]-5-oxido-6,7-dihydrothieno[3,2-d]pyrimidin-5-ium-2-yl]azetidin-3-ol (2.5 g, 7.4 mmol) in DCM (50 mL) was added 4-isothiazolecarboxylic acid (1.2 g, 9.6 mmol), DMAP (90 mg, 0.74 mmol) and EDAC (1.8 g, 9.6 mmol). The mixture was stirred at room temperature overnight before it was concentrated in vacuo. The residue was purified by column chromatography (DCM/MeOH gradient 20:1 to 10:1 ($R_f$=0.47 (MeOH/DCM 1:10))) and subsequently crystallized twice from n-butyl acetate. The title compound was obtained as colorless crystalline material.

$^1$H NMR (DMSO-d6) δ: 9.81 (s, 1H), 8.99 (s, 1H), 5.59-5.38 (m, 1H), 4.94-4.75 (m, 1H), 4.47 (dd, J=10.4, 6.6 Hz, 2H), 4.21-4.05 (m, 2H), 4.04-3.88 (m, 2H), 3.56-3.33 (m, 3H), 3.27-3.13 (m, 4H), 3.10-2.93 (m, 2H), 1.95-1.75 (m, 2H), 1.71-1.48 (m, 2H).

HPLC-Retention time (XE Metode 7 CM): 1.89 minutes.

Detected "M+1"-mass: 450.12.

Example 5

[1-[4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010)

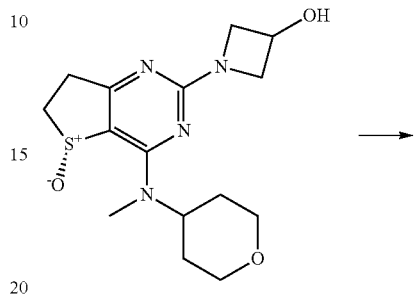

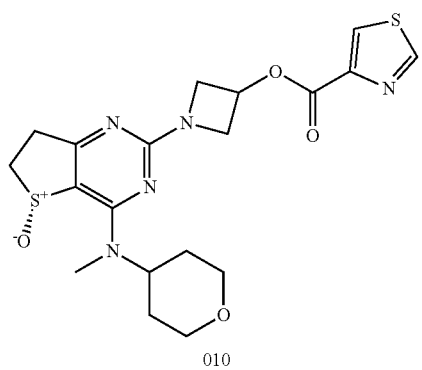

To a solution of 1-[4-[methyl(tetrahydropyran-4-yl)amino]-5-oxido-6,7-dihydrothieno-[3,2-d]pyrimidin-5-ium-2-yl]azetidin-3-ol (5.0 mg, 15 μmol) in DCE (0.2 mL) was added solutions of 4-thiazolecarboxylic acid (3.6 mg in 0.2 mL DCE, 28 μmol), DMAP (3.4 mg in 0.1 mL DCE, 28 μmol) and EDAC (5.3 mg in 0.2 mL DCE, 28 μmol). The mixture was shaken at 50° C. for 1 hour before it was concentrated in vacuo. Prep HPLC purification (acidic) afforded the title compound.

$^1$H NMR (DMSO-d6) δ: 9.21 (d, J=1.9 Hz, 1H), 8.73 (d, J=2.0 Hz, 1H), 5.49 (tt, J=6.6, 3.9 Hz, 1H), 4.97-4.70 (m, 1H), 4.58-4.43 (m, 2H), 4.22-4.10 (m, 2H), 4.01-3.91 (m, 2H), 3.55-3.47 (m, 1H), 3.44-3.37 (m, 2H), 3.26-3.21 (m, 1H), 3.20 (s, 3H), 3.09 (dd, J=17.4, 8.2 Hz, 1H), 3.02 (dd, J=13.6, 7.1 Hz, 1H), 1.94-1.79 (m, 2H), 1.69-1.52 (m, 2H).

HPLC-Retention time (XE Metode 7 CM): 1.77 minutes.

Detected "M+1"-mass: 450.12.

Example 6

[1-[(5R)-4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010a)

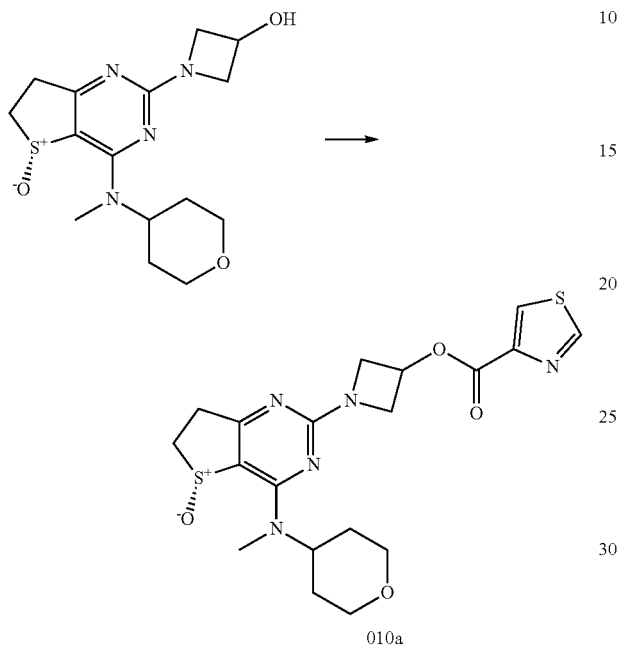

010a

To a solution of 1-[(5R)-4-[methyl(tetrahydropyran-4-yl)amino]-5-oxido-6,7-dihydrothieno[3,2-d]pyrimidin-5-ium-2-yl]azetidin-3-ol (5.0 mg, 15 µmol) in DCM (0.5 mL) was added 4-thiazolecarboxylic acid (2.5 mg, 19 µmol), DMAP (0.18 mg, 15 µmol) and EDAC (3.7 mg, 19 µmol). The mixture was stirred at room temperature for 1 hour before it was concentrated in vacuo. Prep HPLC purification (basic) afforded the title compound.

$^1$H NMR (DMSO-d6) δ: 9.21 (d, J=2.0 Hz, 1H), 8.73 (d, J=1.9 Hz, 1H), 5.49 (tt, J=6.5, 3.9 Hz, 1H), 4.95-4.75 (m, 1H), 4.48 (dd, 2H), 4.11 (dd, J=10.6, 3.8 Hz, 2H), 4.02-3.89 (m, 2H), 3.52-3.35 (m, 3H), 3.24-3.19 (m, 1H), 3.17 (s, 3H), 3.08-2.97 (m, 2H), 1.90-1.79 (m, 2H), 1.64 (d, J=12.5 Hz, 1H), 1.60-1.53 (m, 1H).

HPLC-Retention time (XE Metode 7 CM): 1.78 minutes. Detected "M+1"-mass: 450.13.

Preparation 11

N-Ethyltetrahydropyran-4-amine (Compound 011)

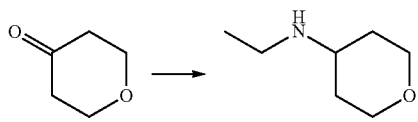

A mixture of tetrahydropyran-4-one (500 mg, 4.99 mmol), ethylammonium chloride (1.22 g, 15.0 mmol), sodium triacetoxyborhydride (1.59 g, 7.49 mmol) and acetic acid (0.43 mL, 7.49 mmol) in DCE (10 mL) was stirred at room temperature overnight. Saturated aqueous Na$_2$CO$_3$ (30 mL) was subsequently added and the aqueous phase was extracted 4 times with DCM (4×30 mL). The combined organic phases were dried over MgSO$_4$ and filtered. Evaporation to dryness afforded brown oil.

$^1$H NMR (DMSO-d6) δ: 3.81 (ddd, J=11.7, 4.1, 2.8 Hz, 2H), 3.27 (td, J=11.5, 2.3 Hz, 2H), 2.61-2.52 (m, 3H), 1.75-1.70 (m, 2H), 1.25-1.16 (m, 2H), 1.00 (t, J=7.1 Hz, 3H).

Preparation 12

2-Chloro-N-ethyl-N-tetrahydropyran-4-yl-6,7-dihydrothieno[3,2-d]pyrimidin-4-amine (Compound 012)

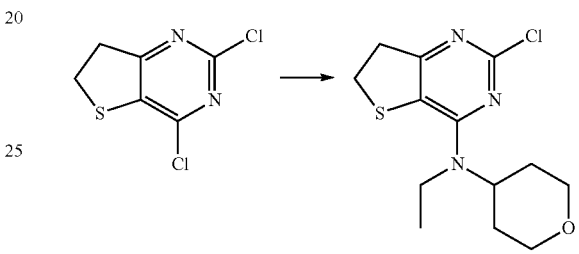

A mixture of 2,4-dichloro-6,7-dihydrothieno[3,2-d]pyrimidine (70 mg, 0.34 mmol), DIPEA (0.41 mL, 2.4 mmol) and N-ethyltetrahydropyran-4-amine (52 mg, 0.41 mmol) in DMSO (3 mL) was shaken in a sealed vial at 80° C. for 4 days. Aqueous 0.5 M HCl (30 mL) was added and the mixture was extracted three times with EtOAc (3×30 mL). The organic phases was dried over MgSO$_4$ and filtered. Evaporation to dryness afforded brown oil, which was used without further purification in the next step.

Preparation 13

2-Chloro-N-ethyl-5-oxido-N-tetrahydropyran-4-yl-6,7-dihydrothieno[3,2-d]pyrimidin-5-ium-4-amine (Compound 013)

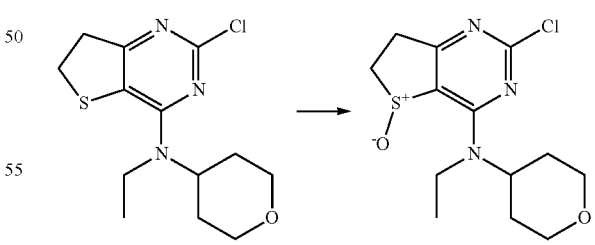

2-Chloro-N-ethyl-N-tetrahydropyran-4-yl-6,7-dihydrothieno[3,2-d]pyrimidin-4-amine (50 mg, 0.17 mmol) was dissolved in acetic acid (0.5 mL). Hydrogen peroxide (30% aqueous solution, 0.084 mL, 0.32 mmol) was added and the mixture was stirred at room temperature for 15 minutes before it was evaporated to dryness. Water (5 mL) was added to crude mixture and the aqueous phase was extracted five times with DCM (5×5 mL). The organic phases was dried over MgSO₄ and filtered. Evaporation to dryness afforded yellow oil, which was used without further purification in the next step.

Preparation 14

1-[4-[Ethyl(tetrahydropyran-4-yl)amino]-5-oxido-6,7-dihydrothieno[3,2-d]pyrimidin-5-ium-2-yl]azetidin-3-ol (Compound 014)

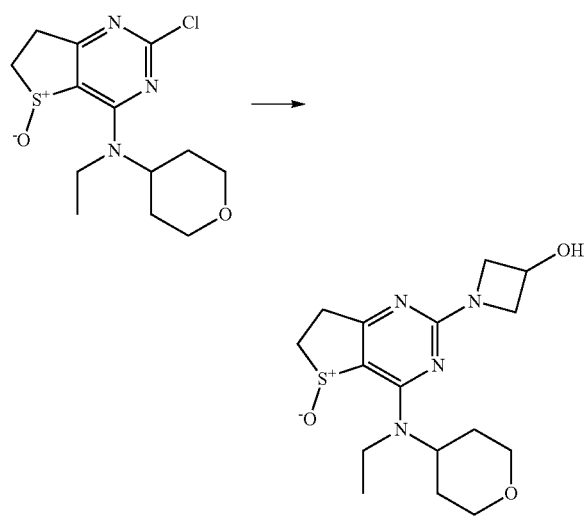

DIPEA (0.27 mL, 1.5 mmol) and azetidin-3-ol hydrochloride (22 mg, 0.20 mmol) was added to a solution of 2-chloro-N-ethyl-5-oxido-N-tetrahydropyran-4-yl-6,7-dihydrothieno[3,2-d]pyrimidin-5-ium-4-amine (48 mg, 0.15 mmol) in DMF (1.0 mL). The mixture was stirred 4 hours at room temperature before it was concentrated in vacuo. Prep HPLC purification (acetic) afforded the title compound as colorless oil.

¹H NMR (DMSO-d6) δ: 5.67 (br. s, 1H), 4.82-4.65 (m, 1H), 4.57-4.44 (m, 1H), 4.21 (dd, J=9.5, 6.6 Hz, 2H), 3.96 (dt, J=10.4, 4.8 Hz, 2H), 3.76 (dd, J=9.7, 4.4 Hz, 2H), 3.71-3.53 (m, 2H), 3.52-3.38 (m, 3H), 3.25-3.12 (m, 1H), 3.06-2.92 (m, 2H), 1.99-1.80 (m, 2H), 1.75 (br. d, 1H), 1.63 (br. d, 1H), 1.18 (t, J=6.9 Hz, 3H).

HPLC-Retention time (XE Metode 7 CM): 1.63 minutes. Detected "M+1"-mass: 353.16.

Example 7

[1-[4-[Ethyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 015)

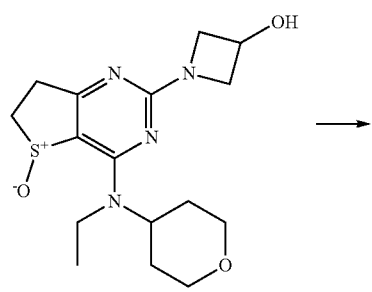

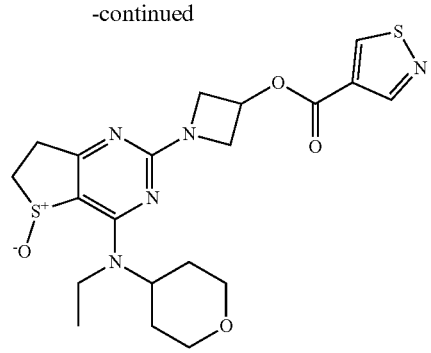

To a solution of 1-[4-[ethyl(tetrahydropyran-4-yl)amino]-5-oxido-6,7-dihydrothieno[3,2-d]pyrimidin-5-ium-2-yl]azetidin-3-ol (5.0 mg, 14 μmol) in DCE (0.2 mL) was added solutions of 4-isothiazolecarboxylic acid (2.7 mg in 0.2 mL DCE, 21 μmol), DMAP (0.52 mg in 0.1 mL DCE, 4.3 μmol) and EDAC (4.1 mg in 0.1 mL DCE, 21 μmol). The mixture was shaken at 50° C. for 20 minutes before it was concentrated in vacuo. Prep HPLC purification (basic) afforded the title compound as colorless oil.

¹H NMR (DMSO-d6) δ: 9.81 (s, 1H), 9.00 (s, 1H), 5.52-5.45 (m, 1H), 4.84-4.68 (m, 1H), 4.53-4.40 (m, 2H), 4.13 (dd, 2H), 3.97 (td, J=11.2, 4.3 Hz, 2H), 3.71-3.56 (m, 2H), 3.51-3.43 (m, 1H), 3.43-3.34 (m, 2H), 3.25-3.18 (m, 1H), 3.07-2.97 (m, 2H), 1.95-1.82 (m, 2H), 1.75 (d, J=12.3 Hz, 1H), 1.62 (d, 1H), 1.19 (t, J=6.9 Hz, 3H).

HPLC-Retention time (XE Metode 7 CM): 1.95 minutes. Detected "M+1"-mass: 464.15.

Example 8

[1-[4-[Ethyl(tetrahydropyran-4-yl)amino]-5-oxido-6,7-dihydrothieno[3,2-d]pyrimidin-5-ium-2-yl]azetidin-3-yl] thiazole-4-carboxylate (Compound 016)

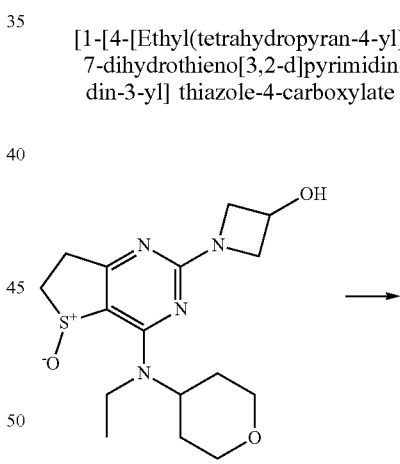

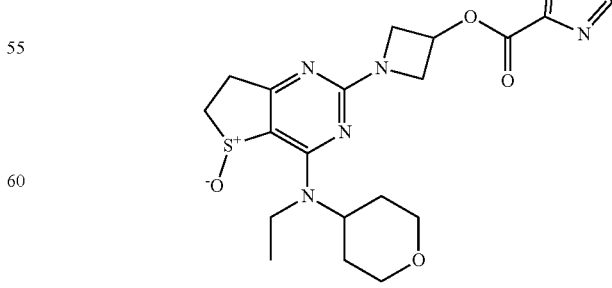

To a solution of 1-[4-[ethyl(tetrahydropyran-4-yl)amino]-5-oxido-6,7-dihydrothieno[3,2-d]pyrimidin-5-ium-2-yl]azetidin-3-ol (5.0 mg, 14 μmol) in DCE (0.2 mL) was added solutions of 4-thiazolecarboxylic acid (2.7 mg in 0.2 mL DCE, 21 μmol), DMAP (0.52 mg in 0.1 mL DCE, 4.3 μmol) and EDAC (4.1 mg in 0.1 mL DCE, 21 μmol). The mixture was shaken at 50° C. for 20 minutes before it was concentrated in vacuo. Prep HPLC purification (basic) afforded the title compound as colorless oil.

$^1$H NMR (DMSO-d6) δ: 9.21 (d, J=1.9 Hz, 1H), 8.73 (d, J=1.9 Hz, 1H), 5.53-5.45 (m, 1H), 4.85-4.69 (m, 1H), 4.47 (dd, J=10.4, 6.4 Hz, 2H), 4.11 (dd, 2H), 3.97 (td, J=11.2, 4.2 Hz, 2H), 3.71-3.57 (m, 2H), 3.51-3.45 (m, 1H), 3.44-3.35 (m, 2H), 3.25-3.18 (m, 1H), 3.07-2.97 (m, 2H), 1.95-1.82 (m, 2H), 1.75 (d, J=12.5 Hz, 1H), 1.63 (d, 1H), 1.19 (t, J=6.9 Hz, 3H).

HPLC-Retention time (XE Metode 7 CM): 1.83 minutes. Detected "M+1"-mass: 464.15.

Preparation 15

N-Propyltetrahydropyran-4-amine (Compound 017)

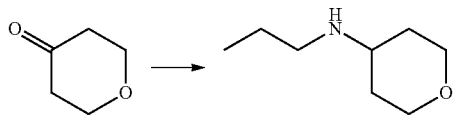

A mixture of tetrahydropyran-4-one (500 mg, 4.99 mmol), n-propylammonium chloride (1.43 g, 15.0 mmol), sodium triacetoxyborhydride (1.59 g, 7.49 mmol) and acetic acid (0.43 mL, 7.49 mmol) in DCE (10 mL) was stirred at room temperature overnight. Saturated aqueous Na$_2$CO$_3$ (30 mL) was subsequently added and the aqueous phase was extracted 4 times with DCM (4×30 mL). The combined organic phases were dried over MgSO$_4$ and filtered. Evaporation to dryness afforded brown oil.

$^1$H NMR (DMSO-d6) δ: 3.81 (dt, J=11.6, 3.9 Hz, 2H), 3.27 (td, J=11.5, 2.3 Hz, 2H), 2.59-2.52 (m, 1H), 2.47 (t, J=7.1 Hz, 2H), 1.75-1.69 (m, 2H), 1.39 (h, J=7.4 Hz, 2H), 1.25-1.16 (m, 2H), 0.86 (t, J=7.4 Hz, 3H).

Preparation 16

2-Chloro-N-propyl-N-tetrahydropyran-4-yl-6,7-dihydrothieno[3,2-d]pyrimidin-4-amine (Compound 018)

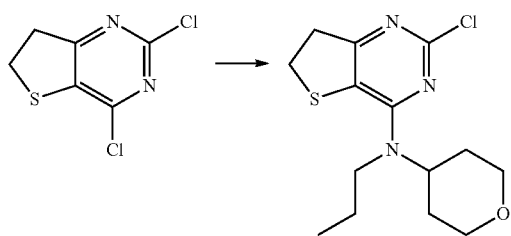 [SMILES: Clc1nc(Cl)c2c(n1)CCS2 ; CCCN(c1nc(Cl)nc2c1SCC2)C1CCOCC1]

To a suspension of 2,4-dichloro-6,7-dihydrothieno[3,2-d]pyrimidine (100 mg, 0.483 mmol) in DMSO (3.0 mL) was added DIPEA (0.59 mL, 3.4 mmol) and N-propyltetrahydropyran-4-amine (83 mg, 0.58 mmol). The pale yellow suspension was shaken for 4 hours at 80° C. and then at 60° C. for 12 days. Aqueous HCl (0.5 M, 30 mL) was added and mixture was extracted three times with EtOAc (3×30 mL). The organic phases was washing with brine (15 mL), dried over MgSO$_4$, filtered and evaporated to dryness under reduced pressure. Freeze drying afforded the title compound as brown oil, which was used without further purification in the next step.

Preparation 17

2-Chloro-N-propyl-5-oxido-N-tetrahydropyran-4-yl-6,7-dihydrothieno[3,2-d]pyrimidin-5-ium-4-amine (Compound 019)

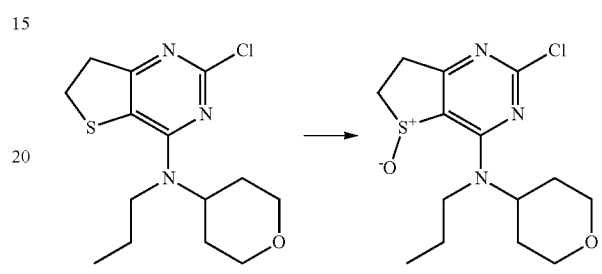

2-Chloro-N-propyl-N-tetrahydropyran-4-yl-6,7-dihydrothieno[3,2-d]pyrimidin-4-amine (105 mg, 0.335 mmol) was dissolved in acetic acid (1.0 mL). Hydrogen peroxide (30% aqueous solution, 0.17 mL, 0.335 mmol) was added and the mixture was stirred at room temperature for 15 minutes before it was evaporated to dryness. Aqueous NaHCO$_3$ (20 mL) was added to crude mixture and the aqueous phase was extracted three times with DCM (3×15 mL). The organic phases were washed with brine (20 mL), dried over MgSO$_4$ and filtered. Evaporation to dryness afforded clear yellow oil, which was used without further purification in the next step.

Preparation 18

1-[4-[Propyl(tetrahydropyran-4-yl)amino]-5-oxido-6,7-dihydrothieno[3,2-d]pyrimidin-5-ium-2-yl]azetidin-3-ol (Compound 020)

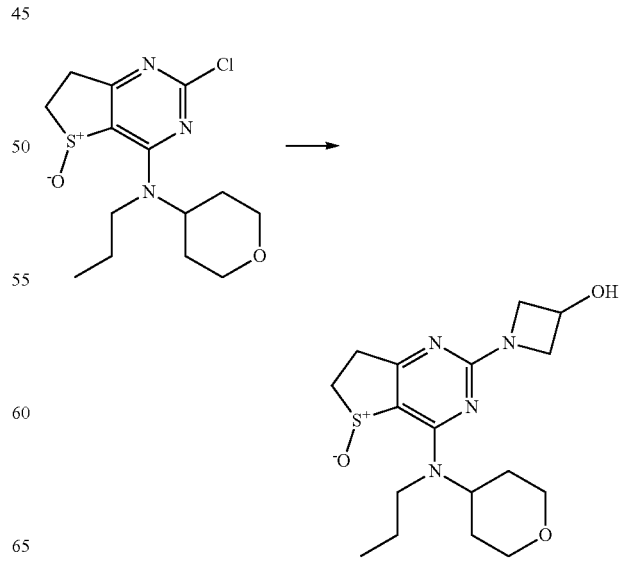

DIPEA (0.185 mL, 1.06 mmol) and azetidin-3-ol hydrochloride (30.2 mg, 0.276 mmol) was added to a solution of 2-chloro-N-propyl-5-oxido-N-tetrahydropyran-4-yl-6,7-dihydrothieno[3,2-d]pyrimidin-5-ium-4-amine (70 mg, 0.21 mmol) in DMF (1.0 mL). The mixture was stirred at room temperature for 4 hours before it was concentrated in vacuo. Prep HPLC purification (basic) afforded the title compound.

$^1$H NMR (DMSO-d6) δ: 6.33-5.44 (br s, 1H), 4.81-4.61 (m, 1H), 4.57-4.46 (m, 1H), 4.21 (dd, J=9.4, 6.6 Hz, 2H), 3.96 (dt, J=10.5, 4.8 Hz, 2H), 3.76 (dd, J=9.7, 4.4 Hz, 2H), 3.52-3.30 (m, 2H), 3.29-2.74 (m, 5H), 1.97-1.78 (m, 2H), 1.77-1.68 (m, 1H), 1.67-1.52 (m, 3H), 0.89 (t, J=7.4 Hz, 3H)

HPLC-Retention time (XE Metode 7 CM): 1.71 minutes. Detected "M+1"-mass: 367.18.

Example 9

[1-[4-[Propyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 021)

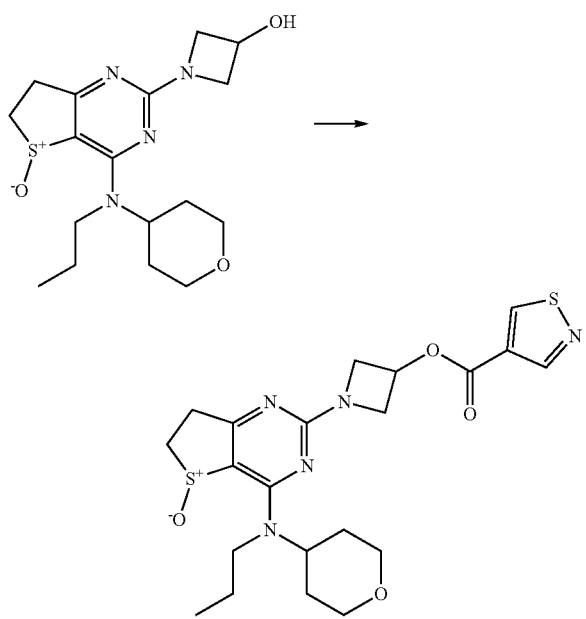

To a solution of 1-[4-[propyl(tetrahydropyran-4-yl)amino]-5-oxido-6,7-dihydrothieno[3,2-d]pyrimidin-5-ium-2-yl]azetidin-3-ol (5.0 mg, 14 μmol) in DCE (0.2 mL) was added solutions of 4-isothiazolecarboxylic acid (2.6 mg in 0.2 mL DCE, 20 μmol), DMAP (0.5 mg in 0.1 mL DCE, 4.1 μmol) and EDAC (3.9 mg in 0.2 mL DCE, 20 μmol).

The mixture was shaken at room temperature overnight before it was concentrated in vacuo. Prep HPLC purification (basic) afforded the title compound as colorless oil.

$^1$H NMR (DMSO-d6) δ: 9.81 (s, 1H), 9.00 (s, 1H), 5.49 (tt, J=6.6, 3.9 Hz, 1H), 4.88-4.65 (m, 1H), 4.54-4.39 (m, 2H), 4.13 (dd, 2H), 3.96 (td, J=11.3, 4.3 Hz, 2H), 3.54-3.35 (m, 5H), 3.25-3.16 (m, 1H), 3.07-2.97 (m, 2H), 1.95-1.82 (m, 2H), 1.74 (d, 1H), 1.65-1.54 (m, 3H), 0.90 (t, J=7.3 Hz, 3H).

HPLC-Retention time (XE Metode 7 CM): 2.03 minutes. Detected "M+1"-mass: 478.15.

Example 10

[1-[4-[Propyl(tetrahydropyran-4-yl)amino]-5-oxido-6,7-dihydrothieno[3,2-d]pyrimidin-5-ium-2-yl]azetidin-3-yl] thiazole-4-carboxylate (Compound 022)

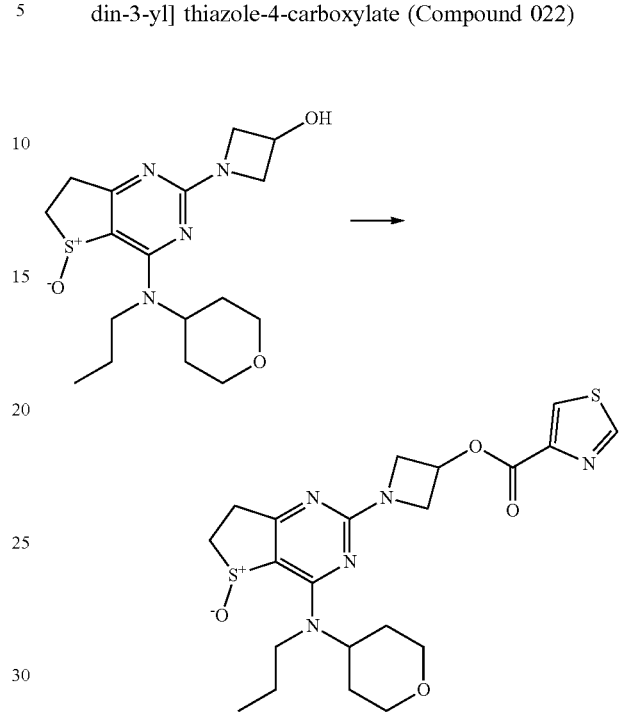

To a solution of 1-[4-[propyl(tetrahydropyran-4-yl)amino]-5-oxido-6,7-dihydrothieno-[3,2-d]pyrimidin-5-ium-2-yl]azetidin-3-ol (12 mg, 33 μmol) in DCE (0.2 mL) was added solutions of 4-thiazolecarboxylic acid (6.3 mg in 0.2 mL DCE, 49 μmol), DMAP (1.2 mg in 0.1 mL DCE, 9.8 μmol) and EDAC (9.4 mg in 0.2 mL DCE, 49 μmol). The mixture was shaken at room temperature overnight before it was concentrated in vacuo. Prep HPLC purification (basic) afforded the title compound as colorless oil.

$^1$H NMR (DMSO-d6) δ: 9.21 (d, J=2.0 Hz, 1H), 8.73 (d, J=1.9 Hz, 1H), 5.52-5.45 (m, 1H), 4.81-4.68 (m, 1H), 4.52-4.42 (m, 2H), 4.10 (dd, 2H), 3.96 (td, J=11.3, 4.3 Hz, 2H), 3.54-3.35 (m, 5H), 3.24-3.18 (m, 1H), 3.07-2.98 (m, 2H), 1.94-1.83 (m, 2H), 1.74 (d, 1H), 1.67-1.54 (m, 3H), 0.90 (t, J=7.3 Hz, 3H).

HPLC-Retention time (XE Metode 7 CM): 1.91 minutes. Detected "M+1"-mass: 478.16.

PDE4 Assay

The human PDE4D catalytic domain (UniProt no. Q08499 [S380-L740]) was incubated with a mixture of non-labelled cAMP (cyclic adenosine monophosphate) and fluorescein amidite (FAM) conjugated cAMP and titrated test or reference compound.

Following brief incubation the enzymatic reaction was stopped by addition of binding buffer containing nanoparticles with immobilized trivalent metal ions capable of binding 1) AMP phospho groups and 2) terbium (Tb) donor fluorophores. Subsequent excitation of the Tb donor triggered time-resolved FRET to adjacent FAM acceptor molecules resulting in light emission. In the presence of a PDE4 inhibitor, AMP generation was reduced resulting in a lower fluorescence signal. The cAMP phosphodiester is not bound by the detection system.

Results were expressed as IC$_{50}$ values (nM) calculated from inhibition curves where the TR-FRET signal was normalized to Tb fluorescence intensity and the negative (DMSO vehicle) and positive (10 microM a PDE4 inhibitor reference compound) controls.

PDE4 IC$_{50}$ Ranges:
* indicates that IC$_{50}$ values are >500 nM
** indicates that IC$_{50}$ values are >100 and <500 nM
*** indicates that IC$_{50}$ values are <100 nM

TNF-α RELEASE

Human peripheral blood mononuclear cells (PBMC) were isolated from fresh buffy coats by density centrifugation using lymphoprep tubes (Medinor). Frozen PBMC's were washed in serum free assay buffer (RPMI1640 with 25 mM HEPES, 1% pen/strep, 200 mM L glutamine, 0.5% human serum albumin) and living cells counted. Lipopolysaccharide (1 microg/ml; SIGMA) was added to the cells which were then transferred to 384 well tissue culture plates (5×105 c/ml) containing titrated test compounds. The cells were incubated for 18 hours at 37° C. in serum free assay buffer and the level of TNFalpha in the supernatant was quantitated by AlphaLISA (PerkinElmer) by measuring fluorescence intensity at 615 nm.

Results were expressed as IC$_{50}$ values calculated from inhibition curves using as controls the secretion in LPS stimulated wells and the secretion in cells incubated with 10 microM of a PDE4 inhibitor reference compound.

TNF-α IC$_{50}$ Ranges:
* indicates that IC$_{50}$ values are >500 nM
** indicates that IC$_{50}$ values are >100 and <500 nM
*** indicates that IC$_{50}$ values are <100 nM The results are shown in Table 1 below.

TABLE 1

| Compounds | Example | PDE4 IC$_{50}$ range | TNF-α IC$_{50}$ range |
|---|---|---|---|
| 004a | 1 | *** | *** |
| 005a | 2 | *** | *** |
| 009 | 3 | *** | *** |
| 009a | 4 | *** | *** |
| 010 | 5 | *** | *** |
| 010a | 6 | *** | *** |
| 015 | 7 | ** | ** |
| 016 | 8 | ** | ** |
| 021 | 9 | * | * |
| 022 | 10 | * | * |

The General Procedure: Esterification

An alcohol (15 µmol) was dissolved in DCE (0.2 mL). A solution of an acid (2 equiv) in DCE (0.2 mL) and a solution of DMAP (2 equiv) in DCE (0.1 mL) were added. To the resulting mixture was added EDAC (2 equiv). The mixture was shaken at 50° C. for 1 hour before it was concentrated in vacuo. The residue was dissolved in DMF (0.3 mL) and subjected to preparative LCMS purification, giving an ester.

The Examples 11 and 12 shown in Table 2 were prepared by reacting Compound 003a as described in the General Procedure with the appropriate acid:

TABLE 2

| Ex. | Cpd | Structure | IUPAC Name | HPLC Rt (min) | PDE4 IC$_{50}$ range | TNF-α IC$_{50}$ range |
|---|---|---|---|---|---|---|
| 11 | 023 | 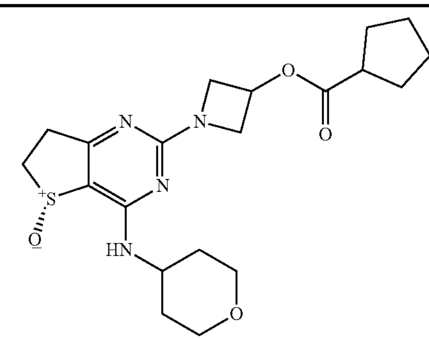 | [1-[(5R)-5-oxido-4-(tetrahydropyran-4-ylamino)-6,7-dihydro-thieno[3,2-d]pyrimidin-5-ium-2-yl]azetidin-3-yl] cyclopentanecarboxylate | 2.01 | * | * |
| 12 | 024 | 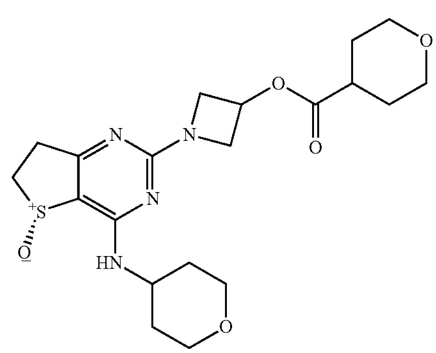 | [1-[(5R)-5-oxido-4-(tetrahydropyran-4-ylamino)-6,7-dihydrothieno[3,2-d]pyrimidin-5-ium-2-yl]azetidin-3-yl] tetrahydropyran-4-carboxylate | 1.77 |  | * |

The Examples 13-62 shown in Table 3 were prepared by reacting Compound 008 as described in the General Procedure (with the exception that the mixture was shaken at 40° C. overnight instead of at 50° C. for 1 hour) with the appropriate acid:

TABLE 3

| Ex. | Cpd | Structure | IUPAC Name | HPLC Rt (min) | PDE4 IC$_{50}$ range | TNF-α IC$_{50}$ range |
|---|---|---|---|---|---|---|
| 13 | 025 | 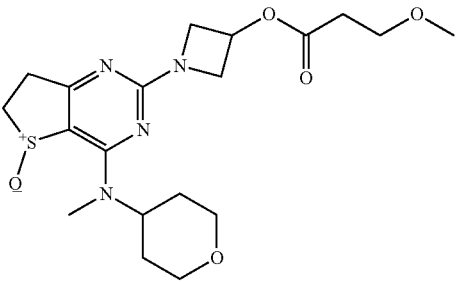 | [1-[4-[methyl(tetra-hydropyran-4-yl)amino]-5-oxido-6,7-dihydro-thieno[3,2-d]pyrimidin-5-ium-2-yl]azetidin-3-yl] 3-methoxypropanoate | 1.80 |  |  |
| 14 | 026 | 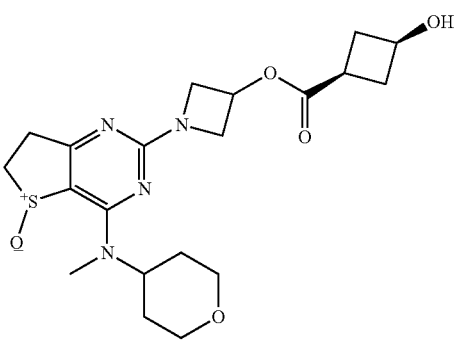 | [1-[4-[methyl(tetra-hydropyran-4-yl)amino]-5-oxido-6,7-dihydro-thieno[3,2-d]pyrimidin-5-ium-2-yl]azetidin-3-yl] 3-hydroxycyclobutane-carboxylate | 1.72 |  |  |
| 15 | 027 | 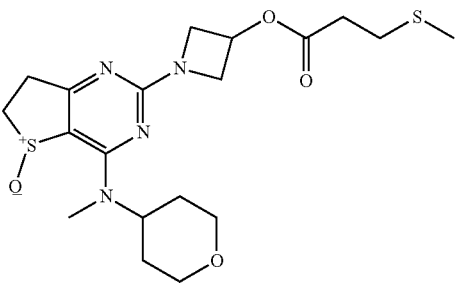 | [1-[4-[methyl(tetra-hydropyran-4-yl)amino]-5-oxido-6,7-dihydro-thieno[3,2-d]pyrimidin-5-ium-2-yl]azetidin-3-yl] 3-methylsulfanyl-propanoate | 1.94 | * | * |
| 16 | 028 | 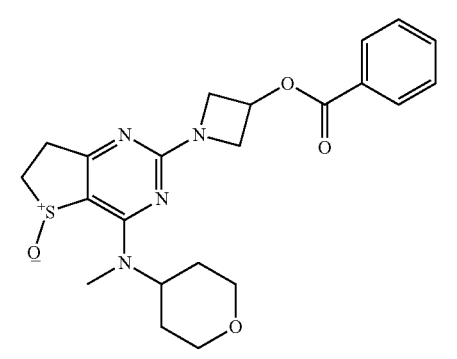 | [1-[4-[methyl(tetra-hydropyran-4-yl)amino]-5-oxido-6,7-dihydro-thieno[3,2-d]pyrimidin-5-ium-2-yl]azetidin-3-yl] benzoate | 2.07 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 17 | 029 | 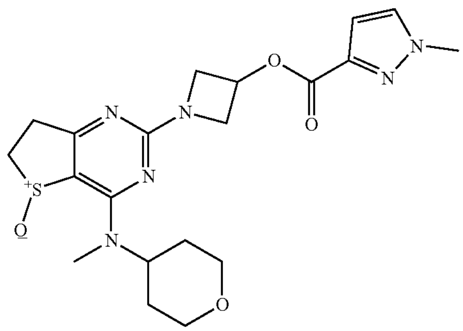 | [1-[4-[methyl(tetra-hydropyran-4-yl)amino]-5-oxido-6,7-dihydro-thieno[3,2-d]pyrimidin-5-ium-2-yl]azetidin-3-yl] 1-methylpyrazole-3-carboxylate | 1.78 | * | * |
| 18 | 030 | 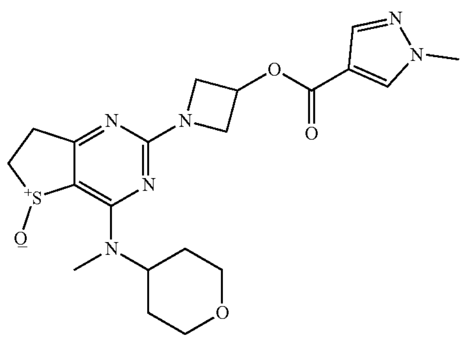 | [1-[4-[methyl(tetra-hydropyran-4-yl)amino]-5-oxido-6,7-dihydro-thieno[3,2-d]pyrimidin-5-ium-2-yl]azetidin-3-yl] 1-methylpyrazole-4-carboxylate | 1.79 | * | * |
| 19 | 031 | 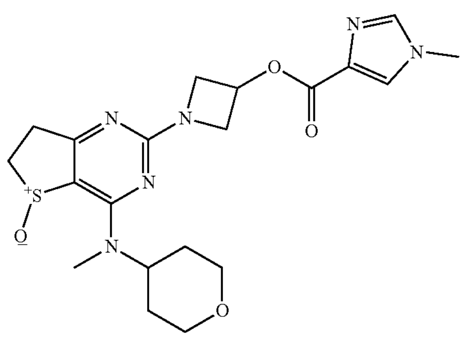 | [1-[4-[methyl(tetra-hydropyran-4-yl)amino]-5-oxido-6,7-dihydro-thieno[3,2-d]pyrimidin-5-ium-2-yl]azetidin-3-yl] 1-methylimidazole-4-carboxylate | 1.69 | * | * |
| 20 | 032 | 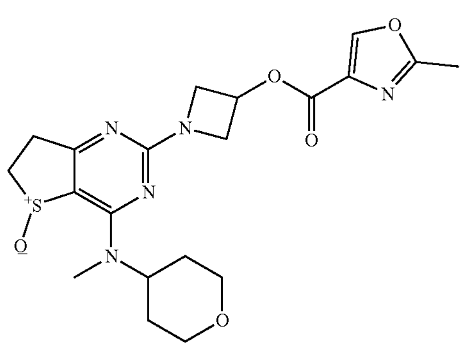 | [1-[4-[methyl(tetra-hydropyran-4-yl)amino]-5-oxido-6,7-dihydro-thieno[3,2-d]pyrimidin-5-ium-2-yl]azetidin-3-yl] 2-methyloxazole-4-carboxylate | 1.80 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 21 | 033 | 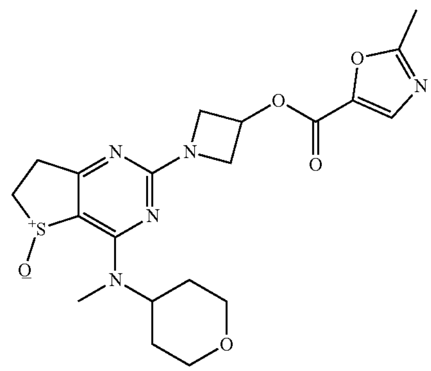 | [1-[4-[methyl(tetra-hydropyran-4-yl)amino]-5-oxido-6,7-dihydro-thieno[3,2-d]pyrimidin-5-ium-2-yl]azetidin-3-yl] 2-methyloxazole-5-carboxylate | 1.82 | * | * |
| 22 | 034 | 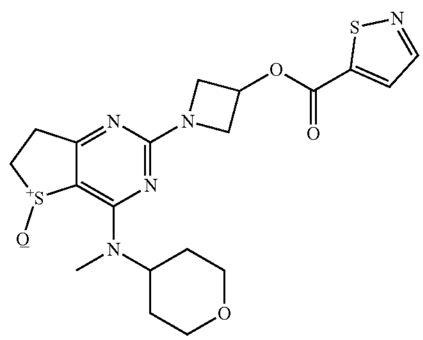 | [1-[4-[methyl(tetra-hydropyran-4-yl)amino]-5-oxido-6,7-dihydro-thieno[3,2-d]pyrimidin-5-ium-2-yl]azetidin-3-yl] isothiazole-5-carboxylate | 1.93 | * | * |
| 23 | 035 | 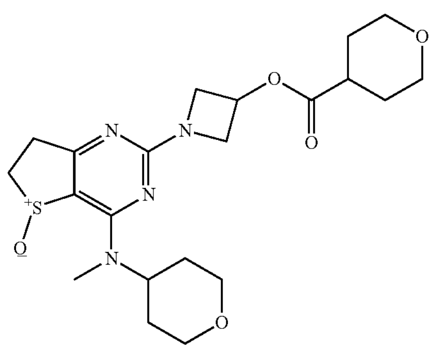 | [1-[4-[methyl(tetra-hydropyran-4-yl)amino]-5-oxido-6,7-dihydro-thieno[3,2-d]pyrimidin-5-ium-2-yl]azetidin-3-yl] tetrahydropyran-4-carboxylate | 1.82 | * | * |
| 24 | 037 | 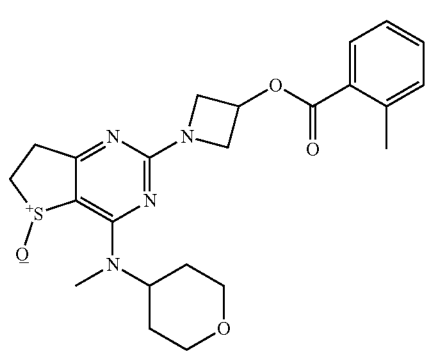 | [1-[4-[methyl(tetra-hydropyran-4-yl)amino]-5-oxido-6,7-dihydro-thieno[3,2-d]pyrimidin-5-ium-2-yl]azetidin-3-yl] 2-methylbenzoate | 2.16 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 25 | 038 | 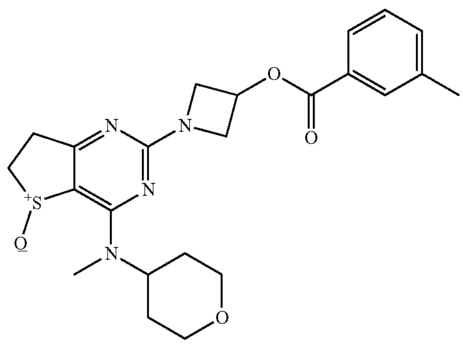 | [1-[4-[methyl(tetra-hydropyran-4-yl)amino]-5-oxido-6,7-dihydro-thieno[3,2-d]pyrimidin-5-ium-2-yl]azetidin-3-yl] 3-methylbenzoate | 2.17 | * | * |
| 26 | 039 | 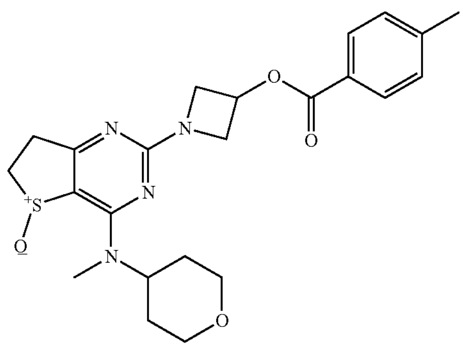 | [1-[4-[methyl(tetra-hydropyran-4-yl)amino]-5-oxido-6,7-dihydro-thieno[3,2-d]pyrimidin-5-ium-2-yl]azetidin-3-yl] 4-methylbenzoate | 2.16 | * | * |
| 27 | 040 | 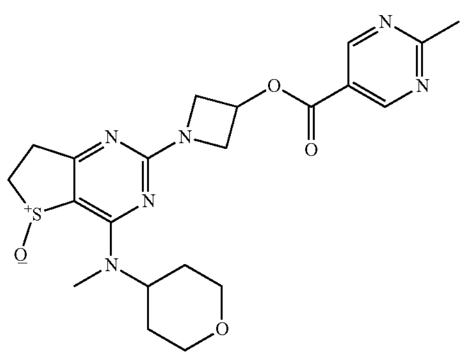 | [1-[4-[methyl(tetra-hydropyran-4-yl)amino]-5-oxido-6,7-dihydro-thieno[3,2-d]pyrimidin-5-ium-2-yl]azetidin-3-yl] 2-methylpyrimidine-5-carboxylate | 1.80 | * | * |
| 28 | 041 | 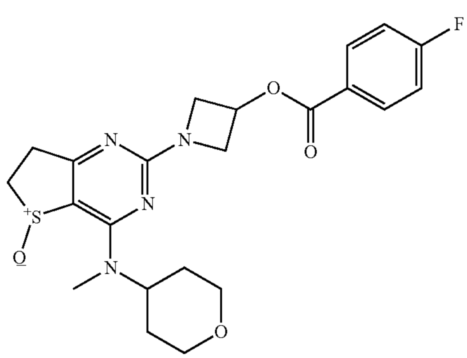 | [1-[4-[methyl(tetra-hydropyran-4-yl)amino]-5-oxido-6,7-dihydro-thieno[3,2-d]pyrimidin-5-ium-2-yl]azetidin-3-yl] 4-fluorobenzoate | 2.10 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 29 | 042 | 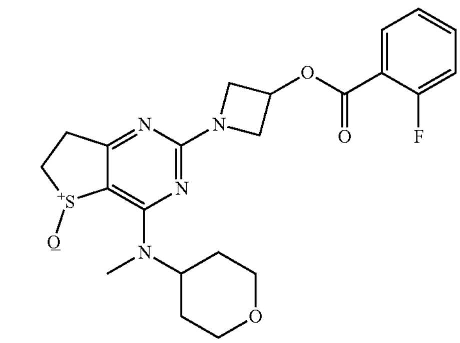 | [1-[4-[methyl(tetra-hydropyran-4-yl)amino]-5-oxido-6,7-dihydro-thieno[3,2-d]pyrimidin-5-ium-2-yl]azetidin-3-yl] 2-fluorobenzoate | 2.05 | * | * |
| 30 | 043 | 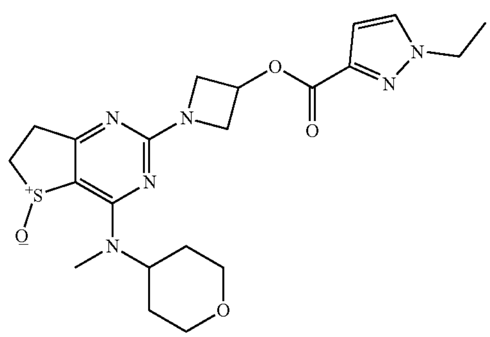 | [1-[4-[methyl(tetra-hydropyran-4-yl)amino]-5-oxido-6,7-dihydro-thieno[3,2-d]pyrimidin-5-ium-2-yl]azetidin-3-yl] 1-ethylpyrazole-3-carboxylate | 1.85 | * | * |
| 31 | 044 | 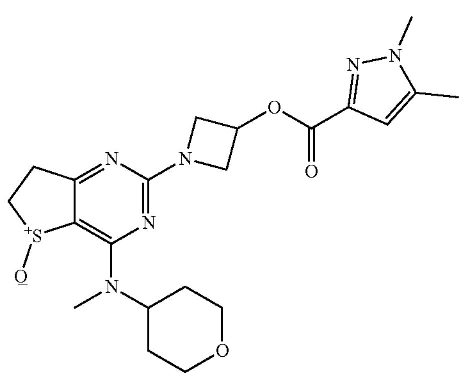 | [1-[4-[methyl(tetra-hydropyran-4-yl)amino]-5-oxido-6,7-dihydro-thieno[3,2-d]pyrimidin-5-ium-2-yl]azetidin-3-yl] 1,5-dimethylpyrazole-3-carboxylate | 1.84 | * | * |
| 32 | 045 | 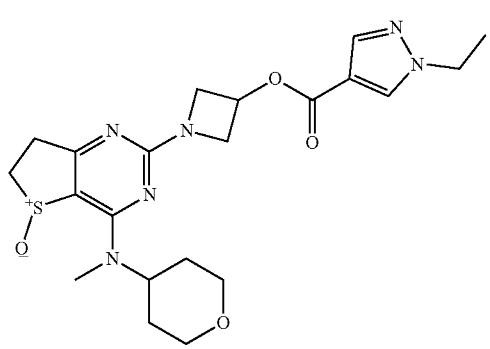 | [1-[4-[methyl(tetra-hydropyran-4-yl)amino]-5-oxido-6,7-dihydro-thieno[3,2-d]pyrimidin-5-ium-2-yl]azetidin-3-yl] 1-ethylpyrazole-4-carboxylate | 1.86 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 33 | 046 | 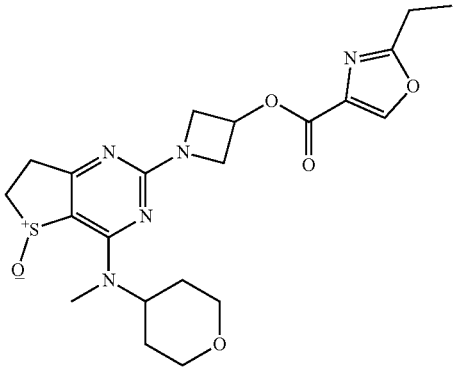 | [1-[4-[methyl(tetra-hydropyran-4-yl)amino]-5-oxido-6,7-dihydro-thieno[3,2-d]pyrimidin-5-ium-2-yl]azetidin-3-yl] 2-ethyloxazole-4-carboxylate | 1.88 | * | * |
| 34 | 047 | 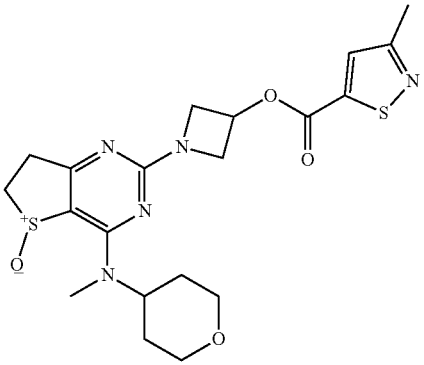 | [1-[4-[methyl(tetra-hydropyran-4-yl)amino]-5-oxido-6,7-dihydro-thieno[3,2-d]pyrimidin-5-ium-2-yl]azetidin-3-yl] 3-methylisothiazole-5-carboxylate | 1.99 | * | * |
| 35 | 048 | 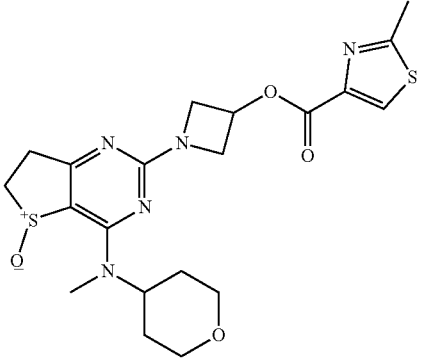 | [1-[4-[methyl(tetra-hydropyran-4-yl)amino]-5-oxido-6,7-dihydro-thieno[3,2-d]pyrimidin-5-ium-2-yl]azetidin-3-yl] 2-methylthiazole-4-carboxylate | 1.84 | * | * |
| 36 | 049 | 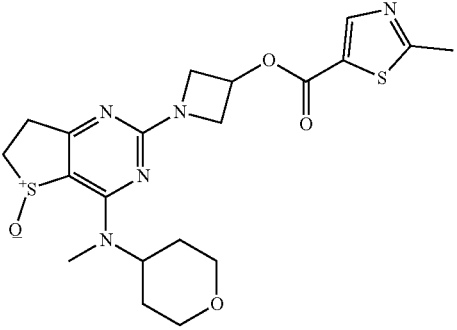 | [1-[4-[methyl(tetra-hydropyran-4-yl)amino]-5-oxido-6,7-dihydro-thieno[3,2-d]pyrimidin-5-ium-2-yl]azetidin-3-yl] 2-methylthiazole-5-carboxylate | 1.89 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 37 | 050 | AND Enantiomer | [1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate | 1.81 | *** | *** |
| 38 | 051 | 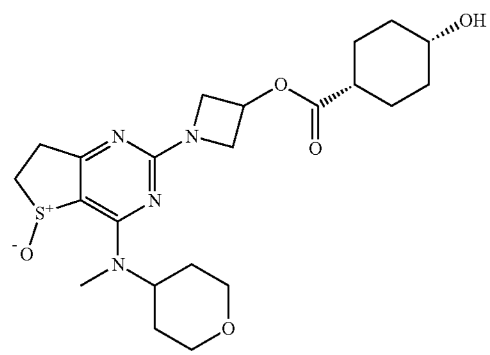 [SMILES: CN(c1nc(N2CC(OC(=O)[C@H]3CC[C@@H](O)CC3)C2)nc2c1[S+](O)CC2)C1CCOCC1] | [1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate | 1.81 | * | * |
| 39 | 052 | 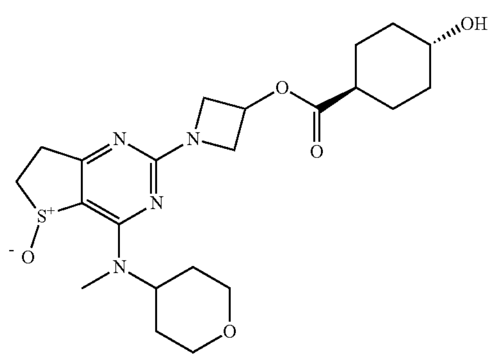 [SMILES: CN(c1nc(N2CC(OC(=O)[C@H]3CC[C@H](O)CC3)C2)nc2c1[S+](O)CC2)C1CCOCC1] | [1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate | 1.77 | * | * |
| 40 | 053 | 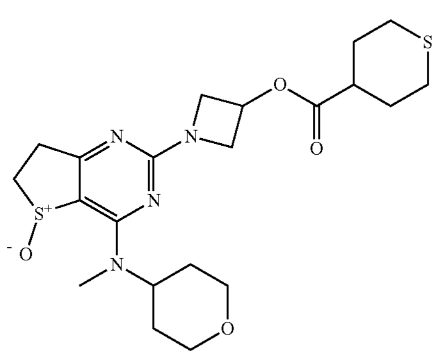 [SMILES: CN(c1nc(N2CC(OC(=O)C3CCSCC3)C2)nc2c1[S+](O)CC2)C1CCOCC1] | [1-[4-[methyl(tetrahydropyran-4-yl)amino]-5-oxido-6,7-dihydrothieno[3,2-d]pyrimidin-5-ium-2-yl]azetidin-3-yl] tetrahydrothiopyran-4-carboxylate | 2.03 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 41 | 054 | 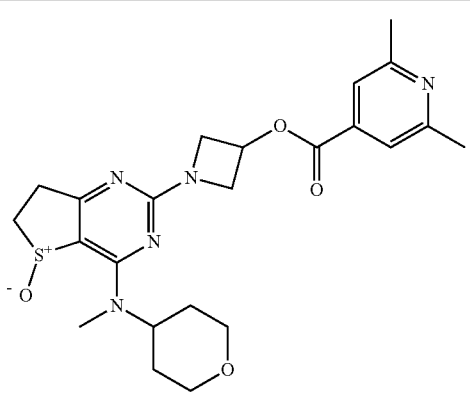 [SMILES: Cc1cc(C(=O)OC2CN(c3nc4c(c(N(C)C5CCOCC5)n3)[S+](O)CC4)C2)cc(C)n1] | [1-[4-[methyl(tetra-hydropyran-4-yl)amino]-5-oxido-6,7-dihydro-thieno[3,2-d]pyrimidin-5-ium-2-yl]azetidin-3-yl] 2,6-dimethylpyridine-4-carboxylate | 1.83 | * | * |
| 42 | 055 | 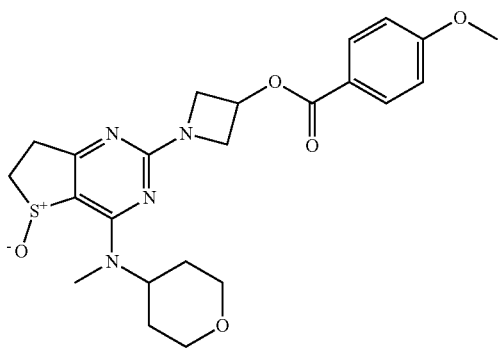 | [1-[4-[methyl(tetra-hydropyran-4-yl)amino]-5-oxido-6,7-dihydro-thieno[3,2-d]pyrimidin-5-ium-2-yl]azetidin-3-yl] 4-methoxybenzoate | 2.08 | * | * |
| 43 | 056 | 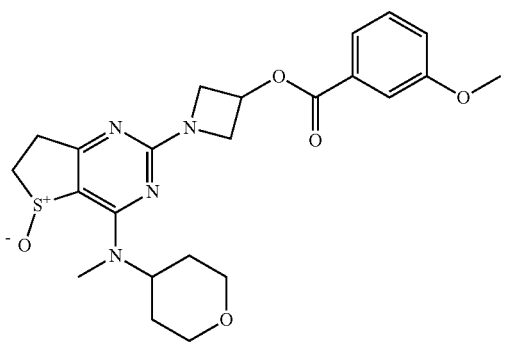 [SMILES: COc1cccc(C(=O)OC2CN(c3nc4c(c(N(C)C5CCOCC5)n3)[S+](O)CC4)C2)c1] | [1-[4-[methyl(tetra-hydropyran-4-yl)amino]-5-oxido-6,7-dihydro-thieno[3,2-d]pyrimidin-5-ium-2-yl]azetidin-3-yl] 3-methoxybenzoate | 2.10 | * | * |
| 44 | 057 | 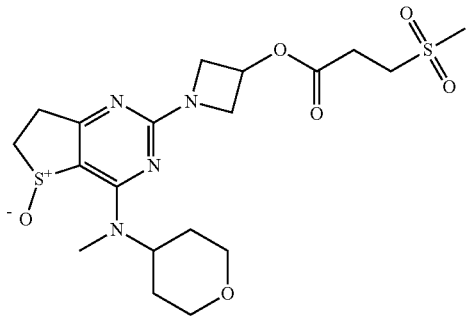 [SMILES: CN(c1nc(N2CC(OC(=O)CCS(C)(=O)=O)C2)nc2c1[S+](O)CC2)C1CCOCC1] | [1-[4-[methyl(tetra-hydropyran-4-yl)amino]-5-oxido-6,7-dihydro-thieno[3,2-d]pyrimidin-5-ium-2-yl]azetidin-3-yl] 5-methylsulfonyl-propanoate | 1.72 |  |  |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 45 | 058 | 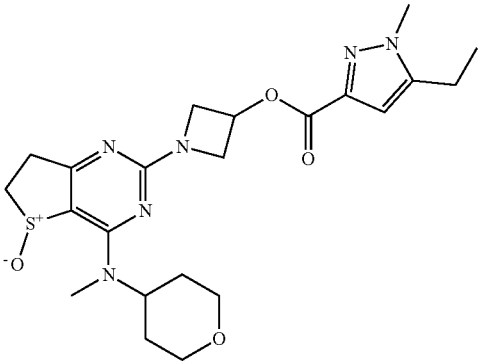 | [1-[4-[methyl(tetra-hydropyran-4-yl)amino]-5-oxido-6,7-dihydro-thieno[3,2-d]pyrimidin-5-ium-2-yl]azetidin-3-yl] 5-ethyl-1-methyl-pyrazole-3-carboxylate | 1.92 | * | * |
| 46 | 059 | 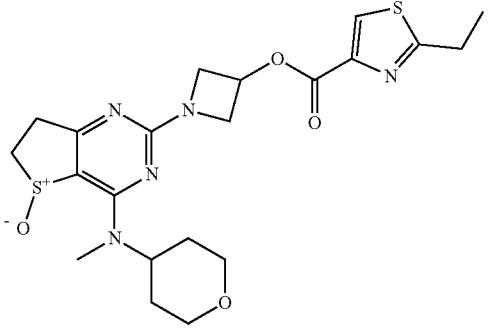 [SMILES: CCc1nc(C(=O)OC2CN(c3nc4c(c(N(C)C5CCOCC5)n3)[S+](O)CC4)C2)cs1] | [1-[4-[methyl(tetra-hydropyran-4-yl)amino]-5-oxido-6,7-dihydro-thieno[3,2-d]pyrimidin-5-ium-2-yl]azetidin-3-yl] 2-ethylthiazole-4-carboxylate | 1.93 | * | * |
| 47 | 060 | 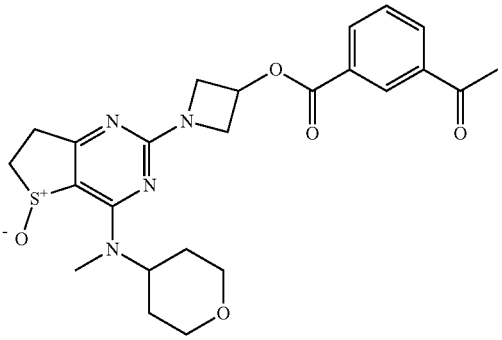 [SMILES: CC(=O)c1cccc(C(=O)OC2CN(c3nc4c(c(N(C)C5CCOCC5)n3)[S+](O)CC4)C2)c1] | [1-[4-[methyl(tetra-hydropyran-4-yl)amino]-5-oxido-6,7-dihydro-thieno[3,2-d]pyrimidin-5-ium-2-yl]azetidin-3-yl] 3-acetylbenzoate | 1.99 | * | * |
| 48 | 061 | 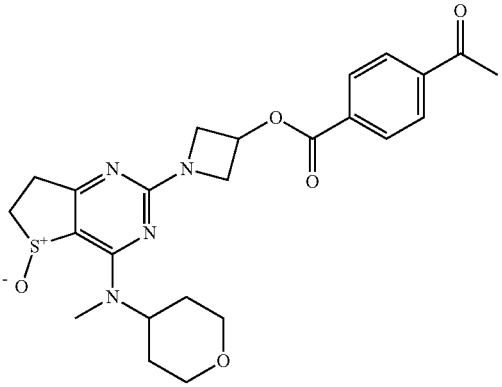 [SMILES: CC(=O)c1ccc(C(=O)OC2CN(c3nc4c(c(N(C)C5CCOCC5)n3)[S+](O)CC4)C2)cc1] | [1-[4-[methyl(tetra-hydropyran-4-yl)amino]-5-oxido-6,7-dihydro-thieno[3,2-d]pyrimidin-5-ium-2-yl]azetidin-3-yl] 4-acetylbenzoate | 2.01 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 49 | 062 | 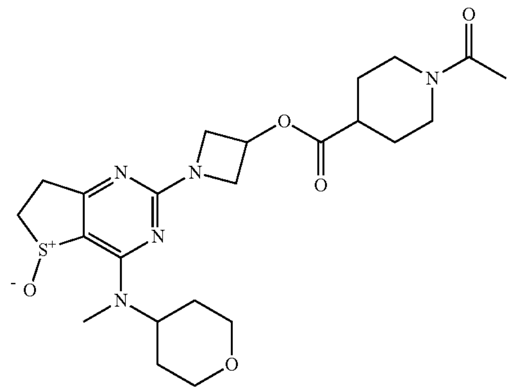 [SMILES: CC(=O)N1CCC(C(=O)OC2CN(c3nc4c(c(N(C)C5CCOCC5)n3)[S+](O)CC4)C2)CC1] | [1-[4-[methyl(tetrahydropyran-4-yl)amino]-5-oxido-6,7-dihydrothieno[3,2-d]pyrimidin-5-ium-2-yl]azetidin-3-yl] 1-acetylpiperidine-4-carboxylate | 1.76 | * | * |
| 50 | 063 | 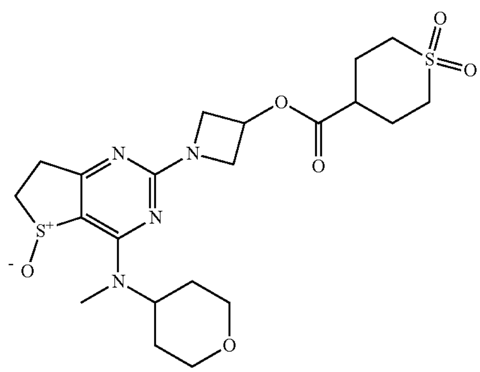 [SMILES: CN(c1nc(N2CC(OC(=O)C3CCS(=O)(=O)CC3)C2)nc2c1[S+](O)CC2)C1CCOCC1] | [1-[4-[methyl(tetrahydropyran-4-yl)amino]-5-oxido-6,7-dihydrothieno[3,2-d]pyrimidin-5-ium-2-yl]azetidin-3-yl] 1,1-dioxothiane-4-carboxylate | 1.76 |  |  |
| 51 | 064 | 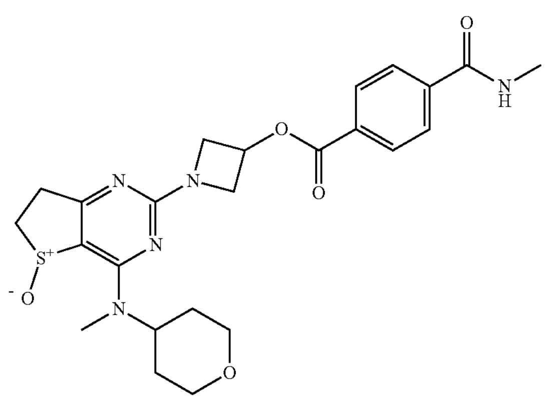 [SMILES: CN(C)C(=O)c1ccc(C(=O)OC2CN(c3nc4c(c(N(C)C5CCOCC5)n3)[S+](O)CC4)C2)cc1] | [1-[4-[methyl(tetrahydropyran-4-yl)amino]-5-oxido-6,7-dihydrothieno[3,2-d]pyrimidin-5-ium-2-yl]azetidin-3-yl] 4-(methylcarbamoyl)benzoate | 1.82 | * | * |
| 52 | 065 | 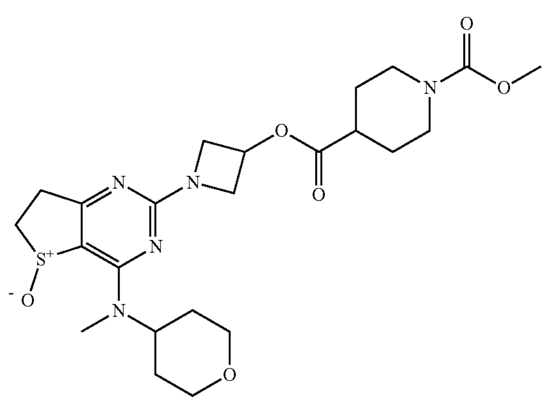 [SMILES: CN(C)C(=O)N1CCC(C(=O)OC2CN(c3nc4c(c(N(C)C5CCOCC5)n3)[S+](O)CC4)C2)CC1] | O1-methyl O4-[1-[4-[methyl(tetrahydropyran-4-yl)amino]-5-oxido-6,7-dihydrothieno[3,2-d]pyrimidin-5-ium-2-yl]azetidin-3-yl] piperidine-1,4-dicarboxylate | 1.90 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 53 | 066 | 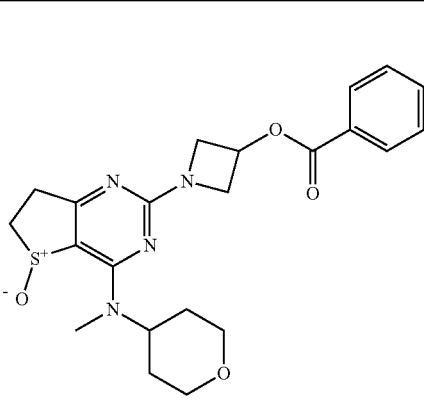 | [1-[4-[methyl(tetra-hydropyran-4-yl)amino]-5-oxido-6,7-dihydro-thieno[3,2-d]pyrimidin-5-ium-2-yl]azetidin-3-yl] 4-(dimethylcarbamoyl)-benzoate | 1.86 | * | * |
| 54 | 067 | 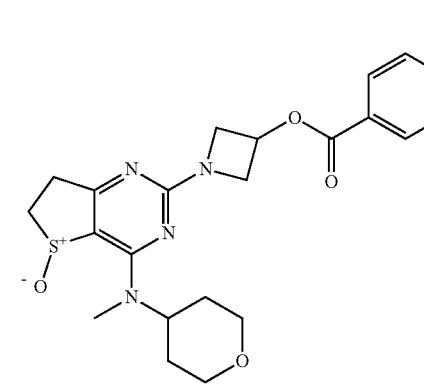 | [1-[4-[methyl(tetra-hydropyran-4-yl)amino]-5-oxido-6,7-dihydro-thieno[3,2-d]pyrimidin-5-ium-2-yl]azetidin-3-yl] 4-methylsulfonyl-benzoate | 1.90 | * | * |
| 55 | 068 | 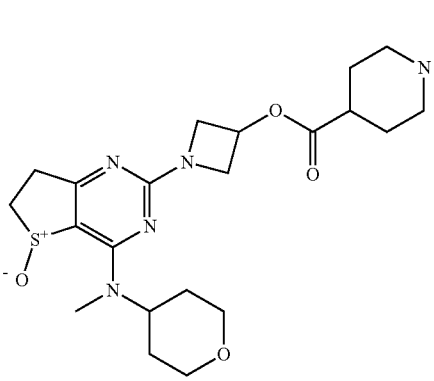 | [1-[4-[methyl(tetra-hydropyran-4-yl)amino]-5-oxido-6,7-dihydro-thieno[3,2-d]pyrimidin-5-ium-2-yl]azetidin-3-yl] 1-(dimethylcarbamoyl)-piperidine-4-carboxylate | 1.84 | * | * |
| 56 | 069 | 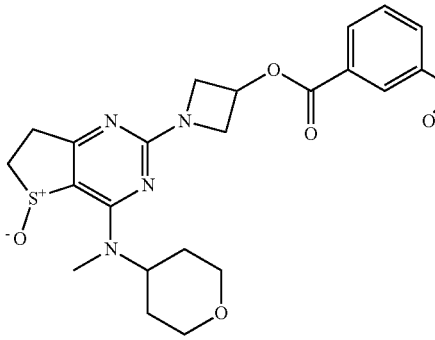 | [1-[4-[methyl(tetra-hydropyran-4-yl)amino]-5-oxido-6,7-dihydro-thieno[3,2-d]pyrimidin-5-ium-2-yl]azetidin-3-yl] 3-ethylsulfonylbenzoate | 1.96 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 57 | 070 | 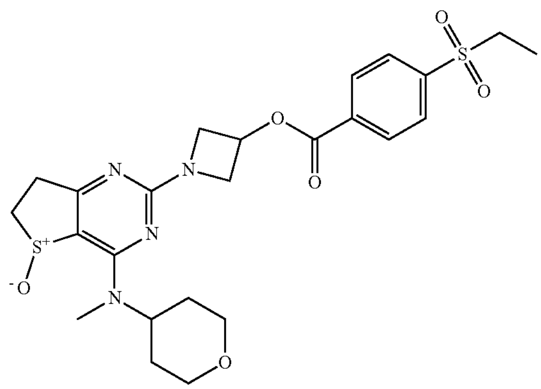 | [1-[4-[methyl(tetra-hydropyran-4-yl)amino]-5-oxido-6,7-dihydro-thieno[3,2-d]pyrimidin-5-ium-2-yl]azetidin-3-yl] 4-ethylsulfonylbenzoate | 1.97 | * | * |
| 58 | 071 | 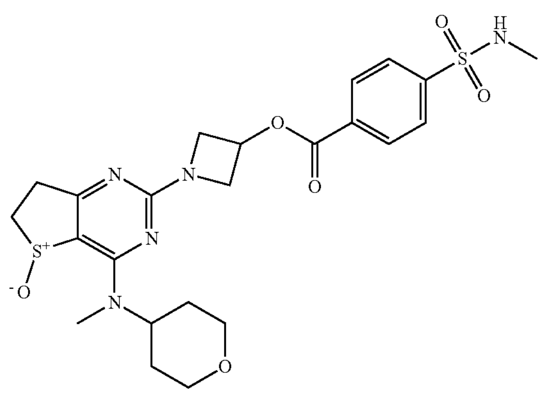 | [1-[4-[methyl(tetra-hydropyran-4-yl)amino]-5-oxido-6,7-dihydro-thieno[3,2-d]pyrimidin-5-ium-2-yl]azetidin-3-yl] 4-(methylsulfamoyl)-benzoate | 1.92 | * | * |
| 59 | 072 | 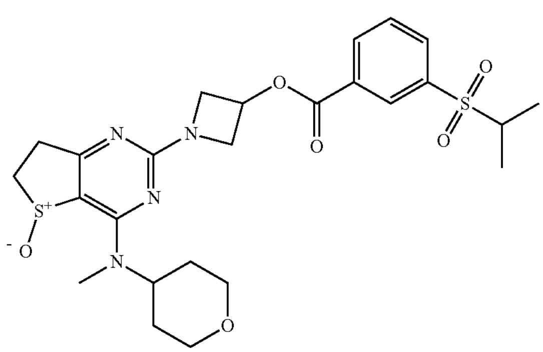 [SMILES: CC(C)S(=O)(=O)c1cccc(C(=O)OC2CN(c3nc4c(c(N(C)C5CCOCC5)n3)[S+](O)CC4)C2)c1] | [1-[4-[methyl(tetra-hydropyran-4-yl)amino]-5-oxido-6,7-dihydro-thieno[3,2-d]pyrimidin-5-ium-2-yl]azetidin-3-yl] 3-isopropylsulfonyl-benzoate | 2.01 | * | * |
| 60 | 073 | 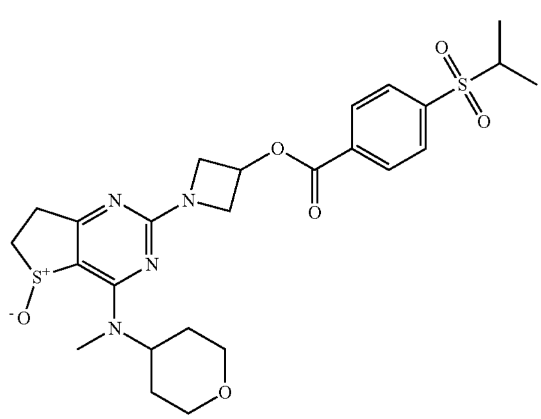 | [1-[4-[methyl(tetra-hydropyran-4-yl)amino]-5-oxido-6,7-dihydro-thieno[3,2-d]pyrimidin-5-ium-2-yl]azetidin-3-yl] 4-isopropylsulfonyl-benzoate | 2.03 | * | * |

TABLE 3-continued

| Ex. | Cpd | Structure | IUPAC Name | HPLC Rt (min) | PDE4 IC$_{50}$ range | TNF-α IC$_{50}$ range |
|---|---|---|---|---|---|---|
| 61 | 074 | 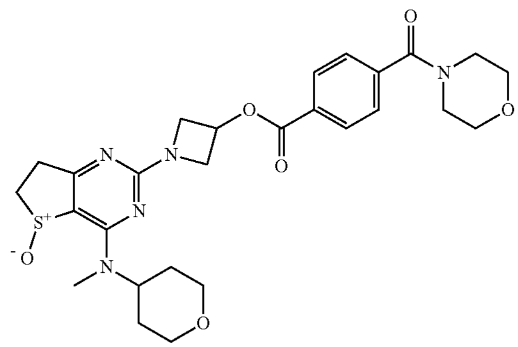 [SMILES: CN(c1nc(N2CC(OC(=O)c3ccc(C(=O)N4CCOCC4)cc3)C2)nc2c1[S+](O)CC2)C1CCOCC1] | [1-[4-[methyl(tetrahydropyran-4-yl)amino]-5-oxido-6,7-dihydrothieno[3,2-d]pyrimidin-5-ium-2-yl]azetidin-3-yl] 4-(morpholine-4-carbonyl)benzoate | 1.85 | * | * |
| 62 | 075 | 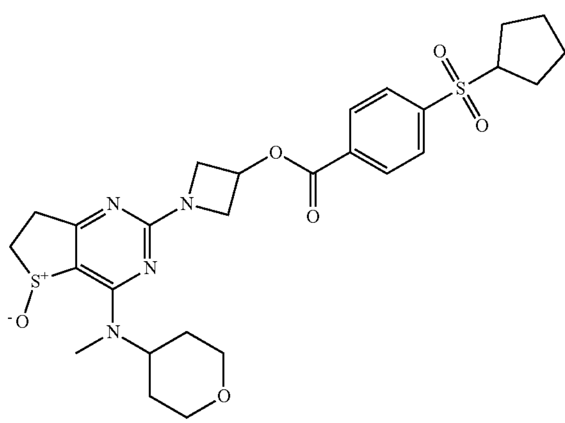 | [1-[4-[methyl(tetrahydropyran-4-yl)amino]-5-oxido-6,7-dihydrothieno[3,2-d]pyrimidin-5-ium-2-yl]azetidin-3-yl] 4-cyclopentylsulfonylbenzoate | 2.12 | * | * |

The Examples 63 and 64 shown in Table 4 were prepared by reacting Compound 008a as described in Example 4 with the appropriate acid replacing 4-isothiazolecarboxylic acid:

TABLE 4

| Ex. | Cpd | Structure | IUPAC Name | HPLC Rt (min) | PDE4 IC$_{50}$ range | TNF-α IC$_{50}$ range |
|---|---|---|---|---|---|---|
| 63 | 075 | 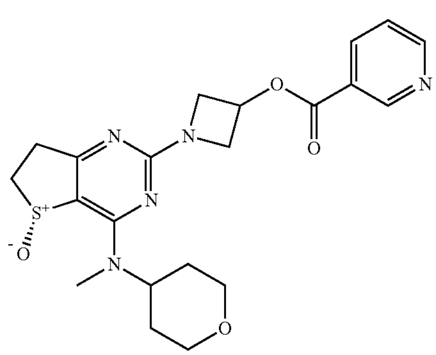 [SMILES: CN(c1nc(N2CC(OC(=O)c3cccnc3)C2)nc2c1[S@+](O)CC2)C1CCOCC1] | [1-[(5R)-4-[methyl-(tetrahydropyran-4-yl)amino]-5-oxido-6,7-dihydrothieno[3,2-d]pyrimidin-5-ium-2-yl]azetidin-3-yl] pyridine-3-carboxylate | 1.81 |  | * |

TABLE 4-continued

| Ex. | Cpd | Structure | IUPAC Name | HPLC Rt (min) | PDE4 IC$_{50}$ range | TNF-α IC$_{50}$ range |
|---|---|---|---|---|---|---|
| 64 | 038a | 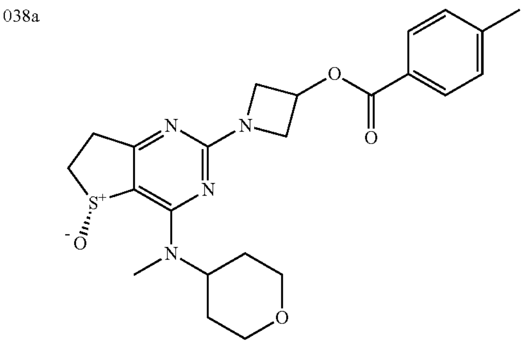 | [1-[(5R)-4-[methyl-(tetrahydropyran-4-yl)amino]-5-oxido-6,7-dihydrothieno[3,2-d]pyrimidin-5-ium-2-yl]azetidin-3-yl] 4-methylbenzoate | 2.15 | * | * |

Preparation 19

2-Chloro-N-(6-oxaspiro[3.3]heptan-2-yl)-6,7-dihydrothieno[3,2-d]pyrimidin-4-amine (Compound 076)

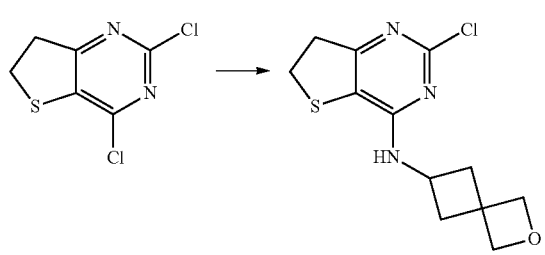 [SMILES: Clc1nc(Cl)c2c(n1)CCS2 ; Clc1nc2c(c(NC3CC4(COC4)C3)n1)SCC2]

To a solution of 2,4-dichloro-6,7-dihydrothieno[3,2-d]pyrimidine (2.50 g, 12 mmol) in DMSO (8 mL) was added DIPEA (4.2 mL, 24 mmol) and 6-oxaspiro[3.3]heptan-2-amine hydrochloride (2.00 g, 13 mmol). The reaction mixture was stirred at rt overnight. Water (10 mL) was added and the obtained slurry was stirred for 30 min before filtration and subsequent washings with water afforded the title compound as solid material.

$^1$H NMR (DMSO-d6) δ: 7.43 (d, J=7.1 Hz, 1H), 4.62 (s, 2H), 4.49 (s, 2H), 4.26 (h, J=8.1 Hz, 1H), 3.39-3.31 (m, 2H), 3.17-3.08 (m, 2H), 2.62-2.53 (m, 2H), 2.30-2.16 (m, 2H).

Preparation 20

2-Chloro-5-oxido-N-(6-oxaspiro[3.3]heptan-2-yl)-6,7-dihydrothieno[3,2-d]pyrimidin-5-ium-4-amine (Compound 077)

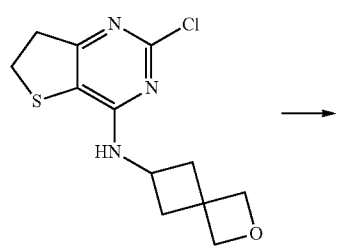

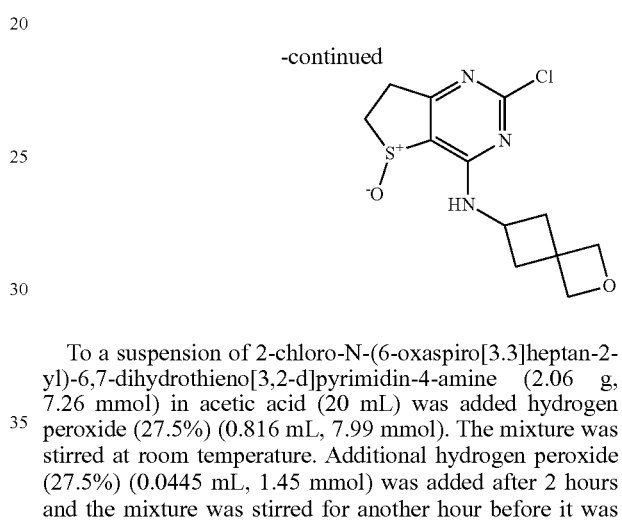

To a suspension of 2-chloro-N-(6-oxaspiro[3.3]heptan-2-yl)-6,7-dihydrothieno[3,2-d]pyrimidin-4-amine (2.06 g, 7.26 mmol) in acetic acid (20 mL) was added hydrogen peroxide (27.5%) (0.816 mL, 7.99 mmol). The mixture was stirred at room temperature. Additional hydrogen peroxide (27.5%) (0.0445 mL, 1.45 mmol) was added after 2 hours and the mixture was stirred for another hour before it was diluted with water (20 mL) and extracted twice with DCM (2×30 mL). The combined organic phases were concentrated in vacuo and the obtained yellow oil was crystallized from MTBE. Filtration and washings with TBME afforded the title compound as solid material.

$^1$H NMR (DMSO-d6) δ: 8.84 (d, J=7.0 Hz, 1H), 4.63 (s, 2H), 4.55-4.46 (m, 2H), 4.46-4.30 (m, 1H), 3.58 (dt, J=17.5, 7.7 Hz, 1H), 3.39 (dt, J=13.8, 8.0 Hz, 1H), 3.21-3.09 (m, 1H), 3.09-2.96 (m, 1H), 2.68-2.54 (m, 2H), 2.40-2.23 (m, 2H).

Preparation 21

1-[4-(6-Oxaspiro[3.3]heptan-2-ylamino)-5-oxido-6,7-dihydrothieno[3,2-d]pyrimidin-5-ium-2-yl]azetidin-3-ol (Compound 078)

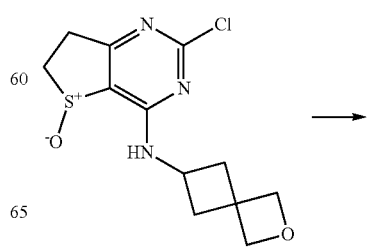

-continued

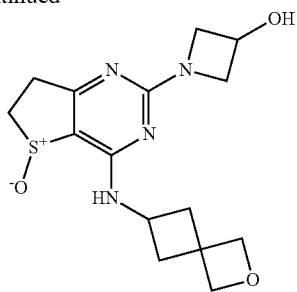

To a solution of 2-chloro-5-oxido-N-(6-oxaspiro[3.3]heptan-2-yl)-6,7-dihydrothieno-[3,2-d]pyrimidin-5-ium-4-amine (1.20 g, 4.0 mmol) in DMF (20 mL) was added azetidin-3-ol hydrochloride (460 mg, 4.20 mmol) and DIPEA (2.1 mL, 12 mmol). The mixture was stirred at room temperature overnight. Water (10 mL) was added and the pH of the solution was adjusted to 5 with acetic acid. Prep-HPLC purification afforded the title compound.

$^1$H NMR (DMSO-d6) δ: 7.81 (d, J=6.5 Hz, 1H), 5.65 (d, J=6.4 Hz, 1H), 4.62 (s, 2H), 4.57-4.42 (m, 3H), 4.34-4.14 (m, 3H), 3.74 (dd, J=9.7, 4.3 Hz, 2H), 3.40 (dd, J=17.1, 8.3 Hz, 1H), 3.19 (dt, J=13.5, 8.3 Hz, 1H), 2.98-2.80 (m, 2H), 2.64-2.52 (m, 2H), 2.37-2.22 (in, 2H).

HPLC-Retention time (XE Metode 7 CM): 1.51 minutes. Detected "M+1"-mass: 337.13.

The Examples 65-67 shown in Table 5 were prepared by reacting Compound 078 as described in the General Procedure with the appropriate acid:

TABLE 5

| Ex. | Cpd | Structure | IUPAC Name | HPLC Rt (min) | PDE4 IC$_{50}$ range | TNF-a IC$_{50}$ range |
|---|---|---|---|---|---|---|
| 65 | 079 | 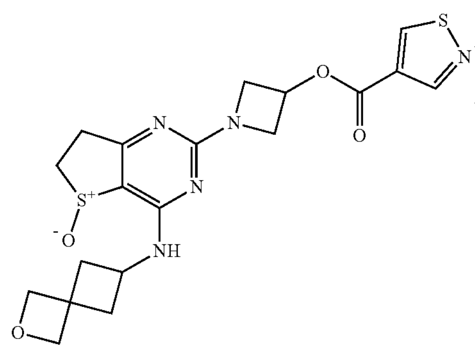 [SMILES: O=C(OC1CN(c2nc3c(c(NC4CC5(COC5)C4)n2)[S+](O)CC3)C1)c1cnsc1] | [1-[4-(6-oxaspiro[3.3]-heptan-2-ylamino)-5-oxido-6,7-dihydrothieno-[3,2-d]pyrimidin-5-ium-2-yl]azetidin-3-yl] isothiazole-4-carboxylate | 1.81 | * | * |
| 66 | 080 | 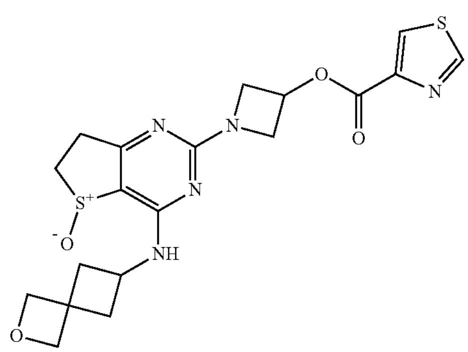 [SMILES: O=C(OC1CN(c2nc3c(c(NC4CC5(COC5)C4)n2)[S+](O)CC3)C1)c1cscn1] | [1-[4-(6-oxaspiro[3.3]-heptan-2-ylamino)-5-oxido-6,7-dihydrothieno-[3,2-d]pyrimidin-5-ium-2-yl]azetidin-3-yl] thiazole-4-carboxylate | 1.71 | * | * |
| 67 | 081 | 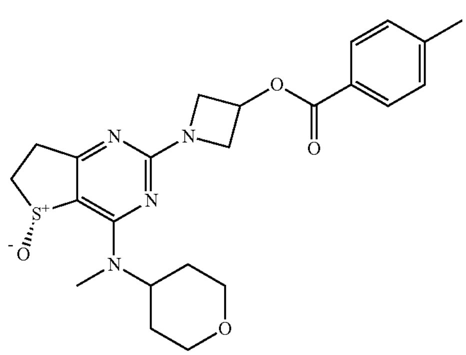 [SMILES: Cc1ccc(C(=O)OC2CN(c3nc4c(c(N(C)C5CCOCC5)n3)[S@+](O)CC4)C2)cc1] | [1-[4-(6-oxaspiro[3.3]-heptan-2-ylamino)-5-oxido-6,7-dihydro-thieno[3,2-d]pyrimidin-5-ium-2-yl]azetidin-3-yl] tetrahydropyran-4-carboxylate | 1.76 | * | * |

The Examples 68 and 69 in Table 6 were obtained by separating the two enantiomers of the [1-[4-(6-oxaspiro[3.3]heptan-2-ylamino)-5-oxido-6,7-dihydrothieno[3,2-d]-pyrimidin-5-ium-2-yl]azetidin-3-yl] isothiazole-4-carboxylate racemate using chiral SFC.

TABLE 6

| Ex. | Cpd | Structure | IUPAC Name | HPLC Rt (min) | PDE4 IC$_{50}$ range | TNF-α IC$_{50}$ range |
|---|---|---|---|---|---|---|
| 68 | 079a | OR Enantiomer | [1-[(5R)-4-(6-oxaspiro-[3.3]heptan-2-ylamino)-5-oxido-6,7-dihydrothieno-[3,2-d]pyrimidin-5-ium-2-yl]azetidin-3-yl] isothiazole-4-carboxylate (or enantiomer) | 1.81 | *** | *** |
| 69 | 039b | OR Enantiomer | [1-[(5S)-4-(6-oxaspiro-[3.3]heptan-2-ylamino)-5-oxido-6,7-dihydrothieno-[3,2-d]pyrimidin-5-ium-2-yl]azetidin-3-yl] isothiazole-4-carboxylate (or enantiomer) | 1.81 | ** | * |

The Examples 70 and 71 in Table 7 were obtained by separating the two enantiomers of the [1-[4-(6-oxaspiro[3.3]heptan-2-ylamino)-5-oxido-6,7-dihydrothieno[3,2-d]-pyrimidin-5-ium-2-yl]azetidin-3-yl] thiazole-4-carboxylate racemate using chiral SFC.

TABLE 7

| Ex. | Cpd | Structure | IUPAC Name | HPLC Rt (min) | PDE4 IC$_{50}$ range | TNF-α IC$_{50}$ range |
|---|---|---|---|---|---|---|
| 70 | 080a | OR Enantiomer | [1-[(5R)-4-(6-oxaspiro-[3.3]heptan-2-ylamino)-5-oxido-6,7-dihydrothieno-[3,2-d]pyrimidin-5-ium-2-yl]azetidin-3-yl] thiazole-4-carboxylate (or enantiomer) | 1.71 | *** | *** |
| 71 | 080b | OR Enantiomer | [1-[(5S)-4-(6-oxaspiro-[3.3]heptan-2-ylamino)-5-oxido-6,7-dihydrothieno-[3,2-d]pyrimidin-5-ium-2-yl]azetidin-3-yl] thiazole-4-carboxylate (or enantiomer) | 1.71 | ** | * |

Preparation 22

1-[(3S)-3-[(2-Chloro-6,7-dihydrothieno[3,2-d]pyrimidin-4-yl)amino]pyrrolidin-1-yl]ethanone (Compound 082)

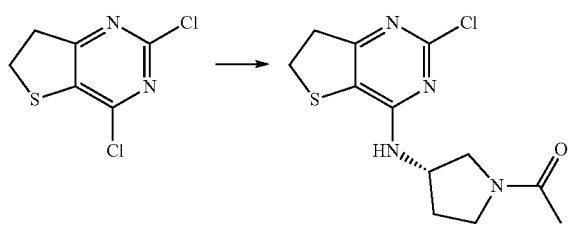 [SMILES: Clc1nc(Cl)c2c(n1)CCS2 ; CC(=O)N1CC[C@H](Nc2nc(Cl)nc3c2SCC3)C1]

To a solution of 1-[(3S)-3-aminopyrrolidin-1-yl]ethanone trifluoroacetic acid (5.26 g, 21.7 mmol) in DMF (15 mL) was added DIPEA (25 mL, 143 mmol) and 2,4-dichloro-6,7-dihydrothieno[3,2-d]pyrimidine (3.00 g, 14.5 mmol). The reaction mixture was heated to 100° C. overnight, before it was cooled to room temperature, diluted with water (50 mL) and extracted three times with DCM (3×50 mL). The combined organic phases were washed with water (20 mL), dried over MgSO$_4$ and filtered. Evaporation to dryness afforded the title compound.

$^1$H NMR (CDCl$_3$) δ: 4.85-4.63 (m, 1H), 4.48 (t, J=7.0 Hz, 1H), 3.97-3.78 (m, 1H), 3.76-3.52 (m, 2H), 3.50-3.20 (m, 4H), 2.47-2.19 (m, 1H), 2.16-1.81 (m, 4H), 1.50-1.36 (m, 1H).

Preparation 23

1-[(3S)-3-[(2-Chloro-5-oxido-6,7-dihydrothieno[3,2-d]pyrimidin-5-ium-4-yl)amino]pyrrolidin-1-yl]ethanone (Compound 083)

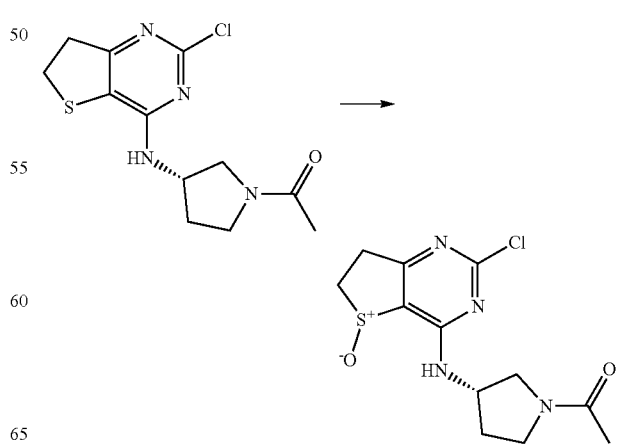

Hydrogen peroxide (27.5%) (1.67 mL, 13.5 mmol) was added to a mixture of 1-[(3S)-3-[(2-chloro-6,7-dihydrothieno[3,2-d]pyrimidin-4-yl)amino]pyrrolidin-1-yl]ethanone (2.68 g, 8.97 mmol) in acetic acid (9.0 mL). The reaction mixture was stirred at room temperature for 1 hour before it was diluted with water (20 mL) and extracted twice with DCM (2×30 mL). Evaporation of the combined organic phases afforded the title compound as beige foam.

$^1$H NMR (DMSO-d6) δ: 8.88 (d, J=6.3 Hz, 1H), 4.86-4.46 (m, 1H), 3.83-3.24 (m, 4H), 3.24-2.99 (m, 2H), 2.30-1.96 (m, 2H), 1.96-1.89 (m, 5H)

Preparation 24

1-[(3S)-3-[[2-(3-Hydroxyazetidin-1-yl)-5-oxido-6,7-dihydrothieno[3,2-d]pyrimidin-5-ium-4-yl]amino]pyrrolidin-1-yl]ethanone (Compound 084)

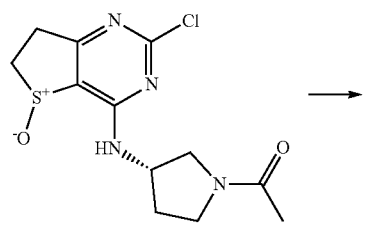

→

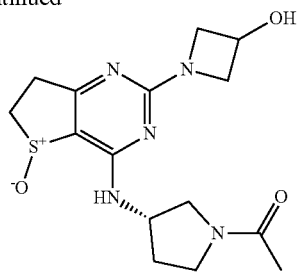

To a solution of 1-[(3S)-3-[(2-chloro-5-oxido-6,7-dihydrothieno[3,2-d]pyrimidin-5-ium-4-yl)amino]pyrrolidin-1-yl]ethanone (20 mg, 64 μmol) in DMF (0.4 mL) was added a solution of azetidin-3-ol hydrochloride (21.4 mg, 195 μmol) in DMF (0.5 mL) and DIPEA (55 μL, 0.32 mmol). The mixture was shaken at 40° C. overnight. Prep.

LCMS purification afforded the title compound.

HPLC-Retention time (XE Metode 7 CM): 1.47 minutes.

Detected "M+1"-mass: 352.14

The Examples 72-74 shown in Table 8 were prepared by reacting Compound 084 as described in the General Procedure with the appropriate acid:

TABLE 8

| Ex. | Cpd | Structure | IUPAC Name | HPLC Rt (min) | PDE4 IC$_{50}$ range | TNF-α IC$_{50}$ range |
|---|---|---|---|---|---|---|
| 72 | 085 | 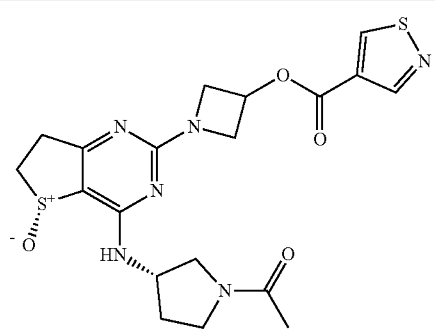 [SMILES: CC(=O)N1CC[C@H](Nc2nc(N3CC(OC(=O)c4cnsc4)C3)nc3c2[S@+](O)CC3)C1] | [1-[4-[[(3S)-1-acetyl-pyrrolidin-3-yl]amino]-5-oxido-6,7-dihydro-thieno[3,2-d]pyrimidin-5-ium-2-yl]azetidin-3-yl]isothiazole-4-carboxylate | 1.74 | * | * |
| 73 | 086 | 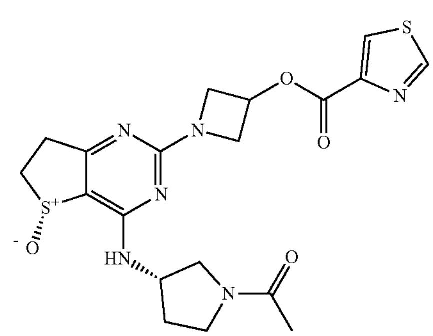 [SMILES: CC(=O)N1CC[C@H](Nc2nc(N3CC(OC(=O)c4cscn4)C3)nc3c2[S@+](O)CC3)C1] | [1-[4-[[(3S)-1-acetyl-pyrrolidin-3-yl]amino]-5-oxido-6,7-dihydro-thieno[3,2-d]pyrimidin-5-ium-2-yl]azetidin-3-yl]thiazole-4-carboxylate | 1.65 | * |  |

TABLE 8-continued

| Ex. | Cpd | Structure | IUPAC Name | HPLC Rt (min) | PDE4 IC$_{50}$ range | TNF-α IC$_{50}$ range |
|---|---|---|---|---|---|---|
| 74 | 087 | 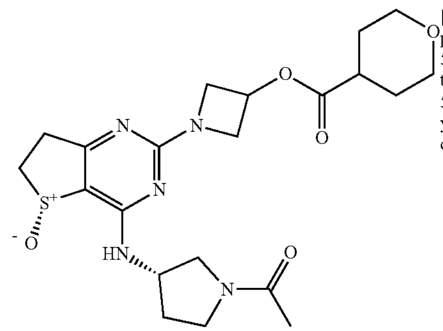 | [1-[4-[[(3S)-1-acetyl-pyrrolidin-3-yl]amino]-5-oxido-6,7-dihydro-thieno[3,2-d]pyrimidin-5-ium-2-yl]azetidin-3-yl]tetrahydropyran-4-carboxylate | 1.70 | * |  |

Preparation 25

1-[(3R)-3-[(2-Chloro-6,7-dihydrothieno[3,2-d]pyrimidin-4-yl)amino]pyrrolidin-1-yl]ethanone (Compound 088)

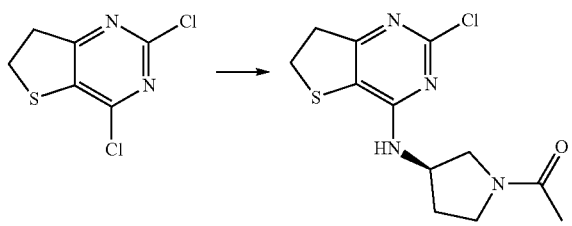 [SMILES: Clc1nc(Cl)c2c(n1)CCS2 ; CC(=O)N1CC[C@@H](Nc2nc(Cl)nc3c2SCC3)C1]

To a solution of 1-[(3R)-3-aminopyrrolidin-1-yl]ethanone trifluoroacetic acid (5.26 g, 21.7 mmol) in DMF (15 mL) was added DIPEA (25 mL, 143 mmol) and 2,4-dichloro-6,7-dihydrothieno[3,2-d]pyrimidine (3.00 g, 14.5 mmol). The reaction mixture was heated to 100° C. overnight, before it was cooled to room temperature, diluted with water (50 mL) and extracted three times with DCM (3×50 mL). The combined organic phases were washed with water (20 mL), dried over MgSO$_4$ and filtered. Evaporation to dryness afforded the title compound.

$^1$H NMR (CDCl$_3$) δ: 4.86-4.63 (m, 1H), 4.53 (dd, J=12.9, 6.8 Hz, 1H), 3.98-3.78 (m, 1H), 3.75-3.53 (m, 2H), 3.52-3.20 (m, 4H), 2.47-2.20 (m, 1H), 2.17-1.82 (m, 4H), 1.62 (s, 1H).

Preparation 26

1-[(3R)-3-[(2-Chloro-5-oxido-6,7-dihydrothieno[3,2-d]pyrimidin-5-ium-4-yl)amino]pyrrolidin-1-yl]ethanone (Compound 089)

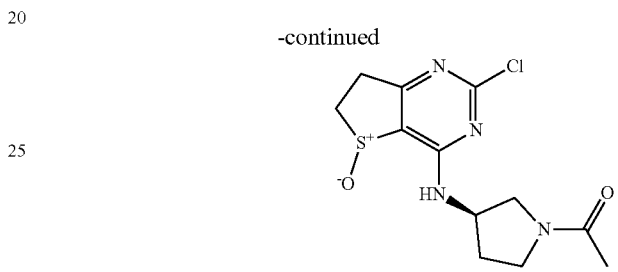

Hydrogen peroxide (27.5%) (1.26 mL, 10.2 mmol) was added to a mixture of 1-[(3R)-3-[(2-chloro-6,7-dihydrothieno[3,2-d]pyrimidin-4-yl)amino]pyrrolidin-1-yl]ethanone (2.03 g, 6.79 mmol) in acetic acid (6.8 mL). The reaction mixture was stirred at room temperature for 1 hour before it was diluted with water (20 mL) and extracted twice with DCM (2×30 mL). Evaporation of the combined organic phases afforded the title compound as beige foam.

$^1$H NMR (DMSO-d6) δ: 8.88 (d, J=6.3 Hz, 1H), 4.81-4.46 (m, 1H), 3.87-3.25 (m, 4H), 3.24-2.99 (m, 2H), 2.33-1.95 (m, 2H), 1.95-1.88 (m, 5H).

Preparation 27

1-[(3R)-3-[[2-(3-Hydroxyazetidin-1-yl)-5-oxido-6,7-dihydrothieno[3,2-d]pyrimidin-5-ium-4-yl]amino]pyrrolidin-1-yl]ethanone (Compound 090)

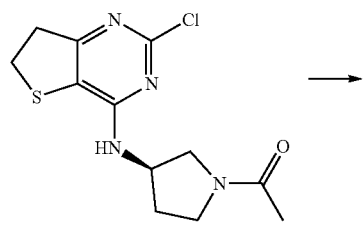

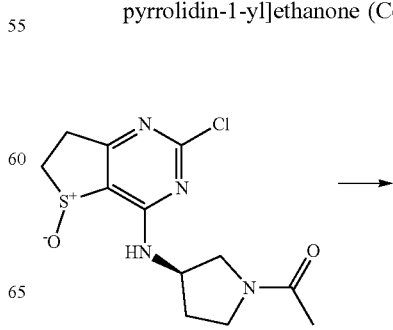

-continued

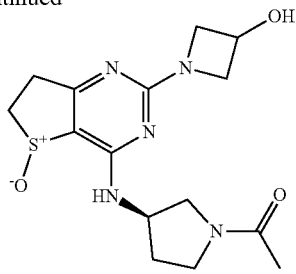

To a solution of 1-[(3R)-3-[(2-chloro-5-oxido-6,7-dihydrothieno[3,2-d]pyrimidin-5-ium-4-yl)amino]pyrrolidin-1-yl]ethanone (20 mg, 64 μmol) in DMF (0.4 mL) was added a solution of azetidin-3-ol hydrochloride (21.4 mg, 195 μmol) in DMF (0.5 mL) and DIPEA (55 μL, 0.32 mmol). The mixture was shaken at 40° C. overnight. Prep. LCMS purification afforded the title compound.

Example 75 shown in Table 9 was prepared by reacting Compound 090 as described in the General Procedure with tetrahydropyran-4-carboxylic acid:

$^1$H NMR (CDCl$_3$) δ: 4.66-4.51 (m, 1H), 4.38-4.18 (m, 2H), 3.89-3.76 (m, 1H), 3.49-3.37 (m, 2H), 3.33-3.16 (m, 3H), 2.86-2.72 (m, 1H), 2.23-1.98 (m, 5H), 1.51-1.28 (m, 2H).

Preparation 29

1-[4-[(2-Chloro-5-oxido-6,7-dihydrothieno[3,2-d]pyrimidin-5-ium-4-yl)amino]-1-piperidyl]ethanone (Compound 093)

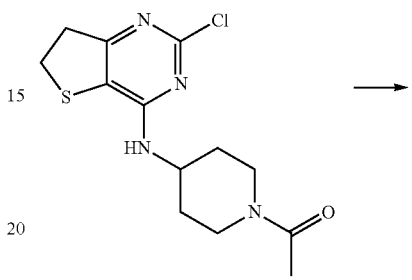

TABLE 9

| Ex. | Cpd | Structure | IUPAC Name | HPLC Rt (min) | PDE4 IC$_{50}$ range | TNF-α IC$_{50}$ range |
|---|---|---|---|---|---|---|
| 75 | 091 | 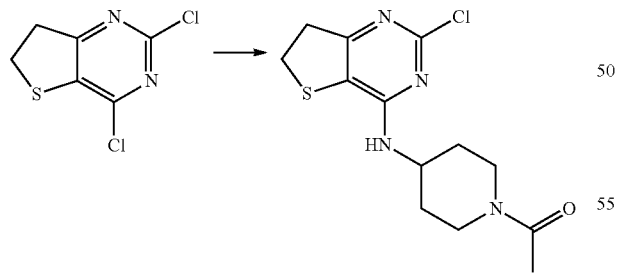 | [1-[4-[[(3R)-1-acetylpyrrolidin-3-yl]amino]-5-oxido-6,7-dihydrothieno[3,2-d]pyrimidin-5-ium-2-yl]azetidin-3-yl] tetrahydropyran-4-carboxylate | 1.70 | * | * |

Preparation 28

1-[4-[(2-Chloro-6,7-dihydrothieno[3,2-d]pyrimidin-4-yl)amino]-1-piperidyl]ethanone (Compound 092)

To a solution of 1-(4-amino-1-piperidyl)ethanone (3.09 g, 21.7 mmol) in DMF (10 mL) was added DIPEA (5.05 mL, 29.0 mmol) and 2,4-dichloro-6,7-dihydrothieno[3,2-d]pyrimidine (3.00 g, 14.5 mmol). The reaction mixture was heated to 50° C. overnight. The obtained suspension was cooled to room temperature, diluted with water (50 mL). Filtration and subsequent washings with water (2×10 mL) and TBME:heptane (3:1) (2×5 mL) afforded the title compound as solid material.

-continued

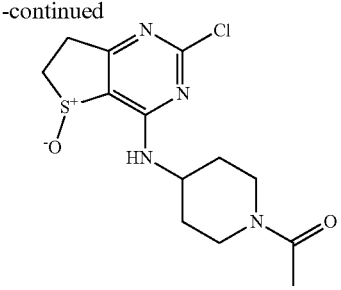

Hydrogen peroxide (27.5%) (2.04 mL, 16.5 mmol) was added to a mixture of 1-[4-[(2-chloro-6,7-dihydrothieno[3,2-d]pyrimidin-4-yl)amino]-1-piperidyl]ethanone (3.44 g, 11.0 mmol) in acetic acid (11 mL). The reaction mixture was stirred at room temperature for 1 hour before it was diluted with water (20 mL), extracted twice with DCM (2×30 mL) and evaporated to dryness. Crystallization from TBME afforded the title compound as crystalline powder.

$^1$H NMR (DMSO-d6) δ: 8.56 (d, J=7.7 Hz, 1H), 4.48-4.14 (m, 2H), 3.85 (d, J=13.8 Hz, 1H), 3.57 (dt, 1H), 3.39 (dt,

3=14.0, 8.2 Hz, 2H), 3.23-2.96 (m, 3H), 2.70-2.55 (m, 1H), 2.01 (d, 3=1.7 Hz, 3H), 1.93-1.69 (m, 2H), 1.68-1.33 (m, 1H).

Preparation 30

1-[4-[[2-(3-Hydroxyazetidin-1-yl)-5-oxido-6,7-dihydrothieno[3,2-d]pyrimidin-5-ium-4-yl]amino]-1-piperidyl]ethanone (Compound 094)

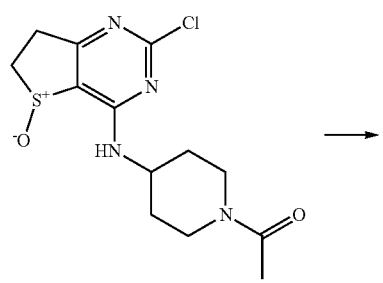

→

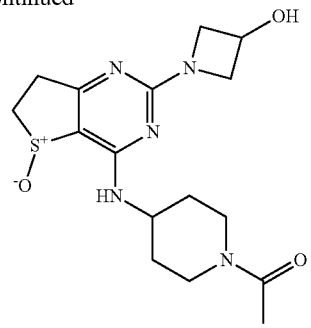

To a solution of 1-[4-[(2-chloro-5-oxido-6,7-dihydrothieno[3,2-d]pyrimidin-5-ium-4-yl)amino]-1-piperidyl]ethanone (20 mg, 61 μmol) in DMF (0.4 mL) was added a solution of azetidin-3-ol hydrochloride (21.4 mg, 195 μmol) in DMF (0.5 mL) and DIPEA (55 μL, 0.32 mmol). The mixture was shaken at 40° C. overnight. Prep. LCMS purification afforded the title compound.

HPLC-Retention time (XE Metode 7 CM): 1.49 minutes. Detected "M+1"-mass: 366.16

The Examples 76 and 77 shown in Table 10 were prepared by reacting Compound 094 as described in the General Procedure with the appropriate acid:

TABLE 10

| Ex. | Cpd | Structure | IUPAC Name | HPLC Rt (min) | PDE4 IC$_{50}$ range | TNF-α IC$_{50}$ range |
|---|---|---|---|---|---|---|
| 76 | 095 | 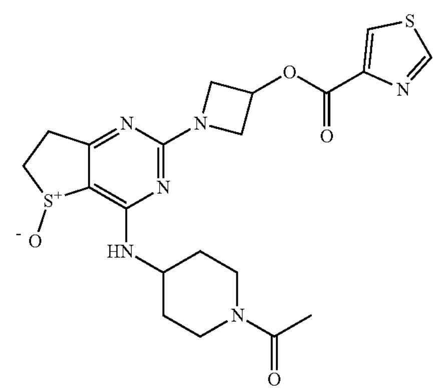 [SMILES: CC(=O)N1CCC(Nc2nc(N3CC(OC(=O)c4cscn4)C3)nc3c2[S+](O)CC3)CC1] | [1-[4-[(1-acetyl-4-piperidyl)amino]-5-oxido-6,7-dihydrothieno[3,2-d]pyrimidin-5-ium-2-yl]-azetidin-3-yl] thiazole-4-carboxylate | 1.67 | ** | * |
| 77 | 096 | 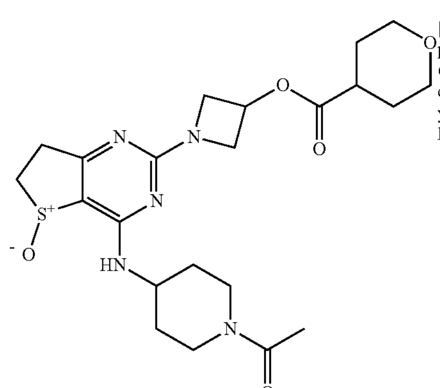 | [1-[4-[(1-acetyl-4-piperidyl)amino]-5-oxido-6,7-dihydrothieno[3,2-d]pyrimidin-5-ium-2-yl]azetidin-3-yl] tetrahydropyran-4-carboxylate | 1.72 |  |  |

CLAUSES

In view of the description the present inventors have in particular provided:

Clause 1. A compound of general formula (I)

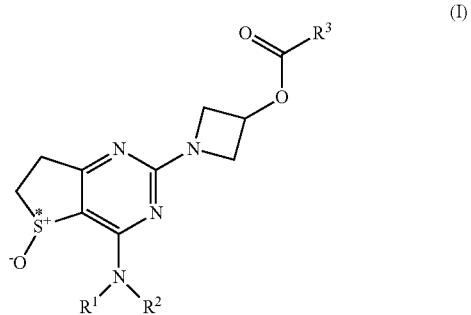

wherein $R^1$ is hydrogen or $(C_1-C_4)$alkyl; and
wherein $R^2$ is selected from the group consisting of tetrahydropyranyl, oxaspiro-heptanyl, pyrrolidinyl and piperidinyl; wherein said pyrrolidinyl and piperidinyl are optionally substituted with one or more substituents independently selected from $R^4$; and
wherein $R^4$ is selected from the group consisting of —C(O) $(C_1-C_4)$alkyl, $(C_1-C_4)$alkyl, —S(O)$_2$R$_x$, —S(O)$_2$NR$_a$R$_b$, —C(O)O(C$_1$-C$_5$)alkyl, —C(O)NR$_a$R$_b$ and —(C$_1$-C$_4$)alkyl-C(O)NR$_a$R$_b$; and
wherein $R_a$ and $R_b$ are independently selected from the group consisting of hydrogen, $(C_1-C_4)$alkyl and halo$(C_1-C_4)$alkyl, or
$R_a$ and $R_b$ may together with the nitrogen atom to which they are attached form a (4-6)membered heterocycloalkyl, wherein said heterocycloalkyl is optionally substituted with one or more $(C_1-C_4)$alkyl; and
wherein $R^3$ is selected from the group consisting of $(C_1-C_6)$ alkyl, $(C_3-C_6)$cycloalkyl, $(C_1-C_4)$alkyl$(C_3-C_6)$cycloalkyl, halo$(C_1-C_6)$alkyl, $(C_1-C_6)$alkoxy, $(C_1-C_6)$alkyl$(C_1-C_6)$ alkoxy, halo$(C_1-C_4)$alkyloxy, (4-6)membered heterocycloalkyl, $(C_1-C_4)$alkyl(4-6)membered heterocycloalkyl, (5-6) membered heteroaryl, $(C_1-C_4)$alkyl(5-6)membered heteroaryl, aryl and $(C_1-C_4)$alkylaryl; wherein said alkyl, cycloalkyl, heterocycloalkyl, heteroaryl and aryl are optionally substituted with one or more substituents independently selected from $R^5$; and
wherein $R^5$ is selected from the group consisting of halogen, cyano, hydroxyl, $(C_1-C_4)$-alkyl, halo$(C_1-C_4)$alkyl, halo$(C_1-C_4)$alkyloxy, OR$_x$, —SR$_x$, —S(O)$_2$R$_x$, —S(O)$_2$NR$_a$R$_b$, —C(O)R$_x$, —C(O)(OR$_x$), and —C(O)NR$_a$R$_b$; and
wherein R$_x$ consist of $(C_1-C_4)$alkyl, $(C_3-C_6)$cycloalkyl, heterocycloalkyl; and
wherein S* represent a chiral sulphur atom; and
pharmaceutically acceptable salts, enantiomers, mixtures of enantiomers, diastereomers, mixtures of diastereomers, hydrates and solvates thereof.

Clause 2. A compound according to clause 1, wherein $R^1$ is hydrogen or $(C_1-C_4)$alkyl; and
$R^2$ is selected from the group consisting of tetrahydropyranyl, oxaspiroheptanyl, pyrrolidinyl and piperidinyl; wherein said pyrrolidinyl and piperidinyl are optionally substituted with one or more substituents independently selected from $R^4$; and
$R^4$ is selected from the group consisting of —C(O)(C$_1$-C$_4$) alkyl, $(C_1-C_4)$alkyl, —C(O)O(C$_1$-C$_6$)alkyl, —C(O)NR$_a$R$_b$ and —(C$_1$-C$_4$)alkyl-C(O)NR$_a$R$_b$; and $R_a$ and $R_b$ are independently selected from the group consisting of hydrogen, $(C_1-C_4)$alkyl and halo$(C_1-C_4)$alkyl, or
$R_a$ and $R_b$ may together with the nitrogen atom to which they are attached form a (4-6)membered heterocycloalkyl, wherein said heterocycloalkyl is optionally substituted with one or more $(C_1-C_4)$alkyl; and
$R^3$ is selected from the group consisting of $(C_1-C_6)$alkyl, $(C_3-C_6)$cycloalkyl, $(C_1-C_4)$alkyl$(C_3-C_6)$cycloalkyl, halo $(C_1-C_6)$alkyl, $(C_1-C_6)$alkoxy, $(C_1-C_6)$alkyl$(C_1-C_6)$alkoxy, halo$(C_1-C_4)$alkyloxy, (4-6)membered heterocycloalkyl, $(C_1-C_4)$alkyl(4-6)membered heterocycloalkyl, (5-6)membered heteroaryl, $(C_1-C_4)$alkyl(5-6)membered heteroaryl, aryl and $(C_1-C_4)$alkylaryl; wherein said heterocycloalkyl, heteroaryl and aryl are optionally substituted with one or more substituents independently selected from $R^5$; and
$R^5$ is selected from the group consisting of halogen, cyano, hydroxyl, $(C_1-C_4)$alkyl, halo$(C_1-C_4)$alkyl, halo$(C_1-C_4)$alkyloxy, OR$_x$, —SR$_x$, —S(O)$_2$R$_x$, —S(O)$_2$NR$_a$R$_b$, —C(O)(C$_1$-C$_6$)alkyl, —C(O)(OR$_x$), and —C(O)NR$_a$R$_b$; and
R$_x$ is $(C_1-C_4)$alkyl; and
S* represent a chiral sulphur atom; and
pharmaceutically acceptable salts, enantiomers, mixtures of enantiomers, diastereomers, mixtures of diastereomers, hydrates and solvates thereof.

Clause 3. A compound according to clause 1 or 2, wherein $R^1$ is hydrogen.

Clause 4. A compound according to clause 1 or 2, wherein $R^1$ is $(C_1-C_4)$alkyl.

Clause 5. A compound according to clause 4, wherein $R^1$ is methyl.

Clause 6. A compound according to any one of the preceding clauses, wherein $R^1$ is hydrogen or methyl, and $R^2$ is tetrahydropyranyl.

Clause 7. A compound according to any one of the clauses 1-5, wherein $R^1$ is hydrogen or methyl, and $R^2$ is oxaspiroheptanyl.

Clause 8. A compound according to any one of the clauses 1-5, wherein $R^1$ is hydrogen or methyl, and $R^2$ is pyrrolidinyl, optionally substituted with one or more substituents independently selected from $R^4$.

Clause 9. A compound according to clause 7, wherein $R^1$ is hydrogen or methyl, and $R^2$ is pyrrolidinyl substituted with —C(O)(C$_1$-C$_4$)alkyl.

Clause 10. A compound according to any one of the clauses 1-5, wherein $R^1$ is hydrogen or methyl, and $R^2$ is piperidinyl, optionally substituted with one or more substituents independently selected from $R^4$.

Clause 11. A compound according to clause 10, wherein $R^1$ is hydrogen or methyl, and $R^2$ is piperidinyl substituted with —C(O)(C$_1$-C$_4$)alkyl.

Clause 12. A compound according to any one of the preceding clauses, wherein $R^3$ is selected from the group consisting of $(C_3-C_6)$cycloalkyl, (4-6)membered hetero-cycloalkyl, (5-6)membered heteroaryl and aryl.

Clause 13. A compound according to clause 12, wherein $R^3$ is a (4-6)membered heterocycloalkyl, e.g. tetrahydropyranyl.

Clause 14. A compound according to clause 12, wherein $R^3$ is a (5-6)membered heteroaryl, e.g. isothiazolyl, thiazolyl.

Clause 15. A compound according to clause 14, wherein $R^3$ is 4-isothiazolyl, 4-thiazolyl.

Clause 16. A compound according to any one of the clauses 1-5, 8-15, wherein $R^4$ is —C(O)(C$_1$-C$_4$)alkyl.

Clause 17. A compound according to clause 16, wherein $R^4$ is —C(O)-methyl.

Clause 18. A compound according to any one of the clauses 1-5, 8-15, wherein $R^4$ is —C(O)O($C_1$-$C_4$)alkyl.

Clause 19. A compound according to any one of the clauses 1-15, wherein $R^4$ is —($C_1$-$C_4$)alkyl-C(O)$NR_aR_b$; wherein $R_a$ and $R_b$ are independently selected from the group consisting of hydrogen, ($C_1$-$C_4$)alkyl, or $R_a$ and $R_b$ may together with the nitrogen atom to which they are attached form a (4-6)membered heterocycloalkyl, wherein said heterocycloalkyl is optionally substituted with one or more ($C_1$-$C_4$)alkyl.

Clause 20. A compound according to any one of the preceding clauses, wherein R' is hydrogen or ($C_1$-$C_4$)alkyl; and $R^2$ is selected from the group consisting of tetrahydropyranyl, oxaspiroheptanyl, pyrrolidinyl and piperidinyl; wherein said pyrrolidinyl and piperidinyl are optionally substituted with $R^4$; and $R^4$ is selected from the group consisting of —C(O)($C_1$-$C_4$)alkyl, ($C_1$-$C_4$)alkyl, —C(O)O($C_1$-$C_6$)alkyl, —C(O)$NR_aR_b$ and —($C_1$-$C_4$)alkyl-C(O)$NR_aR_b$; and $R^3$ is selected from the group consisting of ($C_1$-$C_6$)alkyl, ($C_3$-$C_6$)cycloalkyl, ($C_1$-$C_4$)alkyl($C_3$-$C_6$)cycloalkyl, halo($C_1$-$C_6$)alkyl, ($C_1$-$C_6$)alkoxy, ($C_1$-$C_6$)alkyl($C_1$-$C_6$)alkoxy, halo($C_1$-$C_4$)alkyloxy, (4-6)membered heterocycloalkyl, ($C_1$-$C_4$)-alkyl(4-6)membered heterocycloalkyl, (5-6)membered heteroaryl, ($C_1$-$C_4$)alkyl(5-6)-membered heteroaryl, aryl and ($C_1$-$C_4$)alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, cyano, hydroxyl, ($C_1$-$C_4$)alkyl, halo($C_1$-$C_4$)alkyl and halo($C_1$-$C_4$)-alkyloxy, $OR_x$, —$SR_x$, —$S(O)_2R_x$, —$S(O)_2NR_aR_b$, —C(O)($C_1$-$C_6$)alkyl, —C(O)($OR_x$), and —C(O)$NR_aR_b$; and $R_x$ consist of ($C_1$-$C_4$)alkyl, ($C_3$-$C_6$)cycloalkyl; and $R_a$ and $R_b$ are independently selected from the group consisting of hydrogen, ($C_1$-$C_4$)alkyl and halo($C_1$-$C_4$)alkyl, or $R_a$ and $R_b$ may together with the nitrogen atom to which they are attached form a (4-6)membered heterocycloalkyl, wherein said heterocycloalkyl is optionally substituted with one or more ($C_1$-$C_4$)alkyl.

Clause 21. A compound according to clause 20, wherein $R^1$ is hydrogen or ($C_1$-$C_4$)-alkyl; and $R^2$ is selected from the group consisting of tetrahydropyranyl, oxaspiro-heptanyl, pyrrolidinyl and piperidinyl, wherein said pyrrolidinyl and piperidinyl are is optionally substituted with $R^4$; and $R^4$ is selected from the group consisting of —C(O)—($C_1$-$C_4$) alkyl, and —C(O)O($C_1$-$C_4$)alkyl; and $R^3$ is selected from the group consisting of ($C_3$-$C_6$)cycloalkyl, (4-6)membered heterocycloalkyl, and (5-6)membered heteroaryl, all of which are optionally substituted with one or more substituents independently selected from $R^5$; and $R^5$ is selected from the group consisting of halogen, cyano, hydroxyl, ($C_1$-$C_4$)alkyl, halo($C_1$-$C_4$)alkyl and halo($C_1$-$C_4$)alkyloxy, $OR_x$, —$SR_x$, —$S(O)_2R_x$, —$S(O)_2NR_aR_b$, —C(O)($C_1$-$C_6$)alkyl, —C(O)($OR_x$), and —C(O)$NR_aR_b$; and $R_x$ consist of ($C_1$-$C_4$)alkyl, ($C_3$-$C_6$)cycloalkyl; and $R_a$ and $R_b$ are independently selected from the group consisting of hydrogen, ($C_1$-$C_4$)alkyl and halo($C_1$-$C_4$)alkyl, or $R_a$ and $R_b$ may together with the nitrogen atom to which they are attached form a (4-6)membered heterocycloalkyl, wherein said heterocycloalkyl is optionally substituted with one or more ($C_1$-$C_4$)alkyl.

Clause 22. A compound according to clause 21, wherein $R^1$ is hydrogen or ($C_1$-$C_4$)alkyl; and $R^2$ is selected from the group consisting of tetrahydropyranyl, oxaspiro-heptanyl, pyrrolidinyl and piperidinyl, wherein said pyrrolidinyl and piperidinyl are optionally substituted with —C(O)($C_1$-$C_4$)alkyl; and $R^3$ is selected from the group consisting of ($C_3$-$C_6$)cycloalkyl, (4-6)membered heterocycloalkyl, and (5-6)membered heteroaryl.

Clause 23. A compound according to any one of the preceding clauses 1-19, wherein $R^1$ is hydrogen or ($C_1$-$C_4$) alkyl; and $R^2$ is oxaspiroheptanyl; and wherein $R^3$ is selected from the group consisting of ($C_1$-$C_6$)alkyl, ($C_3$-$C_6$)cycloalkyl, ($C_1$-$C_4$)alkyl($C_3$-$C_6$)cycloalkyl, halo($C_1$-$C_6$)alkyl, ($C_1$-$C_6$)alkoxy, ($C_1$-$C_6$)alkyl($C_1$-$C_6$)alkoxy, halo($C_1$-$C_4$)alkyloxy, (4-6)membered heterocycloalkyl, ($C_1$-$C_4$)alkyl(4-6)membered heterocycloalkyl, (5-6)-membered heteroaryl, ($C_1$-$C_4$)alkyl(5-6)membered heteroaryl, aryl and ($C_1$-$C_4$) alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, cyano, hydroxyl, ($C_1$-$C_4$)alkyl, halo($C_1$-$C_4$)alkyl and halo($C_1$-$C_4$) alkyloxy, $OR_x$, $SR_x$, —$S(O)_2R_x$, —$S(O)_2NR_aR_b$, —C(O)($C_1$-$C_6$)alkyl, —C(O)($OR_x$), and —C(O)$NR_aR_b$; and $R_x$ consist of ($C_1$-$C_4$)alkyl, ($C_3$-$C_6$)cycloalkyl; and $R_a$ and $R_b$ are independently selected from the group consisting of hydrogen, ($C_1$-$C_4$)alkyl and halo($C_1$-$C_4$)alkyl, or $R_a$ and $R_b$ may together with the nitrogen atom to which they are attached form a (4-6)membered heterocycloalkyl, wherein said heterocycloalkyl is optionally substituted with one or more ($C_1$-$C_4$)alkyl.

Clause 24. A compound according to clause 23, wherein $R^1$ is hydrogen or ($C_1$-$C_4$)-alkyl; and $R^2$ is oxaspiroheptanyl; and $R^3$ is selected from the group consisting of ($C_3$-$C_6$) cycloalkyl, (4-6)membered heterocycloalkyl, and (5-6) membered heteroalkyl, all of which are optionally substituted with one or more substituents independently selected from $R^5$; and $R^5$ is selected from the group consisting of halogen, cyano, hydroxyl, ($C_1$-$C_4$)alkyl, halo($C_1$-$C_4$)alkyl and halo ($C_1$-$C_4$)alkyloxy, $OR_x$, $SR_x$, —$S(O)_2R_x$, —$S(O)_2$—$NR_aR_b$, —C(O)($C_1$-$C_6$)alkyl, —C(O)($OR_x$), and —C(O)$NR_aR_b$; and $R_x$ consist of ($C_1$-$C_4$)alkyl, ($C_3$-$C_6$)cycloalkyl; and $R_a$ and $R_b$ are independently selected from the group consisting of hydrogen, ($C_1$-$C_4$)alkyl and halo($C_1$-$C_4$)alkyl, or $R_a$ and $R_b$ may together with the nitrogen atom to which they are attached form a (4-6)membered heterocycloalkyl, wherein said heterocycloalkyl is optionally substituted with one or more ($C_1$-$C_4$)alkyl.

Clause 25. A compound according to clause 24, wherein $R^1$ is hydrogen or ($C_1$-$C_4$)alkyl; and $R^2$ is oxaspiroheptanyl; and $R^3$ is selected from the group consisting of ($C_3$-$C_6$) cycloalkyl, (4-6)membered heterocycloalkyl, and (5-6) membered heteroaryl.

Clause 26. A compound according to clause 25, wherein $R^1$ is hydrogen; and $R^2$ is oxaspiroheptanyl; and $R^3$ is selected from the group consisting of (4-6)membered heterocycloalkyl, and (5-6)membered heteroaryl.

Clause 27 A compound according to any one of the preceding clauses 1-19, wherein $R^1$ is hydrogen or ($C_1$-$C_4$) alkyl; and $R^2$ is pyrrolidinyl, which is optionally substituted with $R^4$; and $R^4$ is selected from the group consisting of —C(O)($C_1$-$C_4$)alkyl, ($C_1$-$C_4$)-alkyl, —C(O)O($C_1$-$C_6$)alkyl, —C(O)$NR_aR_b$ and —($C_1$-$C_4$)alkyl-C(O)$NR_aR_b$; and $R^3$ is selected from the group consisting of ($C_1$-$C_6$)alkyl, ($C_3$-$C_6$) cycloalkyl, ($C_1$-$C_4$)alkyl($C_3$-$C_6$)cycloalkyl, halo($C_1$-$C_6$)alkyl, ($C_1$-$C_6$)alkoxy, ($C_1$-$C_6$)alkyl($C_1$-$C_6$)alkoxy, halo($C_1$-$C_4$)alkyloxy, (4-6)membered heterocycloalkyl, ($C_1$-$C_4$)alkyl (4-6)membered hetero-cycloalkyl, (5-6)membered heteroaryl, ($C_1$-$C_4$)alkyl(5-6)membered heteroaryl, aryl and ($C_1$-$C_4$)alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, cyano, hydroxyl, ($C_1$-$C_4$)alkyl, halo($C_1$-$C_4$)alkyl and halo ($C_1$-$C_4$)alkyloxy, $OR_x$, —$SR_x$, —$S(O)_2R_x$, —$S(O)_2NR_aR_b$, —C(O)(C₁-C₆)alkyl, —C(O)(ORₓ), and —C(O)NRₐR_b; and Rₓ consist of (C₁-C₄)alkyl, (C₃-C₆)cycloalkyl; and Rₐ and R_b are independently selected from the group consisting of hydrogen, (C₁-C₄)alkyl and halo(C₁-C₄)alkyl, or Rₐ and R_b may together with the nitrogen atom to which they are attached form a (4-6)membered heterocycloalkyl, wherein said heterocycloalkyl is optionally substituted with one or more (C₁-C₄)alkyl.

Clause 28. A compound according to clause 27, wherein $R^1$ is hydrogen or (C₁-C₄)-alkyl; and $R^2$ is pyrrolidinyl, wherein said pyrrolidinyl is optionally substituted with $R^4$; and $R^4$ is selected from the group consisting of —C(O)(C₁-C₄)alkyl, and —C(O)O(C₁-C₄)-alkyl; and $R^3$ is selected from the group consisting of (C₃-C₆)cycloalkyl, (4-6)-membered heterocycloalkyl, and (5-6)membered heteroaryl, all of which are optionally substituted with one or more substituents independently selected from $R^5$; and $R^5$ is selected from the group consisting of halogen, cyano, hydroxyl, (C₁-C₄)alkyl, halo(C₁-C₄)alkyl and halo(C₁-C₄)alkyloxy, ORₓ, —SRₓ, —S(O)₂Rₓ, —S(O)₂NRₐR_b, —C(O)(C₁-C₆)alkyl, —C(O)(ORₓ), and —C(O)NRₐR_b; and Rₓ consist of (C₁-C₄)alkyl, (C₃-C₆)cycloalkyl; and Rₐ and R_b are independently selected from the group consisting of hydrogen, (C₁-C₄)alkyl and halo(C₁-C₄)alkyl, or Rₐ and R_b may together with the nitrogen atom to which they are attached form a (4-6)membered heterocycloalkyl, wherein said heterocycloalkyl is optionally substituted with one or more (C₁-C₄)alkyl.

Clause 29. A compound according to clause 28, wherein $R^1$ is hydrogen or (C₁-C₄)-alkyl; and $R^2$ is pyrrolidinyl which is optionally substituted with —C(O)(C₁-C₄)alkyl; and $R^3$ is selected from the group consisting of (C₃-C₆)cycloalkyl, (4-6)membered heterocycloalkyl, and (5-6) membered heteroaryl.

Clause 30. A compound according to clause 29, wherein R' is hydrogen; and $R^2$ is pyrrolidinyl substituted with —C(O)(C₁-C₄)alkyl; and $R^3$ is selected from the group consisting of (4-6)membered heterocycloalkyl, and (5-6) membered heteroaryl.

Clause 31. A compound according to any one of the preceding clauses 1-19, wherein $R^1$ is hydrogen or (C₁-C₄)alkyl; and $R^2$ is piperidinyl, which is optionally substituted with $R^4$; $R^4$ is selected from the group consisting of —C(O)(C₁-C₄)alkyl, (C₁-C₄)alkyl, —C(O)O(C₁-C₆)alkyl, —C(O)NRₐR_b and —(C₁-C₄)alkyl-C(O)NRₐR_b; $R^3$ is selected from the group consisting of (C₁-C₆)alkyl, (C₃-C₆)cycloalkyl, (C₁-C₄)alkyl(C₃-C₆)cycloalkyl, halo(C₁-C₅)alkyl, (C₁-C₆)alkoxy, (C₁-C₆)alkyl(C₁-C₆)alkoxy, halo(C₁-C₄)alkyloxy, (4-6)-membered heterocycloalkyl, (C₁-C₄)alkyl(4-6)membered heterocycloalkyl, (5-6)-membered heteroaryl, (C₁-C₄)alkyl(5-6)membered heteroaryl, aryl and (C₁-C₄)-alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, cyano, hydroxyl, (C₁-C₄)alkyl, halo(C₁-C₄)alkyl and halo(C₁-C₄)alkyloxy, ORₓ, SRₓ, —S(O)₂Rₓ, —S(O)₂NRₐR_b, —C(O)(C₁-C₆)alkyl, —C(O)(ORₓ), and —C(O)NRₐR_b; and Rₓ consist of (C₁-C₄)alkyl, (C₃-C₆)cycloalkyl; and Rₐ and R_b are independently selected from the group consisting of hydrogen, (C₁-C₄)alkyl and halo(C₁-C₄)alkyl, or Rₐ and R_b may together with the nitrogen atom to which they are attached form a (4-6)membered heterocycloalkyl, wherein said heterocycloalkyl is optionally substituted with one or more (C₁-C₄)alkyl.

Clause 32. A compound according to clause 31 wherein R' is hydrogen or (C₁-C₄)-alkyl; and $R^2$ is piperidinyl, which is optionally substituted with $R^4$; and $R^4$ is selected from the group consisting of —C(O)(C₁-C₄)alkyl, and —C(O)O(C₁-C₄)alkyl; and $R^3$ is selected from the group consisting of (C₃-C₆)cycloalkyl, (4-6)membered hetero-cycloalkyl, and (5-6)membered heteroaryl, all of which are optionally substituted with one or more substituents independently selected from $R^5$; and $R^5$ is selected from the group consisting of halogen, cyano, hydroxyl, (C₁-C₄)alkyl, halo(C₁-C₄)alkyl and halo(C₁-C₄)alkyloxy, ORₓ, —SRₓ, —S(O)₂Rₓ, —S(O)₂NRₐR_b, —C(O)(C₁-C₆)alkyl, —C(O)(ORₓ), and —C(O)NRₐR_b; and Rₓ consist of (C₁-C₄)alkyl, (C₃-C₆)cycloalkyl; and Rₐ and R_b are independently selected from the group consisting of hydrogen, (C₁-C₄)alkyl and halo(C₁-C₄)alkyl, or Rₐ and R_b may together with the nitrogen atom to which they are attached form a (4-6)membered heterocycloalkyl, wherein said heterocycloalkyl is optionally substituted with one or more (C₁-C₄)alkyl.

Clause 33. A compound according to clause 32 wherein R' is hydrogen or (C₁-C₄)alkyl; and $R^2$ is piperidinyl which is optionally substituted with —C(O)(C₁-C₄)alkyl; and $R^3$ is selected from the group consisting of (C₃-C₆)cycloalkyl, (4-6)membered heterocycloalkyl, and (5-6)membered heteroaryl.

Clause 34. A compound according to clause 33 wherein $R^1$ is hydrogen; and $R^2$ is piperidinyl substituted with —C(O)(C₁-C₄)alkyl; and $R^3$ is selected from the group consisting of (4-6)membered heterocycloalkyl, and (5-6) membered heteroaryl.

Clause 35. A compound according to any one of the preceding clauses, of general formula (II)

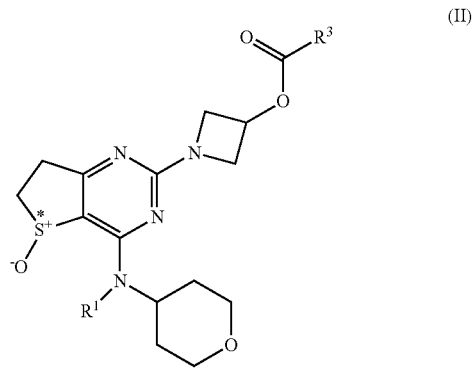

wherein
$R^1$ is hydrogen or (C₁-C₄)alkyl; and
$R^3$ is selected from the group consisting of (C₁-C₆)alkyl, (C₃-C₆)cycloalkyl, (C₁-C₄)-alkyl(C₃-C₆)cycloalkyl, halo(C₁-C₆)alkyl, (C₁-C₆)alkoxy, (C₁-C₆)alkyl(C₁-C₆)alkoxy, halo(C₁-C₄)alkyloxy, (4-6)membered heterocycloalkyl, (C₁-C₄)alkyl(4-6)membered heterocycloalkyl, (5-6)membered heteroaryl, (C₁-C₄)alkyl(5-6)membered heteroaryl, aryl and (C₁-C₄)alkylaryl; wherein said alkyl, cycloalkyl, heterocycloalkyl, heteroaryl and aryl are optionally substituted with one or more substituents independently selected from $R^5$; and
$R^5$ is selected from the group consisting of halogen, cyano, hydroxyl, (C₁-C₄)alkyl, halo(C₁-C₄)alkyl, halo(C₁-C₄)alkyloxy, ORₓ, SRₓ, —S(O)₂Rₓ, —S(O)₂NRₐR_b, —C(C)(C₁-C₆)alkyl, —C(O)(ORₓ), and —C(O)NRₐR_b; and
Rₐ and R_b are independently selected from the group consisting of hydrogen, (C₁-C₄)alkyl and halo(C₁-C₄)alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl; and $R_x$ consist of $(C_1-C_4)$alkyl, $(C_3-C_6)$cycloalkyl; and S* represents a chiral sulphur atom; and pharmaceutically acceptable salts, enantiomers, mixtures of enantiomers, diastereomers, mixtures of diastereomers, hydrates and solvates thereof.

Clause 36. A compound according to clause 35, wherein $R^1$ is hydrogen or $(C_1-C_4)$-alkyl; and $R^3$ is selected from the group consisting of $(C_3-C_6)$cycloalkyl, (4-6)-membered heterocycloalkyl, (5-6)membered heteroaryl and aryl, all of which are optionally substituted with one or more substituents independently selected from $R^5$; and $R^5$ is selected from the group consisting of halogen, cyano, hydroxyl, $(C_1-C_4)$alkyl, halo$(C_1-C_4)$alkyl and halo$(C_1-C_4)$alkyloxy, $OR_x$, $-SR_x$, $-S(O)_2R_x$, $-S(O)_2NR_aR_b$, $-C(O)(C_1-C_6)$alkyl, $-C(O)(OR_x)$, and $-C(O)NR_aR_b$; and $R_x$ consist of $(C_1-C_4)$alkyl, $(C_3-C_6)$cycloalkyl; and $R_a$ and $R_b$ are independently selected from the group consisting of hydrogen, $(C_1-C_4)$alkyl and halo$(C_1-C_4)$alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl.

Clause 37. A compound according to clause 36, wherein $R^1$ is hydrogen or methyl; and $R^3$ is selected from the group consisting of $(C_3-C_6)$cycloalkyl, (4-6)membered heterocycloalkyl and (5-6)membered heteroaryl.

Clause 38. A compound according to clause 37, wherein $R^1$ is hydrogen; and $R^3$ is selected from the group consisting of cyclopentyl, tetrahydropyranyl, isothiazolyl and thiazolyl.

Clause 39. A compound according to clause 37, wherein $R^1$ is methyl; and $R^3$ is selected from the group consisting of tetrahydropyranyl, isothiazolyl and thiazolyl.

Clause 40. A compound according to any one of the preceding clauses, wherein S* represents a chiral sulphur atom being in the R-configuration.

Clause 41. A compound according to any one of the preceding clauses 1-39, wherein S* represents a chiral sulphur atom being in the S-configuration.

Clause 42. A compound according to any one of the preceding clauses of general formula (IIa)

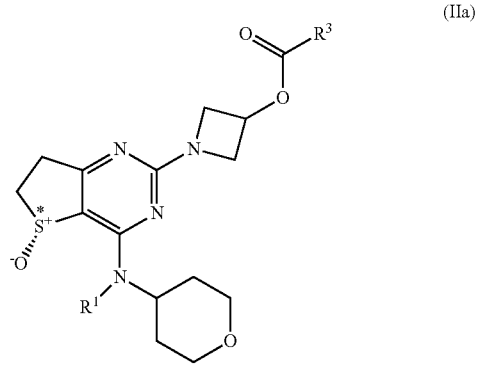

wherein
$R^1$ is hydrogen or $(C_1-C_4)$alkyl; and
$R^3$ is selected from the group consisting of $(C_1-C_6)$alkyl, $(C_3-C_6)$cycloalkyl, $(C_1-C_4)$alkyl$(C_3-C_6)$cycloalkyl, halo$(C_1-C_6)$alkyl, $(C_1-C_6)$alkoxy, $(C_1-C_6)$alkyl$(C_1-C_6)$alkoxy, halo$(C_1-C_4)$alkyloxy, (4-6)membered heterocycloalkyl, $(C_1-C_4)$alkyl(4-6)membered heterocycloalkyl, (5-6)membered heteroaryl, $(C_1-C_4)$alkyl(5-6)membered heteroaryl, aryl and $(C_1-C_4)$alkylaryl; wherein said alkyl, cycloalkyl, heterocycloalkyl, heteroaryl and aryl are optionally substituted with one or more substituents independently selected from $R^5$; and $R^5$ is selected from the group consisting of halogen, cyano, hydroxyl, $(C_1-C_4)$alkyl, halo$(C_1-C_4)$alkyl, halo$(C_1-C_4)$alkyloxy, $OR_x$, $-SR_x$, $-S(O)_2R_x$, $-S(O)_2NR_aR_b$, $-C(O)(C_1-C_6)$alkyl, $-C(O)(OR_x)$, and $-C(O)NR_aR_b$; and $R_a$ and $R_b$ are independently selected from the group consisting of hydrogen, $(C_1-C_4)$alkyl and halo$(C_1-C_4)$alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl; and $R_x$ consist of $(C_1-C_4)$alkyl, $(C_3-C_6)$cycloalkyl; and pharmaceutically acceptable salts, enantiomers, mixtures of enantiomers, hydrates and solvates thereof.

Clause 43. A compound according to clause 42, wherein $R^1$ is hydrogen or $(C_1-C_4)$-alkyl; and $R^3$ is selected from the group consisting of $(C_3-C_6)$cycloalkyl, (4-6)-membered heterocycloalkyl, (5-6)membered heteroaryl and aryl, all of which are optionally substituted with one or more substituents independently selected from $R^5$; and $R^5$ is selected from the group consisting of halogen, cyano, hydroxyl, $(C_1-C_4)$alkyl, halo$(C_1-C_4)$alkyl and halo$(C_1-C_4)$alkyloxy, $OR_x$, $-SR_x$, $-S(O)_2R_x$, $-S(O)_2NR_aR_b$, $-C(O)(C_1-C_6)$alkyl, $-C(O)(OR_x)$, and $-C(O)NR_aR_b$; and $R_x$ consist of $(C_1-C_4)$alkyl, $(C_3-C_6)$cycloalkyl; and $R_a$ and $R_b$ are independently selected from the group consisting of hydrogen, $(C_1-C_4)$alkyl and halo$(C_1-C_4)$alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl.

Clause 44. A compound according to clause 43, wherein $R^1$ is hydrogen or methyl; and $R^3$ is selected from the group consisting of $(C_3-C_6)$cycloalkyl, (4-6)membered heterocycloalkyl and (5-6)membered heteroaryl.

Clause 45. A compound according to clause 44, wherein $R^1$ is hydrogen or methyl; and $R^3$ is (5-6)membered heteroaryl.

Clause 46. A compound according to clause 45, wherein $R^1$ is hydrogen; and $R^3$ is isothiazolyl or thiazolyl.

Clause 47. A compound according to clause 45, wherein $R^1$ is methyl; and $R^3$ is isothiazolyl or thiazolyl.

Clause 48. A compound according to any one of the preceding clauses selected from the group consisting of
[1-[(5R)-5-Oxido-4-(tetrahydropyran-4-ylamino)-6,7-dihydrothieno[3,2-d]pyrimidin-5-ium-2-yl]azetidin-3-yl] isothiazole-4-carboxylate (Compound 004a),
[1-[(5R)-5-Oxido-4-(tetrahydropyran-4-ylamino)-6,7-dihydrothieno[3,2-d]pyrimidin-5-ium-2-yl]azetidin-3-yl] thiazole-4-carboxylate (Compound 005a),
[1-[4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009),
[1-[(5R)-4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009a),
[1-[4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010),

[1-[(5R)-4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010a);

and a pharmaceutically acceptable salt, enantiomer, mixture of enantiomers, hydrate or solvate thereof.

Clause 49. A compound which is
[1-[(5R)-5-Oxido-4-(tetrahydropyran-4-ylamino)-6,7-dihydrothieno[3,2-d]pyrimidin-5-ium-2-yl]azetidin-3-yl] isothiazole-4-carboxylate (Compound 004a).

Clause 50. A compound which is
[1-[(5R)-5-Oxido-4-(tetrahydropyran-4-ylamino)-6,7-dihydrothieno[3,2-d]pyrimidin-5-ium-2-yl]azetidin-3-yl] thiazole-4-carboxylate (Compound 005a).

Clause 51. A compound which is
[1-[4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009).

Clause 52. A compound which is
[1-[(5R)-4-[Methyl(tetrahydropyran-4-yl)amino]-5-oxido-6,7-dihydrothieno[3,2-d]pyrimidin-5-ium-2-yl]azetidin-3-yl] isothiazole-4-carboxylate (Compound 009a).

Clause 53. A compound which is
[1-[4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010).

Clause 54. A compound which is
[1-[(5R)-4-[Methyl(tetrahydropyran-4-yl)amino]-5-oxido-6,7-dihydrothieno[3,2-d]pyrimidin-5-ium-2-yl]azetidin-3-yl] thiazole-4-carboxylate (Compound 010a).

Clause 55. A compound according to any one of the clauses 1-47 selected from the group consisting of
[1-[(5R)-5-oxido-4-(tetrahydropyran-4-ylamino)-6,7-dihydrothieno[3,2-d]pyrimidin-5-ium-2-yl]azetidin-3-yl] cyclopentanecarboxylate
[1-[(5R)-5-oxido-4-(tetrahydropyran-4-ylamino)-6,7-dihydrothieno[3,2-d]pyrimidin-5-ium-2-yl]azetidin-3-yl] tetrahydropyran-4-carboxylate,
and a pharmaceutically acceptable salt, enantiomer, mixture of enantiomers, hydrate or solvate thereof.

Clause 56. A compound according to any one of clauses 1-47 selected from the group consisting of
[1-[4-[methyl(tetrahydropyran-4-yl)amino]-5-oxido-6,7-dihydrothieno[3,2-d]pyrimidin-5-ium-2-yl]azetidin-3-yl] 3-methoxypropanoate
[1-[4-[methyl(tetrahydropyran-4-yl)amino]-5-oxido-6,7-dihydrothieno[3,2-d]pyrimidin-5-ium-2-yl]azetidin-3-yl] 3-hydroxycyclobutanecarboxylate
[1-[4-[methyl(tetrahydropyran-4-yl)amino]-5-oxido-6,7-dihydrothieno[3,2-d]pyrimidin-5-ium-2-yl]azetidin-3-yl] 3-methylsulfanylpropanoate
[1-[4-[methyl(tetrahydropyran-4-yl)amino]-5-oxido-6,7-dihydrothieno[3,2-d]pyrimidin-5-ium-2-yl]azetidin-3-yl] benzoate
[1-[4-[methyl(tetrahydropyran-4-yl)amino]-5-oxido-6,7-dihydrothieno[3,2-d]pyrimidin-5-ium-2-yl]azetidin-3-yl] 1-methylpyrazole-3-carboxylate
[1-[4-[methyl(tetrahydropyran-4-yl)amino]-5-oxido-6,7-dihydrothieno[3,2-d]pyrimidin-5-ium-2-yl]azetidin-3-yl] 1-methylpyrazole-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 1-methylimidazole-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 2-methyloxazole-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 2-methyloxazole-5-carboxylate
[1-[4-[methyl(tetra-hydropyran-4-yl)amino]-5-oxido-6,7-dihydrothieno[3,2-d]pyrimidin-5-ium-2-yl]azetidin-3-yl] isothiazole-5-carboxylate
[1-[4-[methyl(tetrahydropyran-4-yl)amino]-5-oxido-6,7-dihydrothieno[3,2-d]pyrimidin-5-ium-2-yl]azetidin-3-yl] tetrahydropyran-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 2-methylbenzoate
[1-[4-[methyl(tetrahydropyran-4-yl)amino]-5-oxido-6,7-dihydrothieno[3,2-d]pyrimidin-5-ium-2-yl]azetidin-3-yl] 3-methylbenzoate
[1-[4-[methyl(tetrahydropyran-4-yl)amino]-5-oxido-6,7-dihydrothieno[3,2-d]pyrimidin-5-ium-2-yl]azetidin-3-yl] 4-methylbenzoate
[1-[4-[methyl(tetrahydropyran-4-yl)amino]-5-oxido-6,7-dihydrothieno[3,2-d]pyrimidin-5-ium-2-yl]azetidin-3-yl] 2-methylpyrimidine-5-carboxylate
[1-[4-[methyl(tetrahydropyran-4-yl)amino]-5-oxido-6,7-dihydrothieno[3,2-d]pyrimidin-5-ium-2-yl]azetidin-3-yl] 4-fluorobenzoate
[1-[4-[methyl(tetrahydropyran-4-yl)amino]-5-oxido-6,7-dihydrothieno[3,2-d]pyrimidin-5-ium-2-yl]azetidin-3-yl] 2-fluorobenzoate
[1-[4-[methyl(tetrahydropyran-4-yl)amino]-5-oxido-6,7-dihydrothieno[3,2-d]pyrimidin-5-ium-2-yl]azetidin-3-yl] 1-ethylpyrazole-3-carboxylate
[1-[4-[methyl(tetrahydropyran-4-yl)amino]-5-oxido-6,7-dihydrothieno[3,2-d]pyrimidin-5-ium-2-yl]azetidin-3-yl] 1,5-dimethylpyrazole-3-carboxylate
[1-[4-[methyl(tetrahydropyran-4-yl)amino]-5-oxido-6,7-dihydrothieno[3,2-d]pyrimidin-5-ium-2-yl]azetidin-3-yl] 1-ethylpyrazole-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 2-ethyloxazole-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 3-methylisothiazole-5-carboxylate
[1-[4-[methyl(tetrahydropyran-4-yl)amino]-5-oxido-6,7-dihydrothieno[3,2-d]pyrimidin-5-ium-2-yl]azetidin-3-yl] 2-methylthiazole-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 2-methylthiazole-5-carboxylate
[1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate
[1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate
[1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate
[1-[4-[methyl(tetrahydropyran-4-yl)amino]-5-oxido-6,7-dihydrothieno[3,2-d]pyrimidin-5-ium-2-yl]azetidin-3-yl] tetrahydrothiopyran-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 2,6-dimethylpyridine-4-carboxylate
[1-[4-[methyl(tetrahydropyran-4-yl)amino]-5-oxido-6,7-dihydrothieno[3,2-d]pyrimidin-5-ium-2-yl]azetidin-3-yl] 4-methoxybenzoate

[1-[4-[methyl(tetrahydropyran-4-yl)amino]-5-oxido-6,7-dihydrothieno[3,2-d]pyrimidin-5-ium-2-yl]azetidin-3-yl] 3-methoxybenzoate

[1-[4-[methyl(tetrahydropyran-4-yl)amino]-5-oxido-6,7-dihydrothieno[3,2-d]pyrimidin-5-ium-2-yl]azetidin-3-yl] 3-methylsulfonylpropanoate

[1-[4-[methyl(tetrahydropyran-4-yl)amino]-5-oxido-6,7-dihydrothieno[3,2-d]pyrimidin-5-ium-2-yl]azetidin-3-yl] 5-ethyl-1-methyl-pyrazole-3-carboxylate

[1-[4-[methyl(tetrahydropyran-4-yl)amino]-5-oxido-6,7-dihydrothieno[3,2-d]pyrimidin-5-ium-2-yl]azetidin-3-yl] 2-ethylthiazole-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 3-benzoate

[1-[4-[methyl(tetrahydropyran-4-yl)amino]-5-oxido-6,7-dihydrothieno[3,2-d]pyrimidin-5-ium-2-yl]azetidin-3-yl] 4-acetylbenzoate

[1-[4-[methyl(tetrahydropyran-4-yl)amino]-5-oxido-6,7-dihydrothieno[3,2-d]pyrimidin-5-ium-2-yl]azetidin-3-yl] 1-acetylpiperidine-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 1,1-dioxothiane-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 4-(methylcarbamoyl)benzoate O1-methyl O4-[1-[4-[methyl(tetrahydropyran-4-yl)amino]-5-oxido-6,7-dihydrothieno[3,2-d]pyrimidin-5-ium-2-yl]azetidin-3-yl] piperidine-1,4-dicarboxylate

[1-[4-[methyl(tetrahydropyran-4-yl)amino]-5-oxido-6,7-dihydrothieno[3,2-d]pyrimidin-5-ium-2-yl]azetidin-3-yl] 4-(dimethylcarbamoyl)benzoate

[1-[4-[methyl(tetrahydropyran-4-yl)amino]-5-oxido-6,7-dihydrothieno[3,2-d]pyrimidin-5-ium-2-yl]azetidin-3-yl] 4-methylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 1-(dimethylcarbamoyl)piperidine-4-carboxylate

[1-[4-[methyl(tetrahydropyran-4-yl)amino]-5-oxido-6,7-dihydrothieno[3,2-d]pyrimidin-5-ium-2-yl]azetidin-3-yl] 3-ethylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-ethylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-(methylsulfamoyl)benzoate

[1-[4-[methyl(tetrahydropyran-4-yl)amino]-5-oxido-6,7-dihydrothieno[3,2-d]pyrimidin-5-ium-2-yl]azetidin-3-yl] 3-isopropylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-isopropylsulfonylbenzoate

[1-[4-[methyl(tetrahydropyran-4-yl)amino]-5-oxido-6,7-dihydrothieno[3,2-d]pyrimidin-5-ium-2-yl]azetidin-3-yl] 4-(morpholine-4-carbonyl)benzoate

[1-[4-[methyl(tetrahydropyran-4-yl)amino]-5-oxido-6,7-dihydrothieno[3,2-d]pyrimidin-5-ium-2-yl]azetidin-3-yl] 4-cyclopentylsulfonylbenzoate, and a pharmaceutically acceptable salt, enantiomer, mixture of enantiomers, hydrate or solvate thereof.

Clause 57. A compound according to any one of the clauses 1-47 selected from the group consisting of

[1-[(5R)-4-[methyl(tetrahydropyran-4-yl)amino]-5-oxido-6,7-dihydrothieno[3,2-d]pyrimidin-5-ium-2-yl]azetidin-3-yl] pyridine-3-carboxylate

[1-[(5R)-4-[methyl(tetrahydropyran-4-yl)amino]-5-oxido-6,7-dihydrothieno[3,2-d]pyrimidin-5-ium-2-yl]azetidin-3-yl] 4-methylbenzoate, and a pharmaceutically acceptable salt, enantiomer, mixture of enantiomers, hydrate or solvate thereof.

Clause 58. A compound according to any one of the clauses 1-47 selected from the group consisting of

[1-[4-(6-oxaspiro[3.3]heptan-2-ylamino)-5-oxido-6,7-dihydrothieno[3,2-d]pyrimidin-5-ium-2-yl]azetidin-3-yl] isothiazole-4-carboxylate

[1-[4-(6-oxaspiro[3.3]heptan-2-ylamino)-5-oxido-6,7-dihydrothieno[3,2-d]pyrimidin-5-ium-2-yl]azetidin-3-yl] thiazole-4-carboxylate

[1-[4-(6-oxaspiro[3.3]heptan-2-ylamino)-5-oxido-6,7-dihydrothieno[3,2-d]pyrimidin-5-ium-2-yl]azetidin-3-yl] tetrahydropyran-4-carboxylate

[1-[(5R)-4-(6-oxaspiro[3.3]heptan-2-ylamino)-5-oxido-6,7-dihydrothieno[3,2-d]pyrimidin-5-ium-2-yl]azetidin-3-yl] isothiazole-4-carboxylate

[1-[(5S)-4-(6-oxaspiro[3.3]heptan-2-ylamino)-5-oxido-6,7-dihydrothieno[3,2-d]pyrimidin-5-ium-2-yl]azetidin-3-yl] isothiazole-4-carboxylate

[1-[(5R)-4-(6-oxaspiro[3.3]heptan-2-ylamino)-5-oxido-6,7-dihydrothieno[3,2-d]pyrimidin-5-ium-2-yl]azetidin-3-yl] thiazole-4-carboxylate

[1-[(5S)-4-(6-oxaspiro[3.3]heptan-2-ylamino)-5-oxido-6,7-dihydrothieno[3,2-d]pyrimidin-5-ium-2-yl]azetidin-3-yl] thiazole-4-carboxylate, and a pharmaceutically acceptable salt, enantiomer, mixture of enantiomers, hydrate or solvate thereof.

Clause 59. A compound according to any one of the clauses 1-47 selected from the group consisting of

[1-[4-[[(3S)-1-acetylpyrrolidin-3-yl]amino]-5-oxido-6,7-dihydrothieno[3,2-d]pyrimidin-5-ium-2-yl]azetidin-3-yl] isothiazole-4-carboxylate

[1-[4-[[(3S)-1-acetylpyrrolidin-3-yl]amino]-5-oxido-6,7-dihydrothieno[3,2-d]pyrimidin-5-ium-2-yl]azetidin-3-yl] thiazole-4-carboxylate

[1-[4-[[(3S)-1-acetylpyrrolidin-3-yl]amino]-5-oxido-6,7-dihydrothieno[3,2-d]pyrimidin-5-ium-2-yl]azetidin-3-yl] tetrahydropyran-4-carboxylate

[1-[4-[[(3R)-1-acetylpyrrolidin-3-yl]amino]-5-oxido-6,7-dihydrothieno[3,2-d]pyrimidin-5-ium-2-yl]azetidin-3-yl] tetrahydropyran-4-carboxylate, and a pharmaceutically acceptable salt, enantiomer, mixture of enantiomers, hydrate or solvate thereof.

Clause 60. A compound according to any one of the clauses 1-47 selected from the group consisting of

[1-[4-[(1-acetyl-4-piperidyl)amino]-5-oxido-6,7-dihydrothieno[3,2-d]pyrimidin-5-ium-2-yl]azetidin-3-yl] thiazole-4-carboxylate

[1-[4-[(1-acetyl-4-piperidyl)amino]-5-oxido-6,7-dihydrothieno[3,2-d]pyrimidin-5-ium-2-yl]azetidin-3-yl] tetrahydropyran-4-carboxylate, and a pharmaceutically acceptable salt, enantiomer, mixture of enantiomers, hydrate or solvate thereof.

Clause 61. A pharmaceutical composition comprising a compound according to any one of clauses 1-60 together with a pharmaceutically acceptable vehicle or excipient or pharmaceutically acceptable carrier(s).

Clause 62. The pharmaceutical composition according to clause 61 further comprising one or more other therapeutically active compound(s).

Clause 63. A use of the compound according to any of the clauses 1-60, for the manufacture of a pharmaceutical composition.

Clause 64. The use of a compound according to clause 63 in the manufacture of a pharmaceutical composition for the treatment or amelioration of a disease, disorder or condition responsive to PDE4 inhibitory activity.

Clause 65 The use according to clause 64, wherein the disease, disorder or condition is dermal diseases or conditions.

Clause 66. The use according to clause 65, wherein the disease, disorder or condition is proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 67. The compound according to any of the clauses 1-60, for use as a medicament.

Clause 68. The compound according to clause 67 for use in the treatment or amelioration of a disease, disorder or condition responsive to PDE4 inhibitory activity.

Clause 69. The compound according to clause 67 for use in the treatment or amelioration of dermal diseases or conditions.

Clause 70. The compound according to clause 67 for use in the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 71. A method for treatment or alleviation of a disease or a disorder or a condition responsive to PDE4 inhibitory activity, which method comprises the step of administering to a living animal body a therapeutically effective amount of a compound according to any of the clauses 1-60.

Clause 72. A method of treating or ameliorating dermal diseases or conditions, the method comprising administering to a person suffering from at least one of said diseases an effective amount of one or more compounds according to according to any one of clauses 1-60, optionally together with a pharmaceutically acceptable carrier or one or more excipients, optionally in combination with other therapeutically active compounds.

Clause 73. The method according to clause 72, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 74. An intermediate compound of general formula (III)

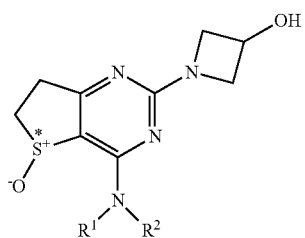

wherein $R^1$ is hydrogen or $(C_1-C_4)$alkyl; and
wherein $R^2$ is selected from the group consisting of tetra-hydropyranyl, oxaspiro-heptanyl, pyrrolidinyl and piperidinyl; wherein said pyrrolidinyl and piperidinyl are optionally substituted with one or more substituents independently selected from $R^4$; and wherein $R^4$ is selected from the group consisting of —C(O)$(C_1-C_4)$alkyl, $(C_1-C_4)$alkyl, —C(O)O$(C_1-C_6)$alkyl, —C(O)NR$_a$R$_b$ and —$(C_1-C_4)$alkyl-C(O)NR$_a$R$_b$; and wherein $R_a$ and $R_b$ are independently selected from the group consisting of hydrogen, $(C_1-C_4)$alkyl and halo$(C_1-C_4)$alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl; and S* represent a chiral sulphur atom; and pharmaceutically acceptable salts, enantiomers, mixtures of enantiomers, hydrates and solvates thereof.

Clause 75. An intermediate compound according to clause 74 selected from the group consisting of 1-[(5R)-5-Oxido-4-(tetrahydropyran-4-ylamino)-6,7-dihydrothieno[3,2-d]pyrimidin-5-ium-2-yl]azetidin-3-ol (Compound 003a), 1-[4-[Methyl(tetrahydropyran-4-yl)amino]-5-oxido-6,7-dihydrothieno[3,2-d]pyrimidin-5-ium-2-yl]azetidin-3-ol (Compound 008), 1-[(5R)-4-[Methyl(tetrahydropyran-4-yl)amino]-5-oxido-6,7-dihydrothieno[3,2-d]pyrimidin-5-ium-2-yl]azetidin-3-ol (Compound 008a), and a pharmaceutically acceptable salt, enantiomer, mixture of enantiomers, hydrate and solvate thereof.

The invention claimed is:

1. A compound of general formula (I)

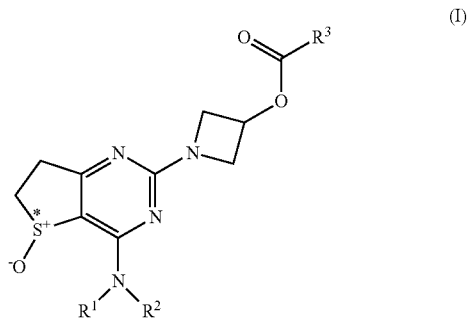

wherein:

$R^1$ is hydrogen or $(C_1-C_4)$alkyl;

$R^2$ is selected from the group consisting of tetra-hydropyranyl, oxaspiro-heptanyl, pyrrolidinyl and piperidinyl; wherein said pyrrolidinyl and piperidinyl are optionally substituted with one or more substituents independently selected from $R^4$;

$R^4$ is selected from the group consisting of —C(O)$(C_1-C_4)$alkyl, $(C_1-C_4)$alkyl, —S(O)$_2$R$_x$, —S(O)$_2$NR$_a$R$_b$, —C(O)O$(C_1-C_6)$alkyl, —C(O)NR$_a$R$_b$ and —$(C_1-C_4)$alkyl-C(O)NR$_a$R$_b$;

$R_a$ and $R_b$ are independently selected from the group consisting of hydrogen, $(C_1-C_4)$alkyl and halo$(C_1-C_4)$alkyl, or $R_a$ and $R_b$ may together with the nitrogen atom to which they are attached form a (4-6)membered heterocycloalkyl, wherein said heterocycloalkyl is optionally substituted with one or more $(C_1-C_4)$alkyl;

R³ is selected from the group consisting of (C₁-C₆)alkyl, (C₃-C₆)cycloalkyl, (C₁-C₄)alkyl(C₃-C₆)cycloalkyl, halo(C₁-C₆)alkyl, (C₁-C₆)alkoxy, (C₁-C₆)alkyl(C₁-C₆)alkoxy, halo(C₁-C₄)alkyloxy, (4-6)membered heterocycloalkyl, (C₁-C₄)alkyl(4-6)membered heterocycloalkyl, (5-6)membered heteroaryl, (C₁-C₄))alkyl(5-6)membered heteroaryl, aryl and (C₁-C₄)alkylaryl; wherein said alkyl, cycloalkyl, heterocycloalkyl, heteroaryl and aryl are optionally substituted with one or more substituents independently selected from R⁵;

R⁵ is selected from the group consisting of halogen, cyano, hydroxyl, (C₁-C₄)alkyl, halo(C₁-C₄)alkyl, halo (C₁-C₄)alkyloxy, OR_x, —SR_x, —S(O)₂R_x, —S(O)₂NR_aR_b, —C(O)R_x, —C(O)(OR_x), and —C(O)NR_aR_b;

R_x consist of (C₁-C₄)alkyl, (C₃-C₆)cycloalkyl, heterocycloalkyl; and

S* represent a chiral sulphur atom; or a pharmaceutically acceptable salt, enantiomer, mixtures of enantiomers, diastereomer, mixtures of diastereomers, hydrate or solvates thereof.

2. The compound according to claim 1 of general formula (II)

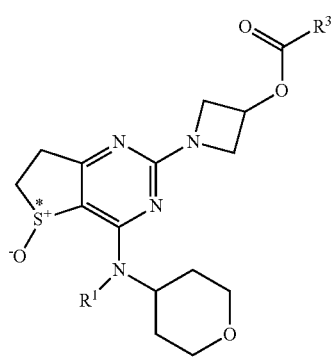

(II)

or a pharmaceutically acceptable salt, enantiomer, mixture of enantiomers, diastereomer, mixture of diastereomers, hydrate or solvate thereof.

3. The compound according to claim 1 of general formula (IIa)

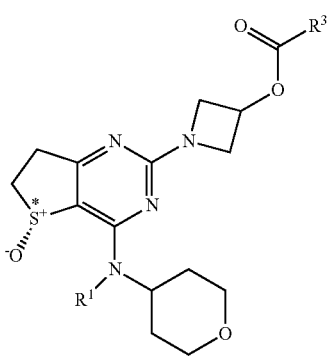

(IIa)

or a pharmaceutically acceptable salt, enantiomer, mixture of enantiomers, diastereomer, mixture of diastereomers, hydrate or solvate thereof.

4. The compound according to claim 1, wherein R¹ is hydrogen or methyl.

5. The compound according to claim 1, wherein R³ is selected from the group consisting of (C₃-C₆)cycloalkyl, (4-6)membered heterocycloalkyl, and (5-6)membered heteroaryl.

6. The compound according to claim 1, wherein the compound is selected from the group consisting of:
   (i) [1-[(5R)-5-Oxido-4-(tetrahydropyran-4-ylamino)-6,7-dihydrothieno[3,2-d]pyrimidin-5-ium-2-yl]azetidin-3-yl] isothiazole-4-carboxylate;
   (ii) [1-[(5R)-5-Oxido-4-(tetrahydropyran-4-ylamino)-6,7-dihydrothieno[3,2-d]pyrimidin-5-ium-2-yl]azetidin-3-yl] thiazole-4-carboxylate;
   (iii) [11-[4-[Methyl(tetrahydropyran-4-yl)amino]-5-oxido-6,7-dihydrothieno[3,2-d]pyrimidin-5-ium-2-yl] azetidin-3-yl] isothiazole-4-carboxylate;
   (iv) [1-[(5R)-4-[Methyl(tetrahydropyran-4-yl)amino]-5-oxido-6,7-dihydrothieno[3,2-d]pyrimidin-5-ium-2-yl] azetidin-3-yl] isothiazole-4-carboxylate;
   (v) [1-[4-[Methyl(tetrahydropyran-4-yl)amino]-5-oxido-6,7-dihydrothieno[3,2-d]pyrimidin-5-ium-2-yl]azetidin-3-yl] thiazole-4-carboxylate;
   (vi) [1-[(5R)-4-[Methyl(tetrahydropyran-4-yl)amino]-5-oxido-6,7-dihydrothieno[3,2-d]pyrimidin-5-ium-2-yl] azetidin-3-yl] thiazole-4-carboxylate;
   or a pharmaceutically acceptable salt, enantiomer, mixture of enantiomers, hydrate or solvate thereof.

7. The compound according to claim 1, wherein the compound is selected from the group consisting of:
   (i) [1-[(5R)-5-oxido-4-(tetrahydropyran-4-ylamino)-6,7-dihydrothieno[3,2-d]pyrimidin-5-ium-2-yl]azetidin-3-yl] cyclopentanecarboxylate;
   (ii) [1-[(5R)-5-oxido-4-(tetrahydropyran-4-ylamino)-6,7-dihydrothieno[3,2-d]pyrimidin-5-ium-2-yl]azetidin-3-yl] tetrahydropyran-4-carboxylate;
   (iii) [1-[4-[methyl(tetrahydropyran-4-yl)amino]-5-oxido-6,7-dihydrothieno[3,2-d]pyrimidin-5-ium-2-yl]azetidin-3-yl] 3-methoxypropanoate;
   (iv) [1-[4-[methyl(tetrahydropyran-4-yl)amino]-5-oxido-6,7-dihydrothieno[3,2-d]pyrimidin-5-ium-2-yl]azetidin-3-yl] 3-hydroxycyclobutanecarboxylate;
   (v) [1-[4-[methyl(tetrahydropyran-4-yl)amino]-5-oxido-6,7-dihydrothieno[3,2-d]pyrimidin-5-ium-2-yl]azetidin-3-yl] 3-methylsulfanylpropanoate;
   (vi) [1-[4-[methyl(tetrahydropyran-4-yl)amino]-5-oxido-6,7-dihydrothieno[3,2-d]pyrimidin-5-ium-2-yl]azetidin-3-yl] benzoate;
   (vii) [1-[4-[methyl(tetrahydropyran-4-yl)amino]-5-oxido-6,7-dihydrothieno[3,2-d]pyrimidin-5-ium-2-yl]azetidin-3-yl] 1-methylpyrazole-3-carboxylate;
   (viii) [1-[4-[methyl(tetrahydropyran-4-yl)amino]-5-oxido-6,7-dihydrothieno[3,2-d]pyrimidin-5-ium-2-yl] azetidin-3-yl] 1-methylpyrazole-4-carboxylate;
   (ix) [1-[4-[methyl(tetrahydropyran-4-yl)amino]-5-oxido-6,7-dihydrothieno[3,2-d]pyrimidin-5-ium-2-yl]azetidin-3-yl] 1-methylimidazole-4-carboxylate;
   (x) [1-[4-[methyl(tetrahydropyran-4-yl)amino]-5-oxido-6,7-dihydrothieno[3,2-d]pyrimidin-5-ium-2-yl]azetidin-3-yl] 2-methyloxazole-4-carboxylate;
   (xi) [1-[4-[methyl(tetrahydropyran-4-yl)amino]-5-oxido-6,7-dihydrothieno[3,2-d]pyrimidin-5-ium-2-yl]azetidin-3-yl] 2-methyloxazole-5-carboxylate;
   (xii) [1-[4-[methyl(tetra-hydropyran-4-yl)amino]-5-oxido-6,7-dihydrothieno[3,2-d]pyrimidin-5-ium-2-yl] azetidin-3-yl] isothiazole-5-carboxylate;
   (xiii) [1-[4-[methyl(tetrahydropyran-4-yl)amino]-5-oxido-6,7-dihydrothieno[3,2-d]pyrimidin-5-ium-2-yl] azetidin-3-yl] tetrahydropyran-4-carboxylate;

(xiv) [1-[4-[methyl(tetrahydropyran-4-yl)amino]-5-oxido-6,7-dihydrothieno[3,2-d]pyrimidin-5-ium-2-yl]azetidin-3-yl] 2-methylbenzoate;
(xv) [1-[4-[methyl(tetrahydropyran-4-yl)amino]-5-oxido-6,7-dihydrothieno[3,2-d]pyrimidin-5-ium-2-yl]azetidin-3-yl] 3-methylbenzoate;
(xvi) [1-[4-[methyl(tetrahydropyran-4-yl)amino]-5-oxido-6,7-dihydrothieno[3,2-d]pyrimidin-5-ium-2-yl]azetidin-3-yl] 4-methylbenzoate;
(xvii) [1-[4-[methyl(tetrahydropyran-4-yl)amino]-5-oxido-6,7-dihydrothieno[3,2-d]pyrimidin-5-ium-2-yl]azetidin-3-yl] 2-methylpyrimidine-5-carboxylate;
(xviii) [1-[4-[methyl(tetrahydropyran-4-yl)amino]-5-oxido-6,7-dihydrothieno[3,2-d]pyrimidin-5-ium-2-yl]azetidin-3-yl] 4-fluorobenzoate;
(xix) [1-[4-[methyl(tetrahydropyran-4-yl)amino]-5-oxido-6,7-dihydrothieno[3,2-d]pyrimidin-5-ium-2-yl]azetidin-3-yl] 2-fluorobenzoate;
(xx) [1-[4-[methyl(tetrahydropyran-4-yl)amino]-5-oxido-6,7-dihydrothieno[3,2-d]pyrimidin-5-ium-2-yl]azetidin-3-yl] 1-ethylpyrazole-3-carboxylate;
(xxi) [1-[4-[methyl(tetrahydropyran-4-yl)amino]-5-oxido-6,7-dihydrothieno[3,2-d]pyrimidin-5-ium-2-yl]azetidin-3-yl] 1,5-dimethylpyrazole-3-carboxylate;
(xxii) [1-[4-[methyl(tetrahydropyran-4-yl)amino]-5-oxido-6,7-dihydrothieno[3,2-d]pyrimidin-5-ium-2-yl]azetidin-3-yl] 1-ethylpyrazole-4-carboxylate;
(xxiii) [1-[4-[methyl(tetrahydropyran-4-yl)amino]-5-oxido-6,7-dihydrothieno[3,2-d]pyrimidin-5-ium-2-yl]azetidin-3-yl] 2-ethyloxazole-4-carboxylate;
(xxiv) [1-[4-[methyl(tetrahydropyran-4-yl)amino]-5-oxido-6,7-dihydrothieno[3,2-d]pyrimidin-5-ium-2-yl]azetidin-3-yl] 3-methylisothiazole-5-carboxylate;
(xxv) [1-[4-[methyl(tetrahydropyran-4-yl)amino]-5-oxido-6,7-dihydrothieno[3,2-d]pyrimidin-5-ium-2-yl]azetidin-3-yl] 2-methylthiazole-4-carboxylate;
(xxvi) [1-[4-[methyl(tetrahydropyran-4-yl)amino]-5-oxido-6,7-dihydrothieno[3,2-d]pyrimidin-5-ium-2-yl]azetidin-3-yl] 2-methylthiazole-5-carboxylate;
(xxvii) [1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate;
(xxviii) [1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate;
(xxix) [1-[4-[methyl(tetrahydropyran-4-yl)amino]-5-oxido-6,7-dihydrothieno[3,2-d]pyrimidin-5-ium-2-yl]azetidin-3-yl] 4-hydroxycyclohexanecarboxylate;
(xxx) [1-[4-[methyl(tetrahydropyran-4-yl)amino]-5-oxido-6,7-dihydrothieno[3,2-d]pyrimidin-5-ium-2-yl]azetidin-3-yl] tetrahydrothiopyran-4-carboxylate;
(xxxi) [1-[4-[methyl(tetrahydropyran-4-yl)amino]-5-oxido-6,7-dihydrothieno[3,2-d]pyrimidin-5-ium-2-yl]azetidin-3-yl] 2,6-dimethylpyridine-4-carboxylate;
(xxxii) [1-[4-[methyl(tetrahydropyran-4-yl)amino]-5-oxido-6,7-dihydrothieno[3,2-d]pyrimidin-5-ium-2-yl]azetidin-3-yl] 4-methoxybenzoate;
(xxxiii) [1-[4-[methyl(tetrahydropyran-4-yl)amino]-5-oxido-6,7-dihydrothieno[3,2-d]pyrimidin-5-ium-2-yl]azetidin-3-yl] 3-methoxybenzoate;
(xxxiv) [1-[4-[methyl(tetrahydropyran-4-yl)amino]-5-oxido-6,7-dihydrothieno[3,2-d]pyrimidin-5-ium-2-yl]azetidin-3-yl] 3-methylsulfonylpropanoate;
(xxxv) [1-[4-[methyl(tetrahydropyran-4-yl)amino]-5-oxido-6,7-dihydrothieno[3,2-d]pyrimidin-5-ium-2-yl]azetidin-3-yl] 5-ethyl-1-methyl-pyrazole-3-carboxylate;
(xxxvi) [1-[4-[methyl(tetrahydropyran-4-yl)amino]-5-oxido-6,7-dihydrothieno[3,2-d]pyrimidin-5-ium-2-yl]azetidin-3-yl] 2-ethylthiazole-4-carboxylate;
(xxxvii) [1-[4-[methyl(tetrahydropyran-4-yl)amino]-5-oxido-6,7-dihydrothieno[3,2-d]pyrimidin-5-ium-2-yl]azetidin-3-yl] 3-benzoate;
(xxxviii) [1-[4-[methyl(tetrahydropyran-4-yl)amino]-5-oxido-6,7-dihydrothieno[3,2-d]pyrimidin-5-ium-2-yl]azetidin-3-yl] 4-acetylbenzoate;
(xxxix) [1-[4-[methyl(tetrahydropyran-4-yl)amino]-5-oxido-6,7-dihydrothieno[3,2-d]pyrimidin-5-ium-2-yl]azetidin-3-yl] 1-acetylpiperidine-4-carboxylate;
(xl) [1-[4-[methyl(tetrahydropyran-4-yl)amino]-5-oxido-6,7-dihydrothieno[3,2-d]pyrimidin-5-ium-2-yl]azetidin-3-yl] 1,1-dioxothiane-4-carboxylate;
(xli) [1-[4-[methyl(tetrahydropyran-4-yl)amino]-5-oxido-6,7-dihydrothieno[3,2-d]pyrimidin-5-ium-2-yl]azetidin-3-yl] 4-(methylcarbamoyl)benzoate;
(xlii) O1-methyl O4-[1-[4-[methyl(tetrahydropyran-4-yl)amino]-5-oxido-6,7-dihydrothieno[3,2-d]pyrimidin-5-ium-2-yl]azetidin-3-yl] piperidine-1,4-dicarboxylate;
(xliii) [1-[4-[methyl(tetrahydropyran-4-yl)amino]-5-oxido-6,7-dihydrothieno[3,2-d]pyrimidin-5-ium-2-yl]azetidin-3-yl] 4-(dimethylcarbamoyl)benzoate;
(xliv) [1-[4-[methyl(tetrahydropyran-4-yl)amino]-5-oxido-6,7-dihydrothieno[3,2-d]pyrimidin-5-ium-2-yl]azetidin-3-yl] 4-methylsulfonylbenzoate;
(xlv) [1-[4-[methyl(tetrahydropyran-4-yl)amino]-5-oxido-6,7-dihydrothieno[3,2-d]pyrimidin-5-ium-2-yl]azetidin-3-yl] 1-(dimethylcarbamoyl)piperidine-4-carboxylate;
(xlvi) [1-[4-[methyl(tetrahydropyran-4-yl)amino]-5-oxido-6,7-dihydrothieno[3,2-d]pyrimidin-5-ium-2-yl]azetidin-3-yl] 3-ethylsulfonylbenzoate;
(xlvii) [1-[4-[methyl(tetrahydropyran-4-yl)amino]-5-oxido-6,7-dihydrothieno[3,2-d]pyrimidin-5-ium-2-yl]azetidin-3-yl] 4-ethylsulfonylbenzoate;
(xlviii) [1-[4-[methyl(tetrahydropyran-4-yl)amino]-5-oxido-6,7-dihydrothieno[3,2-d]pyrimidin-5-ium-2-yl]azetidin-3-yl] 4-(methylsulfamoyl)benzoate;
(xlix) [1-[4-[methyl(tetrahydropyran-4-yl)amino]-5-oxido-6,7-dihydrothieno[3,2-d]pyrimidin-5-ium-2-yl]azetidin-3-yl] 3-isopropylsulfonylbenzoate;
(l) [1-[4-[methyl(tetrahydropyran-4-yl)amino]-5-oxido-6,7-dihydrothieno[3,2-d]pyrimidin-5-ium-2-yl]azetidin-3-yl] 4-isopropylsulfonylbenzoate;
(li) [1-[4-[methyl(tetrahydropyran-4-yl)amino]-5-oxido-6,7-dihydrothieno[3,2-d]pyrimidin-5-ium-2-yl]azetidin-3-yl] 4-(morpholine-4-carbonyl)benzoate;
(lii) [1-[4-[methyl(tetrahydropyran-4-yl)amino]-5-oxido-6,7-dihydrothieno[3,2-d]pyrimidin-5-ium-2-yl]azetidin-3-yl] 4-cyclopentylsulfonylbenzoate;
(liii) [1-[(5R)-4-[methyl(tetrahydropyran-4-yl)amino]-5-oxido-6,7-dihydrothieno[3,2-d]pyrimidin-5-ium-2-yl]azetidin-3-yl] pyridine-3-carboxylate;
(liv) [1-[(5R)-4-[methyl(tetrahydropyran-4-yl)amino]-5-oxido-6,7-dihydrothieno[3,2-d]pyrimidin-5-ium-2-yl]azetidin-3-yl] 4-methylbenzoate;
(lv) [1-[4-(6-oxaspiro[3.3]heptan-2-ylamino)-5-oxido-6,7-dihydrothieno[3,2-d]pyrimidin-5-ium-2-yl]azetidin-3-yl] isothiazole-4-carboxylate;
(lvi) [1-[4-(6-oxaspiro[3.3]heptan-2-ylamino)-5-oxido-6,7-dihydrothieno[3,2-d]pyrimidin-5-ium-2-yl]azetidin-3-yl] thiazole-4-carboxylate;
(lvii) [1-[4-(6-oxaspiro[3.3]heptan-2-ylamino)-5-oxido-6,7-dihydrothieno[3,2-d]pyrimidin-5-ium-2-yl]azetidin-3-yl] tetrahydropyran-4-carboxylate;

(lviii) [1-[(5R)-4-(6-oxaspiro[3.3]heptan-2-ylamino)-5-oxido-6,7-dihydrothieno[3,2-d]pyrimidin-5-ium-2-yl] azetidin-3-yl] isothiazole-4-carboxylate;
(lix) [1-[(5S)-4-(6-oxaspiro[3.3]heptan-2-ylamino)-5-oxido-6,7-dihydrothieno[3,2-d]pyrimidin-5-ium-2-yl] azetidin-3-yl] isothiazole-4-carboxylate;
(lx) [1-[(5R)-4-(6-oxaspiro[3.3]heptan-2-ylamino)-5-oxido-6,7-dihydrothieno[3,2-d]pyrimidin-5-ium-2-yl] azetidin-3-yl] thiazole-4-carboxylate;
(lxi) [1-[(5S)-4-(6-oxaspiro[3.3]heptan-2-ylamino)-5-oxido-6,7-dihydrothieno[3,2-d]pyrimidin-5-ium-2-yl] azetidin-3-yl] thiazole-4-carboxylate;
(lxii) [1-[4-[[(3S)-1-acetylpyrrolidin-3-yl]amino]-5-oxido-6,7-dihydrothieno[3,2-d]pyrimidin-5-ium-2-yl] azetidin-3-yl] isothiazole-4-carboxylate;
(lxiii) [1-[4-[[(3S)-1-acetylpyrrolidin-3-yl]amino]-5-oxido-6,7-dihydrothieno[3,2-d]pyrimidin-5-ium-2-yl] azetidin-3-yl] thiazole-4-carboxylate;
(lxiv) [1-[4-[[(3S)-1-acetylpyrrolidin-3-yl]amino]-5-oxido-6,7-dihydrothieno[3,2-d]pyrimidin-5-ium-2-yl] azetidin-3-yl] tetrahydropyran-4-carboxylate;
(lxv) [1-[4-[[(3R)-1-acetylpyrrolidin-3-yl]amino]-5-oxido-6,7-dihydrothieno[3,2-d]pyrimidin-5-ium-2-yl] azetidin-3-yl] tetrahydropyran-4-carboxylate;
(lxvi) [1-[4-[(1-acetyl-4-piperidyl)amino]-5-oxido-6,7-dihydrothieno[3,2-d]pyrimidin-5-ium-2-yl]azetidin-3-yl] thiazole-4-carboxylate;
(lvii) [1-[4-[(1-acetyl-4-piperidyl)amino]-5-oxido-6,7-dihydrothieno[3,2-d]pyrimidin-5-ium-2-yl]azetidin-3-yl] tetrahydropyran-4-carboxylate
or a pharmaceutically acceptable salt, enantiomer, mixture of enantiomers, hydrate or solvate thereof.

8. A pharmaceutical composition comprising a compound according to any one of claim 1 and one or more pharmaceutically acceptable vehicles, excipients, or carriers.

9. A method of treating or ameliorating a dermal disease or condition, comprising administering to a person in need thereof an effective amount of one or more compounds according to according to claim 1, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

10. A method of treating or ameliorating a dermal disease or condition, comprising administering to a person in need thereof an effective amount of the pharmaceutical composition according to according to claim 8, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

11. The compound according to claim 2, wherein $R^1$ is hydrogen or methyl.

12. The compound according to claim 2, wherein $R^3$ is selected from the group consisting of $(C_3-C_6)$cycloalkyl, (4-6)membered hetero-cycloalkyl, and (5-6)membered heteroaryl.

13. The compound according to claim 12, wherein $R^3$ is cyclopentyl, tetrahydropyranyl, 4-isothiazolyl, or 4-thiazolyl.

14. The compound according to claim 3, wherein $R^1$ is hydrogen or methyl.

15. The compound according to claim 3, wherein $R^3$ is selected from the group consisting of $(C_3-C_6)$cycloalkyl, (4-6)membered hetero-cycloalkyl, and (5-6)membered heteroaryl.

16. The compound according to claim 15, wherein $R^3$ is cyclopentyl, tetrahydropyranyl, 4-isothiazolyl, or 4-thiazolyl.

17. The compound according to claim 1, wherein the compound is:
[1-[(5R)-4-[Methyl(tetrahydropyran-4-yl)amino]-5-oxido-6,7-dihydrothieno[3,2-d]pyrimidin-5-ium-2-yl] azetidin-3-yl] isothiazole-4-carboxylate or a pharmaceutically acceptable salt, enantiomer, mixture of enantiomers, hydrate or solvate thereof.

\* \* \* \* \*